/

US007842666B2

(12) United States Patent
Filbin et al.

(10) Patent No.: US 7,842,666 B2
(45) Date of Patent: *Nov. 30, 2010

(54) INHIBITORS OF MYELIN-ASSOCIATED GLYCOPROTEIN (MAG) ACTIVITY FOR REGULATING NEURAL GROWTH AND REGENERATION

(75) Inventors: Marie T. Filbin, New York, NY (US); Marco Domeniconi, New York, NY (US); Zixuan Cao, Elmhurst, NY (US)

(73) Assignee: Research Foundation of City University of New York, New York, NY (US)

( * ) Notice: Subject to any disclaimer, the term of this patent is extended or adjusted under 35 U.S.C. 154(b) by 314 days.

This patent is subject to a terminal disclaimer.

(21) Appl. No.: 10/327,213

(22) Filed: Dec. 20, 2002

(65) Prior Publication Data

US 2004/0121341 A1    Jun. 24, 2004

(51) Int. Cl.
*A61K 38/17* (2006.01)
*A61K 38/08* (2006.01)
*A61K 38/04* (2006.01)
*C07K 7/06* (2006.01)
*C07K 14/47* (2006.01)

(52) U.S. Cl. .................. 514/12; 530/350; 530/324; 530/328; 530/329; 530/330; 514/15; 514/17

(58) Field of Classification Search .................. None
See application file for complete search history.

(56) References Cited

U.S. PATENT DOCUMENTS

| 5,242,798 A * | 9/1993 | Sutcliffe ..................... 435/7.1 |
| 5,932,542 A | 8/1999 | Filbin ............................. 514/8 |
| 6,124,438 A * | 9/2000 | Sutcliffe .................. 530/387.9 |
| 6,203,792 B1 | 3/2001 | Filbin ....................... 424/133.1 |
| 6,399,577 B1 | 6/2002 | Filbin ............................ 514/23 |
| 2002/0012965 A1 | 1/2002 | Strittmatter |
| 2002/0077295 A1 | 6/2002 | Strittmatter |
| 2003/0194704 A1 * | 10/2003 | Penn et al. ..................... 435/6 |

FOREIGN PATENT DOCUMENTS

WO    WO 97/01352    1/1997

OTHER PUBLICATIONS

Cao et al. 2000. Society for Neuroscience Abstracts 26(1-2): Abstract 230.5.*
Chothia 1997. Annual Review of Biochemistry 66:823-862.*
Lo et al. 1998. Protein Engineering 11:495-500.*
Patch et al. 2002. Current Opinion in Chemical Biology 6:872-877.*
Cao et al. 2002. Abstracts of papers presented at the 2002 meeting on axonal guidance and neural plasticity. Sep. 25-29, 2002, p. 45.*
Lai 1987. Proc Natl Acad Sci USA 84:4337-4341.*
Fermentas Certificate of Analysis 2006 for Bsh1236I (FnuDII).*
Noronha 1989 (Journal of Molecular Neuroscience 1:159-170).*
Tropak 1994 (Journal of Neurochemistry 62:854-862).*

GenBank Accession No. M14871, publicly available Apr. 27, 1993.*
Meyer-Franke, A. et al., "Functional Topography of Myelin-Associated Glycoprotein. II. Mapping of Domains on Molecular Fragments," *Journal of Neuroscience Research*, 41:311-323(1995).
Quarles, R.H., "Glycoproteins of Myelin Sheaths," *Journal of Molecular Neuroscience*, 8:1-12 (1997).
Tang, S. et al., "Soluble Myelin-Associated Glycoprotein (MAG) Found in Vivo Inhibits Axonal Regeneration," *Molecular and Cellular Neuroscience*, 9:333-346 (1997).
Chen, M.S. et al., "Nogo-A is a Myelin-Associated Neurite Outgrowth Inhibitor and an Antigen for Monoclonal Antibody IN-1," *Nature*, 403:434-9 (2000).
DeBallard et al. "Myelin-Associated Glycoprotein Inhibits Axonal Regeneration from a Variety of Neurons Via Interaction with a Sialoglycoprotein," *Mol Cell Neurosci*, 7:89-101 (1996).
Domeniconi, M. et al., "Myelin-Associated Glycoprotein Interacts with the Nogo66 Receptor to Inhibit Neurite Outgrowth," *Neuron*, 35:283-290 (2002).
Fournier, A.E. et al., "Identification of a Receptor Mediating Nogo-66 Inhibition of Axonal Regeneration," *Nature*, 409:341-346 (2001).
Grandpre, T. et al., "Identification of the Nogo Inhibitor of Axon Regeneration as a Reticulon Protein," *Nature*, 403:439-444 (2000).
Grandpre et al., "Nogo-66 Receptor Antagonist Peptide Promotes Axonal Regeneration," *Nature*, 417:547-551 (2002).
Kelm, S. et al., Sialoadhesin, Myelin-Associated Glycoprotein and CD22 Define a New Family of Sialic Acid-Dependent Adhesion Molecules of the Immunoglobulin Superfamily, *Current Biol.*, 4:965-972 (1994).
Liu, B.P. et al., "Myelin-Associated Glycoprotein as a Functional Ligand for the Nogo-66 Receptor," *Science*, 297:1190-1193 (2002).
McKerracher, L. et al., "Identification of Myelin-Associated Glycoprotein as a Major Myelin-Derived Inhibitor of Neurite Growth," *Neuron*, 13:805-811 (1994).
Mukhopadhyay, G. et al., "A novel Role for Myelin-Associated Glycoprotein as an Inhibitor of Axonal Regeneration," *Neuron*, 13:757-767 (1994).
Schnell, L. et al., "Axonal Regeneration in the Rat Spinal Cord Produced by an Antibody Against Myelin-Associated Neurite Growth Inhibitors," *Nature*, 343:269-72 (1990).

(Continued)

*Primary Examiner*—Daniel E Kolker
(74) *Attorney, Agent, or Firm*—Fish & Richardson P.C.

(57) ABSTRACT

The present invention relates generally to products, compositions and methods useful for promoting neural repair and regeneration. The products and compositions of this invention include myelin-associated glycoprotein (MAG) derivatives that are inhibitors of endogenous MAG (e.g., mutant MAG proteins) and Nogo Receptor (NgR) binding inhibitors that are peptides derived from MAG, Nogo and OMgp that can bind to NgR and block NgR signaling. Peptides that can bind and activate NgR signaling are also provided. Inhibitory MAG derivatives and NgR binding inhibitors are useful for blocking the inhibition of neural regeneration mediated by proteins such as MAG, Nogo and/or OMgp in the nervous system. These inhibitors are also useful for treating neural degeneration associated with injuries, disorders or diseases.

18 Claims, 19 Drawing Sheets

OTHER PUBLICATIONS

Schnell, L. et al., "Neurotrophin-3 Enhances Sprouting of Corticospinal Tract During Development and After Adult Spinal Cord Lesion," *Nature*, 367:170-173 (1993).

Wang, K.C. et al., "Oligodendrocyte-Myelin Glycoprotein is a Nogo Receptor Ligand that Inhibits Neurite Outgrowth," *Nature*, 417:941-944 (2002).

Bork, P. et al., "The Immunoglobulin Fold, Structural Classification, Sequence Patterns and Common Core," *J. Mol. Biol.*, 242:309-320 (1994).

Supplementary Search Report for related application EP 03800036.0, dated Jun. 29, 2010.

Burger et al., Identification of the Glycosylated Sequors of Human Myelin-Associated Glycoprotein, Biochemical and Biophysical Research Communications, 1993, 197:457-464.

Cao et al., The Inhibition Site On Myelin-Associated Glycoprotein Is Within Ig-Domain 5 and is Distinct from the Sialic Acid Binding Site, The Journal of Neuroscience, 2007, 27:9146-9154.

Tang et al., Myelin-Associated Glycoprotein Interacts With Neurons Via a Sialic Binding Site at ARG118 and a Distinct Neurite Inhibition Site, The Journal of Cell Biology, 1997, 138:1355-1366.

Tropak et al., Regulation of Myelin-Associated Glycoprotein Binding By Sialylated Cis-Ligands, The Journal Of Neurochemistry, 1997, 68:1753-1763.

* cited by examiner

|  | neurite length | std error |
|---|---|---|
| R2 | 47.1167 | 4.8898 |
| MAG | 18.403 | 2.713 |
| control peptide | 18.2587 | 2.4482 |
| M433 | 33.4919 | 2.1793 |
| M462 | 29.7704 | 3.0927 |

FIGURE 6: RAT MAG NUCLEIC ACID SEQUENCES

```
1     cagaagccag accatccaac cttctgtatc agtgctcctc gtcgcctcac tgtacttcac
61    ggaagagact tggttgactg gccacttgga gcggaatcag gagacattcc caactcaggg
121   agactgaggt gagggcccta gctcgcccac ttgctggaca agatgatatt ccttaccacc
181   ctgcctctgt tttggataat gatttcagct tctcgagggg ggcactgggg tgcctggatg
241   ccctcgtcca tctcagcctt cgagggcacg tgtgtctcca tcccctgccg tttcgacttc
301   ccggatgagc tcagaccggc tgtggtacat ggcgtctggt atttcaacag tccctacccc
361   aagaactacc cgccagtggt cttcaagtcc cgcacacaag tggtccacga gagcttccag
421   ggccgtagcc gcctgttggg agacctgggc ctacgaaact gcaccctgct tctcagcacg
481   ctgagccctg agctgggagg gaaatactat ttccgaggtg acctgggcgg ctacaaccag
541   tacaccttct cggagcacag cgtcctggac atcatcaaca ccccccaacat cgtggtgccc
601   ccagaagtgg tggcaggaac ggaagtagag gtcagctgca tggtgccgga caactgccca
661   gagctgcgcc ctgagctgag ctggctgggc cacgaggggc tagggagcc cactgttctg
721   ggtcggctgc gggaggatga aggcacctgg gtgcaggtgt cactgctaca cttcgtgcct
781   actagagagg ccaacggcca ccgtctgggc tgtcaggctg ccttcccaa caccaccttg
841   cagttcgagg gttacgccag tctggacgtc aagtaccccc cggtgattgt ggagatgaat
901   tcctctgtgg aggccattga gggctcccat gtcagcctgc tctgtggggc tgacagcaac
961   ccgccaccgc tgctgacttg gatgcgggat gggatggtgt tgagggaggc agttgctgag
1021  agcctgtacc tggatctgga ggaggtgacc ccagcagagg acggcatcta tgcttgcctg
1081  gcagagaatg cctatggcca ggacaaccgc acggtggagc tgagcgtcat gtatgcacct
1141  tggaagccca cagtgaatgg gacggtggtg gcggtagagg gggagacagt ctccatcctg
1201  tgttccacac agagcaaccc ggaccctatt ctcaccatct tcaaggagaa gcagatcctg
1261  gccacggtca tctatgagag tcagctgcag ctggaactcc ctgcagtgac gcccgaggac
1321  gatggggagt actggtgtgt agctgagaac cagtatggcc agagagccac cgccttcaac
1381  ctgtctgtgg agtttgctcc cataatcctt ctggaatcgc actgtgcagc ggccagagac
1441  accgtgcagt gcctgtgtgt ggtaaaatcc aacccggaac cctccgtggc ctttgagctg
1501  ccttcccgca acgtgactgt gaacgagaca gagagggagt ttgtgtactc agagcgcagc
1561  ggcctcctgc tcaccagcat cctcacgctc cggggtcagg cccaagcccc accccgcgtc
1621  atttgtacct ccaggaacct ctacggcacc cagagcctcg agctgccttt ccagggagca
1681  caccgactga tgtgggccaa aatcggccct gtgggtgctg tggtcgcctt tgccatcctg
1741  attgccattg tctgctacat cacccagaca agaagaaaaa agaacgtcac agagagcccc
1801  agcttctcag cggagacaa ccctcatgtc ctgtacagcc ccgaattccg aatctctgga
1861  gcacctgata agtatgagag tgagaagcgc ctggggtccg agaggaggct gctgggcctt
1921  aggggggaac cccagaact ggacctcagt tattcccact cagacctggg gaaacgaccc
1981  accaaggaca gctacaccct gacagaggag ctggctgagt acgcagaaat ccgagtcaag
2041  tgaggaagct gggggctggc cctgtggctc accccccatc aggaccctcg cttggccccc
2101  actggccgtg ggctcccttt ctcttgagag tggtaggggt ggggcggga aggggcgggg
2161  caggaaacag tgaggtctta ggggcccggc ctcccctcct tcccggctgc tcctctctgc
2221  caacatcctg cacctatgtt acagctccct ctcccctcct tttaacctca gctgttgaga
2281  gggtgtctct gtctgtccat gttatttatt gttatcctgg tctcctgtcc ccttacccgg
2341  ccccaggacc tgtacaaaag ggacatgaaa taaatgtcct aatgacaagt gccagtctag
2401  acccatcctt tggaggaaag gggcatatta gtaatacttt tctcgttgct gtaacaaaat
2461  actggacaaa aacac
```

Immunoglobulin-like domains IgD1= 271-462, IgD2= 637-813,

IgD3= 943-1077, IgD4= 1201-1338, IgD5= 1456-1626

Transmembrane Domain TM = 1663-1764

Cytoplasmic Domain = 1765-2040

FIGURE 7: RAT MAG (PREDICTED) AMINO ACID SEQUENCES

```
  1    MIFLTTLPLF WIMISASRGG HWGAWMPSSI SAFEGTCVSI PCRFDFPDEL RPAVVHGVWY FNSPYPKNYP
 71    PVVFKSRTQV VHESFQGRSR LLGDLGLRNC TLLLSTLSPE LGGKYYFRGD LGGYNQYTFS EHSVLDIINT
141    PNIVVPPEVV AGTEVEVSCM VPDNCPELRP ELSWLGHEGL GEPTVLGRLR EDEGTWVQVS LLHFVPTREA
211    NGHRLGCQAA FPNTTLQFEG YASLDVKYPP VIVEMNSSVE AIEGSHVSLL CGADSNPPPL LTWMRDGMVL
281    REAVAESLYL DLEEVTPAED GIYACLAENA YGQDNRTVEL SVMYAPWKPT VNGTVVAVEG ETVSILCSTQ
351    SNPDPILTIF KEKQILATVI YESQLQLELP AVTPEDDGEY WCVAENQYGQ RATAFNLSVE FAPIILLESH
421    CAAARDTVQC LCVVKSNPEP SVAFELPSRN VTVNETEREF VYSERSGLLL TSILTLRGQA QAPPRVICTS
491    RNLYGTQSLE LPFQGAHRLM WAKIGPVGAV VAFAILIAIV CYITQTRRKK NVTESPSFSA GDNPHVLYSP
561    EFRISGAPDK YESEKRLGSE RRLLGLRGEP PELDLSYSHS DLGKRPTKDS YTLTEELAEY AEIRVK
```

Immunoglobulin-like domains IgD1= 41-100, IgD2= 159-217, IgD3= 261-305,

IgD4= 347-392, IgD5= 432-488

Transmembrane Domain TM = 501-534

Cytoplasmic Domain = 535-626

FIGURE 8: MURINE MAG NUCLEIC ACID SEQUENCES

```
   1    gtcagatcgt ccaaccttct gtgttagcgt tcctcagctc ctcattgcag ttccctgaag
  61    agacttggtt gaaaggccac ttcaagtgga atcaggagac atccccaact cagggagact
 121    aagccctagc tcaatcactt gctaaacaag atgatattcc tcgccaccct gccgctgttt
 181    tggataatga tttcagcttc tcgaggggc cactggggtg cctggatgcc ctcgaccatc
 241    tcagccttcg agggcacgtg tgtctccatt ccctgccgtt tcgacttccc cgatgagctc
 301    agaccggctg tggtacatgg cgtctggtat ttcaatagtc cctaccccaa gaactaccca
 361    ccggtggtct tcaagtcccg cacacaagtg gtccatgaga gtttccaggg ccgcagccgc
 421    ctattgggag acctgggcct acgaaactgt accctgcttc tcagcacact gagccccgag
 481    ctgggaggca aatactattt ccgaggcgac ctgggtggct acaaccagta caccttctcg
 541    gagcacagcg tcctggacat cgtcaacacc cccaacattg tggttccccc ggaagtggtg
 601    gcaggaacgg aagtggaggt cagttgtatg gtgccggaca actgcccaga gctgcggcca
 661    gagctgagct ggctgggcca cgagggctg ggagagccca ctgtgctggg tcggctgcgt
 721    gaggatgaag gcacctgggt gcaggtgtcg ctgctacact tcgtgcctac tagagaggcc
 781    aacggccacc gtctgggctg tcaggctgcc ttccccaaca ccaccttgca gttcgagggt
 841    tacgccagtt tggacgtcaa gtaccccca gtgattgtgg agatgaattc ctctgtggag
 901    gccattgagg gctcccatgt cagcctgctc tgtggggctg acagcaaccc gccgccgctg
 961    ctgacttgga tgcgggatgg gatggtgttg agggaggcag ttgccaagag cctctacctg
1021    gatctggagg aggtgacccc aggagaggac ggcgtctatg cttgcctagc agagaacgcc
1081    tatggccagg acaaccgcac ggtggagctg agtgtcatgt atgcaccttg gaagcccaca
1141    gtgaatggga cggtggtggc cgtagagggg gagactgtct ctatcctgtg ttccacacag
1201    agcaacccgg accccatcct taccatcttc aaggagaagc agatcctagc cacggtcatc
1261    tatgagagtc agctgcagct ggaactccct gcagtgaccc ccgaggatga tggggaatac
1321    tggtgtgtgg ctgagaacca gtatggccag agagccactg ccttcaacct gtctgtggag
1381    tttgccccca taatccttct ggagtcacac tgtgcagcgg ccagagacac cgtgcagtgt
1441    ctatgtgtgg taaaatccaa cccggaaccc tctgtggcct ttgagctgcc ttcccgcaac
1501    gtgactgtga atgagacgga gagggagttt gtgtactccg agcgcagtgg cctcctgctc
1561    accagcatcc tcacgatccg gggtcaggcc caagccccac cccgcgtcat ttgtacctcc
1621    aggaacctct atggcaccca gagcctcgag ctgccttccc agggagcaca ccgactgatg
1681    tgggccaaaa tcggtcctgt gggtgctgtg gtcgcctttg ccatcctgat tgccattgtg
1741    tgctacatca cccagacgag aagaaaaaag aatgtcacgg agagctccag cttctcaggg
1801    ggagacaacc ctcatgtcct gtacagcccc gaattcagaa tctctgggc acctgataag
1861    tatgagtcca gagaggtctc tacccgggat tgtcactgag agccccagga gagtgagaag
1921    cagcgcctgg gatctgagag gaggctgctg ggccttcggg gggaatcccc agaactggac
1981    ctcagttatt cccactcaga cctgggaaaa cgacccacca aggacagcta cccctgaca
2041    gaggagctgg ctgagtatgc agaaatccga gtcaagtgag gacgctgggg gctggccctg
2101    tggctcaccc cccatcaaga ccctcgctgg gccccactg gctgtgggct ccctttctct
2161    tgagagtagt aggggtgagg gcgggaaggg gcaggacagg aaacagtgag gtcctggggg
2221    cctggcctcc cctccttccc agctgttcct ccttgccaac attccttgcc tacattagag
2281    ctccctctc ccttcctttt aacctcagct gttgagaggg gtgctctgtc tgtccatgtt
2341    atttattgct atccctttcc tggtctcctg tcccttacct ggccccagga cctgtacaaa
2401    aagggacatg aaataaatgt cctaatgac
```

Immunoglobulin-like domains IgD1= 259-450, IgD2= 625-801, IgD3= 931-1065,

IgD4= 1189-1326, IgD5= 1444-1614

Transmembrane Domain TM= 1651-1752

Intracellular domain 1753-1896

FIGURE 9: MURINE MAG (PREDICTED) AMINO ACID SEQUENCES

```
1    MIFLATLPLF WIMISASRGG HWGAWMPSTI SAFEGTCVSI PCRFDFPDEL RPAVVHGVWY FNSPYPKNYP
71   PVVFKSRTQV VHESFQGRSR LLGDLGLRNC TLLLSTLSPE LGGKYYFRGD LGGYNQYTFS EHSVLDIVNT
141  PNIVVPPEVV AGTEVEVSCM VPDNCPELRP ELSWLGHEGL GEPTVLGRLR EDEGTWVQVS LLHFVPTREA
211  NGHRLGCQAA FPNTTLQFEG YASLDVKYPP VIVEMNSSVE AIEGSHVSLL CGADSNPPPL LTWMRDGMVL
281  REAVAKSLYL DLEEVTPGED GVYACLAENA YGQDNRTVEL SVMYAPWKPT VNGTVVAVEG ETVSILCSTQ
351  SNPDPILTIF KEKQILATVI YESQLQLELP AVTPEDDGEY WCVAENQYGQ RATAFNLSVE FAPIILLESH
421  CAAARDTVQC LCVVKSNPEP SVAFELPSRN VTVNETEREF VYSERSGLLL TSILTIRGQA QAPPRVICTS
491  RNLYGTQSLE LPFQGAHRLM WAKIGPVGAV VAFAILIAlV CYITQTRRKK NVTESSSFSG GDNPHVLYSP
561  EFRISGAPDK YESREVSTRD CH
```

Immunoglobulin-like domains IgD1= 37-100, IgD2= 159-217, IgD3= 261-305,

IgD4= 347-392, IgD5= 432-488

Transmembrane Domain TM = 501-534

Cytoplasmic Domain = 535-582

FIGURE 10: HUMAN MAG NUCLEIC ACID SEQUENCES

```
   1   ctagaccctg gaaggcaggg gactgcgagc tgggctggcg gagcagaggt gcagaagcaa
  61   ctgagtccaa gttgtctggc ggcttcaggt ggacccagaa gacgtcccca actcagggag
 121   attcagcgat cactcactcg ctgtacagaa tgatattcct cacggcactg cctctgttct
 181   ggattatgat ttcagcctcc cgaggggtc actggggtgc ctggatgccc tcgtccatct
 241   cggccttcga aggcacgtgc gtctccatcc cctgccgctt tgacttcccg gatgagctgc
 301   ggcccgctgt ggtgcatggt gtctggtact tcaatagccc ctaccccaag aactacccc
 361   cggtggtctt caagtcgcgc acccaagtag tccacgagag cttccagggc cgcagccgcc
 421   tcctggggga cctgggcctg cgaaactgca ccctcctgct cagcaacgtc agccccgagc
 481   tgggcgggaa gtactacttc cgtggggacc tgggcggcta caaccagtac accttctcag
 541   agcacagcgt cctggatatc gtcaacaccc ccaacatcgt ggtgccccca gaggtggtgg
 601   caggcacgga ggtggaggtc agctgcatgg tgccggacaa ctgcccagag ctgcgccctg
 661   agctgagctg gctgggccac gaggggctgg gggagcccgc tgtgctgggc cggctgcggg
 721   aggacgaggg cacctgggtg caggtgtcac tgctgcactt cgtgcccacg agggaggcca
 781   acggccacag gctgggctgc caggcctcct tcccaacac caccctgcag ttcgagggct
 841   acgccagcat ggacgtcaag tacccccgg tgattgtgga gatgaactcc tcggtggagg
 901   ccatcgaggg ctcccacgtg agcctgctct gtggggctga cagcaacccc ccgccgctgc
 961   tgacctggat gcgggacggg acagtcctcc gggaggcggt ggccgagagc ctgctcctgg
1021   agctggagga ggtgacccc gccgaagacg gcgtctatgc ctgcctggcc gagaatgcct
1081   atggccagga caaccgcacc gtggggctca gtgtcatgta tgcaccctgg aagccaacag
1141   tgaacgggac aatggtggcc gtagagggg agacgtctc tatcttgtgc tccacacaga
1201   gcaacccgga ccctattctc accatcttca aggagaagca gatcctgtcc acggtcatct
1261   acgagagcga gctgcagctg gagctgccgg ccgtgtcacc cgaggatgat ggagagtact
1321   ggtgtgtggc tgagaaccag tatggccaga gggccaccgc cttcaacctg tctgtggagt
1381   tcgcccctgt gctcctcctg gagtcccact gcgcggcagc ccgagacacg gtgcagtgcc
1441   tgtgcgtggt gaagtccaac ccggagccgt ccgtggcctt tgagctgcca tcgcgcaatg
1501   tgaccgtgaa cgagagcgag cgggagttcg tgtactcgga gcgcagcggc ctcgtgctca
1561   ccagcatcct cacgctgcgg gggcaggccc aggccccgcc ccgcgtcatc tgcaccgcga
1621   ggaacctcta tgcgccaag agcctggagc tgcccttcca gggagcccat cgactgatgt
1681   gggccaagat cgggcctgtg gcgccgtgg tcgcctttgc catcctgatt gccatcgtct
1741   gctacattac ccagacacgc aggaaaaaga acgtgacaga gagcccagc ttctcggcag
1801   gggacaaccc tcccgtcctg ttcagcagcg acttccgcat ctctggggca ccagagaagt
1861   acgagagcga gaggcgcctg ggatctgaga ggaggctgct gggccttcgg ggtgagcccc
1921   cagagctgga cctgagctat tctcactcgg acctggggaa acggcccacc aaggacagct
1981   acacgctgac ggaggagcta gctgagtatg ctgaaatccg ggtcaagtga aggagctggg
2041   ggcagcctgc gtggctgacc ccctcagga ccctcgctgg ccccactgg ctgtgggctc
2101   ccttcctccc aaaagtatcg ggggctgggg caggaggga gtgaggcagg tgacagtgag
2161   gtcctggggg cctgacctcc ccctccttcc cagctgcccc tcctgccag cacccccacg
2221   ccctcattac ggctcctctc taacctcctt taccctcatc tgtctggagg ggagctctgt
2281   ctgtccgtgt tatttattgc tacttcctgc ctggtctcct gccccacac ctggccctgg
2341   ggcctgtaca aagggacat gaaataaatg ccccaaagcc
```

Immunoglobulin-like domains IgD1= <u>258-449</u>, IgD2= <u>624-800</u>, IgD3= <u>930-1064</u>, IgD4= <u>1188-1325</u>, IgD5= <u>1443-1613</u>

Transmembrane Domain TM= <u>1650-1751</u>

Cytoplasmic domain 1752-2027

FIGURE 11: HUMAN MAG (PREDICTED) AMINO ACID SEQUENCES

```
  1    MIFLTALPLF WIMISASRGG HWGAWMPSSI SAFEGTCVSI PCRFDFPDEL RPAVVHGVWY FNSPYPKNYP
 71    PVVFKSRTQV VHESFQGRSR LLGDLGLRNC TLLLSNVSPE LGGKYYFRGD LGGYNQYTFS EHSVLDIVNT
141    PNIVVPPEVV AGTEVEVSCM VPDNCPELRP ELSWLGHEGL GEPAVLGRLR EDEGTWVQVS LLHFVPTREA
211    NGHRLGCQAS FPNTTLQFEG YASMDVKYPP VIVEMNSSVE AIEGSHVSLL CGADSNPPPL LTWMRDGTVL
281    REAVAESLLL ELEEVTPAED GVYACLAENA YGQDNRTVGL SVMYAPWKPT VNGTMVAVEG ETVSILCSTQ
351    SNPDPILTIF KEKQILSTVI YESELQLELP AVSPEDDGEY WCVAENQYGQ RATAFNLSVE FAPVLLLESH
421    CAAARDTVQC LCVVKSNPEP SVAFELPSRN VTVNESEREF VYSERSGLVL TSILTLRGQA QAPPRVICTA
491    RNLYGAKSLE LPFQGAHRLM WAKIGPVGAV VAFAILIAIV CYITQTRRKK NVTESPSFSA GDNPPVLFSS
561    DFRISGAPEK YESERRLGSE RRLLGLRGEP PELDLSYSHS DLGKRPTKDS YTLTEELAEY AEIRVK
```

Immunoglobulin-like domains IgD1= 42-100, IgD2= 159-217, IgD3= 261-305,

IgD4= 347-392, IgD5= 432-488

Transmembrane Domain TM = 501-534

Cytoplasmic Domain = 535-582

FIGURE 12: HUMAN NOGO-A NUCLEIC ACID SEQUENCES (cDNA)

```
   1 atggaagacc tggaccagtc tcctctggtc tcgtcctcgg acagcccacc ccggccgcag
  61 cccgcgttca agtaccagtt cgtgagggag cccgaggacg aggaggaaga agaggaggag
 121 gaagaggagg acgaggacga agacctggag gagctggagg tgctggagag gaagcccgcc
 181 gccgggctgt ccgcggcccc agtgcccacc gcccctgccg ccggcgcgcc cctgatggac
 241 ttcggaaatg acttcgtgcc gccggcgccc cggggacccc tgccggccgc tcccccgtc
 301 gccccggagc ggcagccgtc ttgggacccg agcccggtgt cgtcgaccgt gcccgcgcca
 361 tccccgctgt ctgctgccgc agtctcgccc tccaagctcc ctgaggacga cgagcctccg
 421 gcccggcctc cccctcctcc cccggccagc gtgagccccc aggcagagcc cgtgtggacc
 481 ccgccagccc cggctcccgc cgcgccccc tccaccccgg ccgcgcccaa cgcaggggc
 541 tcctcgggct cagtggatga gaccctttt gctcttcctg ctgcatctga gcctgtgata
 601 cgctcctctg cagaaaatat ggacttgaag gagcagccag gtaacactat tcggctggt
 661 caagaggatt tcccatctgt cctgcttgaa actgctgctt ctcttccttc tctgtctcct
 721 ctctcagccg cttctttcaa agaacatgaa taccttggta atttgtcaac agtattaccc
 781 actgaaggaa cacttcaaga aatgtcagt gaagcttcta aagaggtctc agagaaggca
 841 aaaactctac tcatagatag agatttaaca gagttttcag aattagaata ctcagaaatg
 901 ggatcatcgt tcagtgtctc tccaaaagca gaatctgccg taatagtagc aaatcctagg
 961 gaagaaataa tcgtgaaaaa taaagatgaa gagagaagt tagttagtaa taacatcctt
1021 cataatcaac aagagttacc tacagctctt actaaattgg ttaaagagga tgaagttgtg
1081 tcttcagaaa agcaaaaga cagtttaat gaaagagag ttgcagtgga agctcctatg
1141 agggaggaat atgcagactt caaaccattt gagcgagtat gggaagtgaa agatagtaag
1201 gaagatagtg atatgttggc tgctggaggt aaaatcgaga gcaacttgga aagtaaagtg
1261 gataaaaaat gttttgcaga tagccttgag caaactaatc acgaaaaaga tagtgagagt
1321 agtaatgatg atacttcttt ccccagtacg ccagaaggta taaggatcg tccaggagca
1381 tatatcacat gtgctccctt taacccagca gcaactgaga gcattgcaac aaacatttt
1441 cctttgttag gagatcctac ttcagaaaat aagaccgatg aaaaaaaat agaagaaag
1501 aaggcccaaa tagtaacaga gaagaatact agcaccaaaa catcaaaccc ttttcttgta
1561 gcagcacagg attctgagac agattatgtc acaacagata atttaacaaa ggtgactgag
1621 gaagtcgtgg caaacatgcc tgaaggcctg actccagatt tagtacagga agcatgtgaa
1681 agtgaattga atgaagttac tggtacaaag attgcttatg aaacaaaaat ggacttggtt
1741 caaacatcag aagttatgca agagtcactc tatcctgcag cacagctttg cccatcattt
1801 gaagagtcag aagctactcc ttcaccagtt ttgcctgaca ttgttatgga agcaccattg
1861 aattctgcag ttcctagtgc tggtgcttcc gtgatacagc ccagctcatc accattagaa
1921 gcttcttcag ttaattatga aagcataaaa catgagcctg aaaacccccc accatatgaa
1981 gaggccatga gtgtatcact aaaaaaagta tcaggaataa aggaagaaat taagagcct
2041 gaaaatatta atgcagctct tcaagaaaca gaagctcctt atatatctat tgcatgtgat
2101 ttaattaaag aaacaaagct ttctgctgaa ccagctccgg atttctctga ttattcagaa
2161 atggcaaaag ttgaacagcc agtgcctgat cattctgagc tagttgaaga ttcctcacct
2221 gattctgaac cagttgactt atttagtgat gattcaatac ctgacgttcc acaaaaacaa
2281 gatgaaactg tgatgcttgt gaaagaaagt ctcactgaga cttcatttga gtcaatgata
2341 gaatatgaaa ataaggaaaa actcagtgct tgccacctg agggaggaaa gccatatttg
2401 gaatctttta agctcagttt agataacaca aaagataccc tgttacctga tgaagtttca
2461 acattgagca aaaggagaa aattccttg cagatggagg agctcagtac tgcagtttat
2521 tcaaatgatg acttatttat ttctaaggaa gcacagataa gagaactga aacgttttca
2581 gattcatctc caattgaaat tatgatgag ttccctacat tgatcagttc taaaactgat
2641 tcatttttcta aattagccag ggaatatact gacctagaag tatcccacaa aagtgaaatt
2701 gctaatgccc cggatggagc tgggtcattg ccttgcacag aattgcccca tgacctttct
2761 ttgaagaaca tacaacccaa agttgaagag aaaatcagtt ctctcagatga cttttctaaa
2821 aatgggtctg ctacatcaaa ggtgctctta ttgcctccag atgtttctgc tttggccact
2881 caagcagaga tagagagcat agttaaaccc aaagttcttg tgaaagaagc tgagaaaaaa
2941 cttccttccg atacagaaaa agaggacaga tcaccatctg ctatatttc agcagagctg
3001 agtaaaactt cagttgttga cctcctgtac tggagagaca ttaagaagac tggagtggtg
3061 tttggtgcca gctattcct gctgctttca ttgacagtat tcagcattgt gagcgtaaca
3121 gcctacattg ccttggcct gctctctgtg accatcagct ttaggatata caagggtgtg
3181 atccaagcta tccagaaatc agatgaaggc cacccattca gggcatatct ggaatctgaa
3241 gttgctatat ctgaggagtt ggttcagaag tacagtaatt ctgctcttgg tcatgtgaac
3301 tgcacgataa aggaactcag gcgcctcttc ttagttgatg atttagttga ttctctgaag
3361 tttgcagtgt tgatgtgggt atttacctat gttggtgcct tgtttaatgg tctgacacta
3421 ctgattttgg ctctcatttc actcttcagt gttcctgtta tttatgaacg gcatcaggcg
3481 cagatagatc attatctagg acttgcaaat aagaatgtta agatgctat ggctaaaatc
3541 caagcaaaaa tccctggatt gaagcgcaaa gctgaatga
```

```
FIGURE 13:  HUMAN NOGO-A (PREDICTED) AMINO ACID SEQUENCES
human Nogo-A
ACCESSION   AAM64244
     AUTHORS   Oertle,T., van der Putten,H. and Schwab,M.E.

1 MEDLDQSPLV SSSDSPPRPQ PAFKYQFVRE PEDEEEEEEE EEEDEDEDLE ELEVLERKPA
       61 AGLSAAPVPT APAAGAPLMD FGNDFVPPAP RGPLPAAPPV APERQPSWDP SPVSSTVPAP
      121 SPLSAAAVSP SKLPEDDEPP ARPPPPPPAS VSPQAEPVWT PPAPAPAAPP STPAAPKRRG
      181 SSGSVDETLF ALPAASEPVI RSSAENMDLK EQPGNTISAG QEDFPSVLLE TAASLPSLSP
      241 LSAASFKEHE YLGNLSTVLP TEGTLQENVS EASKEVSEKA KTLLIDRDLT EFSELEYSEM
      301 GSSFSVSPKA ESAVIVANPR EEIIVKNKDE EEKLVSNNIL HNQQELPTAL TKLVKEDEVV
      361 SSEKAKDSFN EKRVAVEAPM REEYADFKPF ERVWEVKDSK EDSDMLAAGG KIESNLESKV
      421 DKKCFADSLE QTNHEKDSES SNDDTSFPST PEGIKDRPGA YITCAPFNPA ATESIATNIF
      481 PLLGDPTSEN KTDEKKIEEK KAQIVTEKNT STKTSNPFLV AAQDSETDYV TTDNLTKVTE
      541 EVVANMPEGL TPDLVQEACE SELNEVTGTK IAYETKMDLV QTSEVMQESL YPAAQLCPSF
      601 EESEATPSPV LPDIVMEAPL NSAVPSAGAS VIQPSSSPLE ASSVNYESIK HEPENPPPYE
      661 EAMSVSLKKV SGIKEEIKEP ENINAALQET EAPYISIACD LIKETKLSAE PAPDFSDYSE
      721 MAKVEQPVPD HSELVEDSSP DSEPVDLFSD DSIPDVPQKQ DETVMLVKES LTETSFESMI
      781 EYENKEKLSA LPPEGGKPYL ESFKLSLDNT KDTLLPDEVS TLSKKEKIPL QMEELSTAVY
      841 SNDDLFISKE AQIRETETFS DSSPIEIIDE FPTLISSKTD SFSKLAREYT DLEVSHKSEI
      901 ANAPDGAGSL PCTELPHDLS LKNIQPKVEE KISFSDDFSK NGSATSKVLL LPPDVSALAT
      961 QAEIESIVKP KVLVKEAEKK LPSDTEKEDR SPSAIFSAEL SKTSVVDLLY WRDIKKTGVV
     1021 FGASLFLLLS LTVFSIVSVT AYIALALLSV TISFRIYKGV IQAIQKSDEG HPFRAYLESE
     1081 VAISEELVQK YSNSALGHVN CTIKELRRLF LVDDLVDSLK FAVLMWVFTY VGALFNGLTL
     1141 LILALISLFS VPVIYERHQA QIDHYLGLAN KNVKDAMAKI QAKIPGLKRK AE
```

Nogo-66 amino acid sequences underlined

FIGURE 14: MURINE OMGP NUCLEIC ACID SEQUENCES

```
1    ctgagctggc aagcagagcc cacagccaga aacccttccg actcccacaa caagacgacc
61   tttaagctgc aagtttcccg gagaaaatga gatactgata gtgaagacga cattatgggc
121  tttgatggaa tatcagatac tgaaaatgtc ttcctgcctg ttcatccttc tgtttctcac
181  gcctggcatc ttatgcattt gtcctctcca gtgtacatgc acagagaggc acaggcatgt
241  ggactgttca ggcagaaact tgactacatt accacctgga ctgcaggaga acattataca
301  tttaaacctg tcttataacc actttactga tctgcataac cagttaaccc catataccaa
361  tctgagaacc ctggatattt caaacaacag gcttgaaagt ctgcctgctc agttacctcg
421  gtctctctgg aacatgtctg ctgctaacaa caatattaaa cttcttgaca aatctgatac
481  tgcttatcag tggaacctta aatacctgga tgtttctaag aatatgctgg aaaaggttgt
541  tctcattaaa aatacectaa gaagtctcga ggttcttaac ctcagcagta acaagctttg
601  gacagttcca accaacatgc cttccaaact gcatatcgtg gacctgtcta ataactcact
661  gacacaaatc cttccaggga cattaataaa cctgacaaat ctcacacatc tttacctgca
721  caacaataaa ttcacattca ttccagaaca gtcttttgac caacttttgc agttgcaaga
781  gataactctt cataataaca ggtggtcatg tgaccataaa caaaacatta cttacttatt
841  gaagtgggtg atggaaacga agcccatgt gatagggact ccttgttcta agcaagtatc
901  ctctctaaag gaacagagca tgtaccccac acctcctggg tttacctcaa gcttatttac
961  tatgagtgag atgcagacag tggacaccat taactctttg agtatggtaa ctcaacccaa
1021 agtgaccaaa acacccaaac aatatcgagg aaaggaaacc acatttggtg tcactctaag
1081 caaagatacc acttttagta gcactgatag ggctgtggtg gcctacccag aagacacacc
1141 cacagaaatg accaattccc atgaagcagc agctgcaact ctaactattc acctccagga
1201 tggaatgagt tcaaatgcaa gcctcaccag tgcaacaaag tcaccccaa gccccgtgac
1261 cctcagcata gctcgtggca tgccaaataa cttctctgaa atgcctcgac aaagcacaac
1321 cctcaactta cggagggaag aaaccactgc aaatggaaac actcggccac cttctgcggc
1381 tagtgcttgg aaagtaaatg cctcgctcct tttaatgctc aatgctgtgg tcatgctggc
1441 aggctgaggg tctgcagttt ctgaaacgaa ggagaacctt cctccatgat gtacagttgg
1501 gaaaacgtgc ccctatctaa ccagtgattc aagctatatt atgtattcaa gaaagccagt
1561 cttatatttc tgactttgat gtaaatgaag taatttgtct taattaaaag aagtgcacaa
1621 tgtcttggta cttgctgcta ttttcctgtc ttaagtaaaa ctaatgactt ttttttttaa
1681 tgaaatgttt tcttttaag gcttcaactt attgcacaaa ctataaagag catctaaact
1741 ttaatatgta ttttatgtat gtttacactg tcaaatgtct gggacaaaat aaaa
```

FIGURE 15: MURINE OMGP (PREDICTED) AMINO ACID SEQUENCES

```
  1  MEYQILKMSS  CLFILLFLTP  GILCICPLQC  TCTERHRHVD  CSGRNLTTLP  PGLQENIIHL
 61  NLSYNHFTDL  HNQLTPYTNL  RTLDISNNRL  ESLPAQLPRS  LWNMSAANNN  IKLLDKSDTA
121  YQWNLKYLDV  SKNMLEKVVL  IKNTLRSLEV  LNLSSNKLWT  VPTNMPSKLH  IVDLSNNSLT
181  QILPGTLINL  TNLTHLYLHN  NKFTFIPEQS  FDQLLQLQEI  TLHNNRWSCD  HKQNITYLLK
241  WVMETKAHVI  GTPCSKQVSS  LKEQSMYPTP  PGFTSSLFTM  SEMQTVDTIN  SLSMVTQPKV
301  TKTPKQYRGK  ETTFGVTLSK  DTTFSSTDRA  VVAYPEDTPT  EMTNSHEAAA  ATLTIHLQDG
361  MSSNASLTSA  TKSPPSPVTL  SIARGMPNNF  SEMPRQSTTL  NLRREETTAN  GNTRPPSAAS
421  AWKVNASLLL  MLNAVVMLAG
```

FIGURE 16: MAP OF MAG DERIVED PEPTIDES

MAG Derived Peptides: M343, M394, M442

```
1     MIFLTTLPLF WIMISASRGG HWGAWMPSSI SAFEGTCVSI PCRFDFPDEL RPAVVHGVWY FNSPYPKNYP
71    PVVFKSRTQV VHESFQGRSR LLGDLGLRNC TLLLSTLSPE LGGKYYFRGD LGGYNQYTFS EHSVLDIINT
141   PNIVVPPEVV AGTEVEVSCM VPDNCPELRP ELSWLGHEGL GEPTVLGRLR EDEGTWVQVS LLHFVPTREA
211   NGHRLGCQAA FPNTTLQFEG YASLDVKYPP VIVEMNSSVE AIEGSHVSLL CGADSNPPPL LTWMRDGMVL
281   REAVAESLYL DLEEVTPAED GIYACLAENA YGQDNRTVEL SVMYAPWKPT VNGTVVAVEG ETVSILCSTQ
351   SNPDPILTIF KEKQILATVI YESQLQLELP AVTPEDDGEY WCVAENQYGQ RATAFNLSVE FAPIILLESH
421   CAAARDTVQC LCVVKSNPEP SVAFELPSRN VTVNETEREF VYSERSGLLL TSILTLRGQA QAPPRVICTS
Consensus        NxIxxxPEx SxxxxLxxxE VTIxExxxxx xHxxxIGHLL SSILELRAxx IaxPxVxxLS
491   RNLYGTQSLE LPFQGAHRLM WAKIGPVGAV VAFAILIAIV CYITQTRRKK NVTESPSFSA GDNPHVLYSP
561   EFRISGAPDK YESEKRLGSE RRLLGLRGEP PELDLSYSHS DLGKRPTKDS YTLTEELAEY AEIRVK
```

MAG Derived Peptides: M363, M422, M461, Short Effective

```
1     MIFLTTLPLF WIMISASRGG HWGAWMPSSI SAFEGTCVSI PCRFDFPDEL RPAVVHGVWY FNSPYPKNYP
71    PVVFKSRTQV VHESFQGRSR LLGDLGLRNC TLLLSTLSPE LGGKYYFRGD LGGYNQYTFS EHSVLDIINT
141   PNIVVPPEVV AGTEVEVSCM VPDNCPELRP ELSWLGHEGL GEPTVLGRLR EDEGTWVQVS LLHFVPTREA
211   NGHRLGCQAA FPNTTLQFEG YASLDVKYPP VIVEMNSSVE AIEGSHVSLL CGADSNPPPL LTWMRDGMVL
281   REAVAESLYL DLEEVTPAED GIYACLAENA YGQDNRTVEL SVMYAPWKPT VNGTVVAVEG ETVSILCSTQ
351   SNPDPILTIF KEKQILATVI YESQLQLELP AVTPEDDGEY WCVAENQYGQ RATAFNLSVE FAPIILLESH
421   CAAARDTVQC LCVVKSNPEP SVAFELPSRN VTVNETEREF VYSERSGLLL TSILTLRGQA QAPPRVICTS
Consensus        NxIxxxPEx SxxxxLxxxE VTIxExxxxx xHxxxIGHLL SSILELRAxx IaxPxVxxLS
491   RNLYGTQSLE LPFQGAHRLM WAKIGPVGAV VAFAILIAIV CYITQTRRKK NVTESPSFSA GDNPHVLYSP
561   EFRISGAPDK YESEKRLGSE RRLLGLRGEP PELDLSYSHS DLGKRPTKDS YTLTEELAEY AEIRVK
```

FIGURE 17:   NgR LIGAND SEQUENCE COMPARISON

The consensus sequence was found by analysis of OMgp full length, MAG Ig-like domain 5
(MAG_d5) and Nogo66 using AlignX (component of Vector NTI Suite 8.0) by InforMax, Inc.

```
              1                                                    50
Nogo66        ..........  ..........  ..........  ..........  ..........
MAG_d5        ..........  ..........  ..........  ..........  ..........
   OMgp       MEYQILKMSS  CLFILLFLTP  GILCICPLQC  TCTERHRHVD  CSGRNLTTLP 51                                                   100
Nogo66        ..........  ..........  ..........  ..........  ..........
MAG_d5        ..........  ..........  ..........  ..........  ..........
   OMgp       PGLQENIIHL  NLSYNHFTDL  HNQLTPYTNL  RTLDISNNRL  ESLPAQLPRS 101                                                  150
Nogo66        ..........  ..........  ..........  ..........  ..........
MAG_d5        ..........  ..........  ..........  ..........  ..........
   OMgp       LWNMSAANNN  IKLLDKSDTA  YQWNLKYLDV  SKNMLEKVVL  IKNTLRSLEV 151                                                  200
Nogo66        ..........  ..........  ..........  ..........  ...RIYKGVI
MAG_d5        ..........  ..........  ..........  ..........  ..........
   OMgp       LNLSSNKLWT  VPTNMPSKLH  IVDLSNNSLT  QILPGTLINL  TNLTHLYLHN 201                                                  250
Nogo66        QAIQKSDEGH  PFRAYLESEV  AISEELVQKY  SNSALGHVNS  TIKELRRLFL
MAG_d5        CVVKSNPEPS  VAFELPSRNV  TVNETEREFV  YSERSGLLLT  SILTLRGQAQ
   OMgp       NKFTFIPEQS  FDQLLQLQEI  TLHNNRWSCD  HKQNITYLLK  WVMETKAHVI Consensus     N I   PE S      L     EV TI E       H   IGHLLS  SILELRA  I 251                                                  300
Nogo66        VDDLVDSLK.  ..........  ..........  ..........  ..........
MAG_d5        APPRVICTSR  NL........  ..........  ..........  ..........
   OMgp       GTPCSKQVSS  LKEQSMYPTP  PGFTSSLFTM  SEMQTVDTIN  SLSMVTQPKV Consensus     A P V  LS 301                                                  350
Nogo66        ..........  ..........  ..........  ..........  ..........
MAG_d5        ..........  ..........  ..........  ..........  ..........
   OMgp       TKTPKQYRGK  ETTFGVTLSK  DTTFSSTDRA  VVAYPEDTPT  EMTNSHEAAA 351                                                  400
Nogo66        ..........  ..........  ..........  ..........  ..........
MAG_d5        ..........  ..........  ..........  ..........  ..........
   OMgp       ATLTIHLQDG  MSSNASLTSA  TKSPPSPVTL  SIARGMPNNF  SEMPRQSTTL 401                                 440
Nogo66        ..........  ..........  ..........  ..........
MAG_d5        ..........  ..........  ..........  ..........
   OMgp       NLRREETTAN  GNTRPPSAAS  AWKVNASLLL  MLNAVVMLAG
```

FIGURE 18:   NgR Ligand Consensus Sequence

MAG 432-490 (with identified variables)

```
432                                                                  490
  NxIxxxPExSxxxxLxxxEVTIxExxxxxxxHxxxIGHLLSSILELRAxxIAxPxVxxLS
   Q V   D  H    Y   NIAL N      S   STLVNTTVKTTKR  LV D S  TK
            C F                  V            Y    L Y  KW M
   G  QG      V
```

Alternative Writing Scheme:

```
432                         450                455                465
(NQC)x(IVF)xxx(PD)Ex(SH)xxxx(LY)xxx(EN)(VI)(TA)(ILV)x(EN)xxxxxx(HSY)xxx 466                                       478           483
(ISL)(GT)(HLY)(LV)(LN)(STK)(STW)(IV)(LKM)(ET)(LT)(RK)(ARG)xx(ILQ)(AVG)x 484           490
(PD)x(VS)xx(LTV)(SK)
```

FIGURE 19: NgR Ligand Derived Peptides

| Name NO: | Sequence | Function | SEQ ID |
|---|---|---|---|
| M437 | NPEPS | Block | 17 |
| M446 | LPSRNVTVNE | Block | 18 |
| M450 | NVTVNE | Block | 19 |
| M433 | VVKSNPEPSVAFELPSRNVTVNETE | Block | 20 |
| M466 | SGLLLT | Block? | 21 |
| M472 | SILTLR | Block? | 22 |
| | | | |
| N13 | SDEGH | Block | 25 |
| N22-1 | YLESEVAISE | Block | 26 |
| N26-1 | EVAISE | Block | 28 |
| N9-1 | AIQKSDEGHPFRAYLESEVAISEEL | Block | 30 |
| N42 | LGHVNC | Block? | 33 |
| N48 | TIKELR | Block? | 34 |
| | | | |
| O206 | IPEQS | Block | 35 |
| O215 | LQLQEITLHN | Block | 36 |
| O219 | EITLHN | Block | 37 |
| O202 | KFTFIPEQSFDQLLQLQEITLHNNR | Block | 38 |
| O235 | ITYLLK | Block? | 40 |
| | | | |
| M462 | YSERSGLLLTSILTLRGQAQAPPRV | Block | 24 |
| N38 | SNSALGHVNSTIKELRRLFLVDDLV | Block | 32 |
| O231 | HKQNITYLLKWVMETKAHVIGTPCS | Block | 39 |

*Notes*

- Block means Block Inhibition of Neurite Outgrowth by MAG/Myelin
- Inhibit means Activates NgR Inhibitory Cascade (Mimics MAG/Myelin)
- Block? means an Inhibitory Region Peptide which may be too short to trigger NgR and which is thus predicted to block.
- Numbering based on amino acid position in FL-MAG, FL-OMgp or Nogo-66 ary system does not regenerate after injury despite the fact that there are many molecules present which encourage/promote axonal (nerve) growth. There are at least three factors that are responsible for this lack of regeneration: the formation of a glial scar, the presence of inhibitors of regeneration in myelin, and the intrinsic growth capacity of adult axons. In situations involving injury, the glial scar takes some time after injury to form. It would be advantageous to encourage axonal growth during this "window-of-opportunity", before the scar forms. It would also be desirable to be able to encourage axonal growth irrespective of scarring, e.g., for treating or preventing neural degeneration or damage associated with a disorder, disease or condition. Blocking the function of the inhibitors of regeneration present in myelin can be achieved by, e.g., neutralizing the inhibitors or altering the growth capacity of the axon so that it no longer responds to the inhibitors.

INHIBITORS OF MYELIN-ASSOCIATED GLYCOPROTEIN (MAG) ACTIVITY FOR REGULATING NEURAL GROWTH AND REGENERATION

TECHNICAL FIELD OF THE INVENTION

This invention relates to inhibitors of myelin-associated glycoprotein (MAG) activity, such as MAG derivatives and Nogo receptor (NgR) ligand blocking peptides, and compositions and methods comprising such derivatives and peptides, useful for regulating neural growth and regeneration.

BACKGROUND OF THE INVENTION

The mammalian nervous system does not regenerate after injury despite the fact that there are many molecules present which encourage/promote axonal (nerve) growth. There are at least three factors that are responsible for this lack of regeneration: the formation of a glial scar, the presence of inhibitors of regeneration in myelin, and the intrinsic growth capacity of adult axons. In situations involving injury, the glial scar takes some time after injury to form. It would be advantageous to encourage axonal growth during this "window-of-opportunity", before the scar forms. It would also be desirable to be able to encourage axonal growth irrespective of scarring, e.g., for treating or preventing neural degeneration or damage associated with a disorder, disease or condition. Blocking the function of the inhibitors of regeneration present in myelin can be achieved by, e.g., neutralizing the inhibitors or altering the growth capacity of the axon so that it no longer responds to the inhibitors.

To date, three inhibitors have been identified in myelin: myelin-associated glycoprotein (MAG) (McKerracher, L. et al., *Neuron*, 13, pp. 805-811 (1994); Mukhopadhyay, G. et al., *Neuron*, 13, pp. 757-767 (1994); U.S. Pat. No. 5,932,542; U.S. Pat. No. 6,203,792; and U.S. Pat. No. 6,399,577; and WO 97/01352), Nogo (Chen, M. S. et al., *Nature*, 403, pp. 434-439 (2000); Grandpre, T. et al., *Nature*, 403, pp. 439-444 (2000)); and oligodendrocyte myelin glycoprotein (OMgp) (Wang, K. C. et al., *Nature*, 417, pp. 941-944 (2002). Interestingly, all three of these inhibitors bind to the same receptor to exert their inhibitory effects (Wang et al., supra; Domeniconi, M. et al., *Neuron*, 35, pp. 283-290 (2002); Fournier, A. E. et al., *Nature*, 409, pp. 341-346 (2001); Liu, B. P. et al., *Science*, 297, pp. 1190-1193 (2002)). Because this receptor was first identified as being a receptor for Nogo-66 ligand (a 66 amino acid extracellular domain shared by different isoforms of Nogo), it is referred to as the Nogo-66 receptor ("NgR")(Fournier, A. E. et al., supra).

One way to neutralize an inhibitor of neural growth and regeneration is to interfere with its ability to bind to or to activate signaling by its cognate receptor. Hence, it would be useful to design molecules capable of interfering with the ability of endogenous MAG to bind to or to activate NgR. MAG derivatives, for example, which can compete with endogenous MAG for neuron binding but which cannot bind to or activate signaling by NgR would be desirable.

Our previous studies demonstrated that the ability of MAG to inhibit neurite outgrowth is distinct from its ability to bind to neurons. (See e.g., U.S. Pat. Nos. 5,932,542; 6,203,792; and 6,399,577). These studies identified one such desirable inhibitor, MAG(d1-3)-Fc, and showed that sequences in the fourth and fifth Ig-like domains or the junction between the third and fourth Ig-like domains of MAG are responsible for MAG's ability to inhibit neurite outgrowth. It would be useful to identify other molecules that can block the inhibitory effects of myelin on neural growth and regeneration.

It appears that there is overlap in the binding sites on NgR for the three ligands (MAG, Nogo-66 and OMgp) (Domeniconi et al., supra; Liu et al., supra; Wang et al. supra) as binding of one ligand is able to compete with and thus reduce binding of other ligands (Domeniconi et al., supra; Wang et al. supra). Thus, if a ligand binding site on NgR were to be blocked, the inhibitory effects of all three of the inhibitors found in myelin would likely be blocked. Furthermore, it is likely that peptide fragments derived from any one NgR ligand would block the ability of any or all of these inhibitors to bind to and activate NgR. Because these are the only inhibitors in myelin identified to date, blocking the ability of these ligands to bind to NgR and thus blocking the downstream effects of NgR signaling will likely prevent the majority, if not all, of the inhibitory effects of myelin on neural growth and regeneration.

SUMMARY OF THE INVENTION

The present invention provides inhibitory molecules that reduce or eliminate the ability of endogenous inhibitors present in myelin, e.g., MAG, Nogo and OMgp, to regulate (e.g., to promote or inhibit) neurite outgrowth. Preferably, inhibitory molecules of the invention disrupt the ability of endogenous inhibitors, such as those present in myelin, to bind to or activate signaling by Nogo receptor (NgR), thereby promoting neural growth and regeneration.

In one embodiment, an inhibitory molecule of the invention is derived from a MAG molecule having at least one mutation in Ig-like domain 5 (Igd5) or in a region flanking (i.e., within 10 amino acid residues on either side of) Igd5, wherein the mutation reduces or eliminates the ability of the derivative to regulate (e.g., inhibit or promote) neurite outgrowth compared to endogenous or soluble MAG without eliminating binding to neuronal surfaces. Preferably, the mutation in MAG Ig-like domain 5 reduces or eliminates its ability to activate signaling of the Nogo receptor (NgR) compared to endogenous or soluble MAG.

In one preferred embodiment, the mutation in MAG is a partial or total deletion of Ig-like domain 5 ("Igd5") (and/or sequences flanking Igd5, see supra). Preferred MAG deletion mutations are provided. In another preferred embodiment, the mutation in MAG is a point mutation in or flanking MAG Igd5. Preferred inhibitors of this embodiment are provided.

In a preferred embodiment, inhibitory MAG derivatives of the invention are chimeric, and more preferably, are soluble chimeric molecules comprising at least one extracellular domain of MAG, preferably Ig-like domain 1 of MAG (which carries a sialic acid binding site), and further comprising at least one mutation in or flanking MAG Ig-like domain 5. Preferred chimeric MAG derivatives replace the transmembrane and intracellular domains of MAG with a soluble domain, e.g., with an immunoglobulin Fc region ("Ig-Fc"). Other preferred soluble MAG derivatives comprises at least one extracellular domain from a heterologous protein, e.g., an Ig-like domain from a sialoadhesin molecule or another neuron binding molecule (such as Nogo or OMgp).

In another embodiment of the invention, an inhibitory molecule comprises a peptide derived from amino acid residues that make up a Nogo receptor ligand binding site ("NgR binding inhibitor"). Preferred NgR binding inhibitors of the invention can inhibit the binding of ligands to Nogo receptor (NgR) or to neurons. In one preferred embodiment, the NgR binding inhibitor comprises a peptide derived from MAG Ig-like domain 5 that can bind to NgR and compete with another NgR ligand (e.g., soluble or membrane-bound MAG, Nogo and OMgp) for NgR or neuron binding. Preferred peptides are selected from a region of MAG Ig-like domain 5 so that they bind to NgR but lack a stretch of amino acids sufficient for NgR activation. Preferred peptides derived from MAG are provided.

In another preferred embodiment of the invention, a NgR binding inhibitor comprises a peptide derived from Nogo-66 (or Nogo) that has sequence similarity to MAG Ig-like domain 5 wherein the peptide can bind to NgR and compete with another NgR ligand (e.g., soluble or membrane-bound MAG, Nogo and OMgp) for NgR or neuron binding. Peptides are selected from a region of Nogo-66 (or Nogo) so that they bind to NgR but do not contain a stretch of amino acids sufficient for NgR activation. Preferred peptides derived from Nogo are provided.

In another preferred embodiment of the invention, a NgR binding inhibitor comprises a peptide derived from OMgp that has sequence similarity to MAG Ig-like domain 5 wherein the peptide can bind to NgR and compete with another NgR ligand (e.g., soluble or membrane-bound MAG, Nogo and OMgp) for NgR or neuron binding. Peptides are selected from a region of OMgp so that they bind to NgR but do not contain a stretch of amino acids sufficient for NgR activation. Preferred peptides derived from OMgp are provided.

Preferred inhibitory molecules of the invention (e.g., MAG derivatives and NgR binding inhibitors) can decrease inhibition of neural regeneration by myelin. Preferably, an inhibitor of the invention can decrease inhibition of neurite outgrowth. Preferred inhibitors of the invention can regulate neural growth or regeneration, and more preferably, can promote neural growth or regeneration.

The present invention also provides NgR activating molecules. In a preferred embodiment, the activating molecule comprises a peptide derived from amino acid residues that make up a Nogo receptor ligand binding site ("NgR activator") which can both bind to and activate signaling by NgR but which are not full-length NgR ligands. In one preferred embodiment, the NgR activator comprises a peptide derived from MAG Ig-like domain 5 that can bind to NgR and compete with another NgR ligand (e.g., soluble or membrane-bound MAG, Nogo and OMgp) for NgR binding and which activates signaling (thereby potentiating neuronal inhibition). Preferred peptides are selected from a region of MAG Ig-like domain 5 (or similar Nogo and OMgp regions) so that they bind to NgR and comprise a stretch of amino acids sufficient for NgR activation, whereby the peptide promotes inhibition of neural growth and regeneration by MAG or myelin. Preferred peptides of the invention derived from MAG, Nogo, OMgp or a NgR ligand consensus sequence are provided.

The present invention also provides molecules comprising nucleic acid sequences that encode an inhibitory molecule (e.g., MAG derivative or NgR binding inhibitor), or a NgR activating molecule of the invention, as well as nucleic acid molecules consisting of sequences that selectively hybridize under conditions of high stringency to such sequences. The invention further provides vectors comprising nucleic acid sequences of the invention, including vectors which can be used to introduce, and optionally, to express, inhibitory or NgR activating molecules of the invention in host cells, animals or both.

The present invention also provides an antibody that binds to a molecule (e.g., MAG derivative, NgR binding inhibitor or NgR activator) of the invention.

The present invention further provides compositions comprising at least one inhibitory molecule (e.g., MAG derivative or NgR binding inhibitor) or NgR activating molecule of the invention. Preferred compositions of the invention are pharmaceutical compositions which comprise a therapeutically effective amount of at least one inhibitory molecule and a pharmaceutically acceptable carrier.

The present invention further provides a method of inhibiting the binding of a ligand to NgR receptor comprising the step of contacting the receptor with an effective amount of an inhibitory molecule or composition of the invention. In one preferred embodiment, the inhibitory molecule is a MAG derivative. In another preferred embodiment, the inhibitory molecule is a NgR binding inhibitor. In another preferred embodiment, the ligand is selected from the group consisting of MAG, Nogo and OMgp.

The present invention further provides a method of inhibiting the binding of a NgR ligand to a neuron comprising the step of contacting the neuron with an effective amount of an inhibitory molecule or composition of the invention. In one preferred embodiment, the inhibitory molecule is a MAG derivative. In another preferred embodiment, the inhibitory molecule is a NgR binding inhibitor. In another preferred embodiment, the NgR ligand is selected from the group consisting of MAG, Nogo and OMgp.

The present invention further provides a method of decreasing inhibition of axonal outgrowth by a neuron in the presence of myelin or MAG comprising contacting the neuron with an effective amount of an inhibitory molecule or composition of the invention. In one preferred embodiment, the inhibitory molecule is a MAG derivative. In another preferred embodiment, the inhibitory molecule is a NgR binding inhibitor. In a preferred embodiment, the method further comprises the step of monitoring growth of a neuron after administration of the inhibitor or composition.

Methods of regulating neural growth or regeneration in the nervous system comprising the step of administering an effective amount of an inhibitory molecule (e.g., MAG derivative or NgR binding inhibitor) or composition of the invention are also contemplated. In a preferred embodiment, neural growth or regeneration is promoted.

The present invention still further provides a method of treating or preventing damage to nervous tissue or neurons comprising the step of administering, in a manner which can affect the nervous system, an inhibitory molecule (e.g., MAG derivative or NgR binding inhibitor) or composition of the invention. In one embodiment, the damage results from cranial or cerebral trauma, spinal cord injury or stroke.

The present invention also provides a method of treating or preventing neural degeneration or damage associated with a disorder, disease or condition comprising the step of administering, in a manner which can affect the nervous system, an inhibitory molecule (e.g., MAG derivative or NgR binding inhibitors) or composition of the invention. In one embodiment, the disorder, disease or condition is associated with apoptosis. In another embodiment, the disorder, disease or condition results from a demyelinating disease.

Other features and advantages of the invention will be apparent from the following detailed description, and from the claims.

BRIEF DESCRIPTION OF THE DRAWINGS

FIG. 6 Nucleic acid sequence of rat MAG (SEQ ID NO: 1)

FIG. 7 Amino acid sequence of rat MAG (SEQ ID NO: 2)

FIG. 8 Nucleic acid sequence of murine MAG (SEQ ID NO: 3)

FIG. 9 Amino acid sequence of murine MAG (SEQ ID NO: 4)

FIG. 10 Nucleic acid sequence of human MAG (SEQ ID NO: 5)

FIG. 11 Amino acid sequence of human MAG (SEQ ID NO: 6)

FIG. 12 Nucleic acid sequence of human Nogo-A (SEQ ID NO:8). Nogo-66 sequences (SEQ ID NO: 10) are underlined.

FIG. 13 Amino acid sequence of human Nogo-A (SEQ ID NO:9). Nogo-66 aa sequences (SEQ ID NO: 11) are underlined.

FIG. 14 Nucleic acid sequence of murine OMgp (SEQ ID NO:12).

FIG. 15 Amino acid sequence of murine OMgp (SEQ ID NO:13).

FIG. 16 Map of MAG Derived Peptides Ig-like domains (1-5) are underlined; transmembrane domain is double underlined. The MAG peptides are shown in SEQ ID NO: 6, while the consensus sequences are shown in SEQ ID NO: 43.

FIG. 17 NgR Ligand Sequence Comparison (residues 1055-1120 of SEQ ID NO: 9, residues 432-493 of SEQ ID NO: 4 and SEQ ID NO: 13, respectively, in order of appearance).

FIG. 18 NgR Ligand Consensus Sequence (SEQ ID NO:14).

FIG. 19 NgR Ligand Derived Peptides

DETAILED DESCRIPTION OF THE INVENTION

Figure 1:
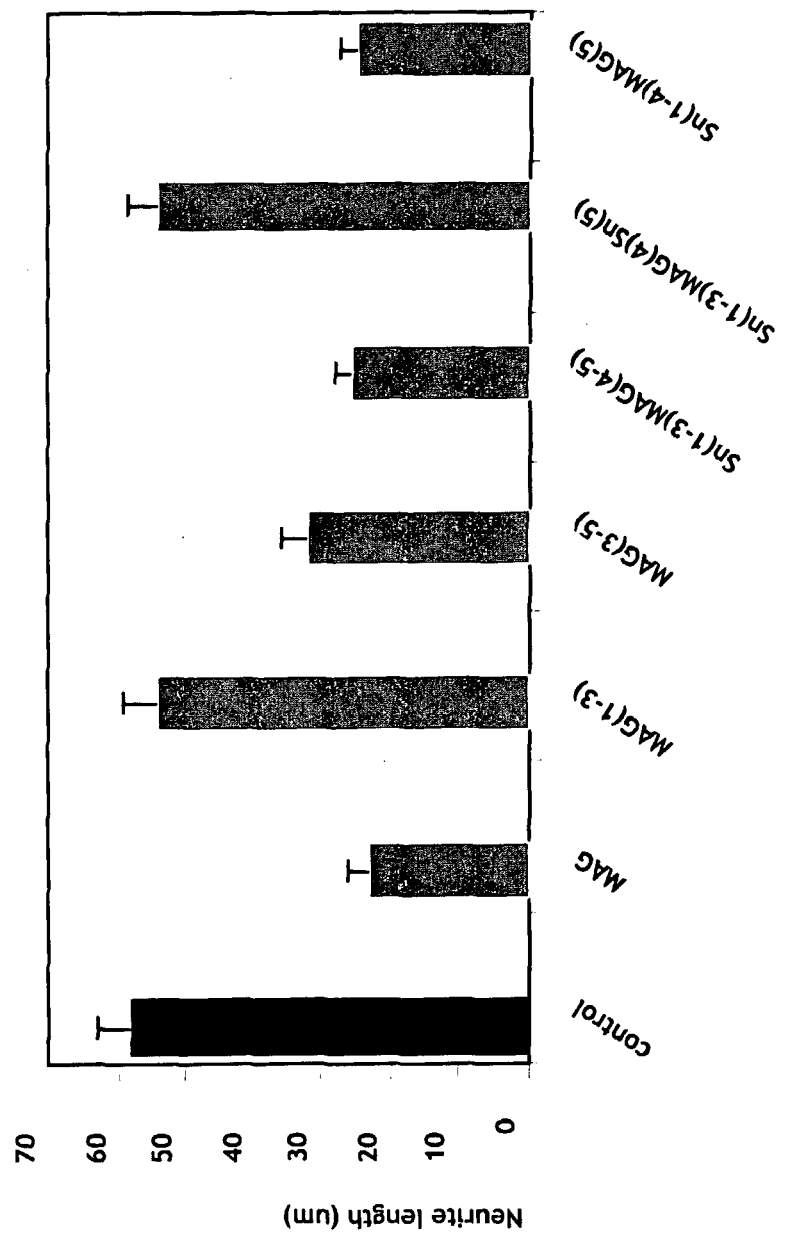
FIG. 1 Inhibition of neurite outgrowth from cerebellar neurons by truncated MAG or chimeric MAG Cerebellar neurons were isolated (Example 1) and grown overnight on a monolayer of control-transfected CHO cells (clear bar) or a monolayer of CHO cells expressing wild-type MAG or truncated, deleted or chimeric MAG derivatives (grey bars). (See Example 2). Neurons were stained for GAP-43 antigen and neurite length was measured and the average length was calculated for 180-200 neurons (+/−SEM).

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane Antibodies: A Laboratory Manual Cold Spring Harbor Laboratory Press, Cold Spring Harbor, N.Y. (1990); Principles of Neural Science, 4$^{th}$ ed., Eric R. Kandel, James H. Schwart, Thomas M. Jessell editors. McGraw-Hill/Appleton & Lange: New York, N.Y. (2000). The nomenclatures used in connection with, and the laboratory procedures and techniques of, molecular and cellular neurobiology and medicinal and pharmaceutical chemistry described herein are those well known and commonly used in the art. Standard techniques are used for chemical syntheses, chemical analyses, pharmaceutical preparation, formulation, and delivery, and treatment of patients.

All publications, patents and other references mentioned herein are incorporated by reference.

The following terms, unless otherwise indicated, shall be understood to have the following meanings:

As used herein, the term "antibody" refers to a full antibody (consisting of two heavy chains and two light chains) or a fragment thereof. Such fragments include, but are not limited to, those produced by digestion with various proteases, those produced by chemical cleavage and/or chemical dissociation, and those produced recombinantly, so long as the fragment remains capable of specific binding to an antigen. Among these fragments are Fab, Fab', F(ab')$_2$, and single chain Fv (scFv) fragments.

Within the scope of the term "antibody" are also antibodies that have been modified in sequence, but remain capable of specific binding to an antigen. Example of modified antibodies are interspecies chimeric and humanized antibodies; antibody fusions; and heteromeric antibody complexes, such as diabodies (bispecific antibodies), single-chain diabodies, and intrabodies (see, e.g., Marasco (ed.), Intracellular Antibodies: Research and Disease Applications, Springer-Verlag New York, Inc. (1998) (ISBN: 3540641513), the disclosure of which is incorporated herein by reference in its entirety).

The terms "chimeric MAG protein", "MAG chimeric fusion protein" and "chimeric MAG" refer interchangeably to a protein comprising at least a portion of MAG (i.e., at least ten contiguous MAG amino acid residues) and another protein.

The term "demyelinating disease" refers to a pathological disorder characterized by the degradation of the myelin sheath. Demyelinating diseases include but are not limited to: multiple sclerosis, monophasic demyelination, encephalomyelitis, multifocal leukoencephalopathy, panencephalitis, Marchiafava-Bignami disease, pontine myelinolysis, adrenoleukodystrophy, Pelizaeus-Merzbacher disease, Spongy degeneration, Alexander's disease, Canavan's disease, metachromatic leukodystrophy and Krabbe's disease.

The term "Ig-like domain" as used herein refers to the common structural motif of the Immunoglobulin (Ig) protein superfamily, proteins that share partial amino acid sequence homology and tertiary structural features that were originally identified in Ig heavy and light chains. Ig domains are three-dimensional globular structures having about 70 to 110 amino acid residues and an internal Cys-Cys disulfide bond. These domains contain two layers of β-pleated sheet, each layer composed of three to five antiparallel strands of five to ten amino acid residues. For a general review, see, e.g., Abbas et al., supra. Most identified members of the Ig superfamily are integral plasma membrane proteins with Ig domains in the extracellular portions and widely divergent cytoplasmic tails, usually with no intrinsic enzymatic activity. One recurrent characteristic of the Ig superfamily members is that interactions between Ig domains on different polypeptide chains (of the same or different amino acid sequences) are essential for the biological activities of the molecules. Heterophilic interactions can also occur between Ig domains on entirely distinct molecules expressed on the surfaces of different cells.

The term "inhibitory molecule" as used herein refers to a molecule that inhibits (i.e., neutralizes) an inhibitor of neural growth or regeneration. Thus, for example, an inhibitory molecule of the invention reduces or eliminates the ability of an endogenous inhibitor present in myelin to regulate neurite outgrowth. Inhibitory molecules of the invention include but are not limited to MAG derivatives and NgR binding inhibitors (e.g., peptides derived from NgR ligands such as MAG, Nogo and OMgp; peptides derived from the NgR ligand consensus sequence of the invention; as well as peptide analogs and peptidomimetics thereof.)

The term "NgR activating molecule" as used herein refers to a molecule that activates (i.e., binds to and triggers signaling of) the Nogo receptor (NgR) and which thereby potentiates inhibitors of neural growth or regeneration. NgR activator molecules of the invention include but are not limited to peptides derived from MAG Igd5, and peptides derived from analogous regions of other NgR ligands (e.g., derived from Nogo and OMgp), peptides derived from the NgR ligand consensus sequence of the invention, and peptide analogs and peptidomimetics thereof.

The term "ligand binding site" as used herein refers to amino acid residues which participate in forming the region(s) within a ligand (e.g., a NgR ligand such as MAG, Nogo and OMgp) that mediates receptor binding.

The term "(inhibitory) MAG derivative" refers to a molecule comprising amino acid sequences derived from MAG (and excluding full-length, wild type MAG), which can bind to neurons and which can interfere with the ability of endogenous or soluble MAG to bind to neurons, to bind to or activate NgR, or to regulate neurite outgrowth. As used herein, a "(inhibitory) MAG derivative" refers to molecules including but not limited to: altered or mutated MAG proteins, chimeric MAG proteins and molecules derived from MAG (e.g., MAG peptides, including peptide analogs and peptide mimetics), that are capable of: a) inhibiting the binding of MAG to a receptor that binds MAG, e.g., the NgR receptor; b) inhibiting the binding of MAG to a neuron; and c) reducing or blocking the ability of myelin, or endogenous or soluble MAG, to inhibit neurite outgrowth.

The term "MAG peptide" refers to a peptide comprising amino acid sequences derived from MAG. "MAG peptide 422-451" refers to a peptide corresponding to amino acid residues 422 to 451 of the wild-type MAG amino acid sequence (SEQ ID NOs: 2 [rat]; 4 [murine]; and 6 [human]).

The term "mutant MAG protein" refers to a MAG protein containing amino acid substitutions as compared to the wild type MAG sequence (SEQ ID NOs: 2 [rat]; 4 [murine]; and 6 [human]). Mutant MAG proteins include but are not limited to those that have one or more non-conservative amino acid substitutions as compared to the wild type MAG sequence (SEQ ID NOs: 2 [rat]; 4 [murine]; and 6 [human]). For example, "MAG(L431D)" refers to a mutant MAG protein in which the leucine at amino acid no. 431 of SEQ ID NOs: 2 [rat]; 4 [murine]; and 6 [human] has been changed to an aspartic acid. "MAG(L43 ID)-Fc" refers to a fusion protein wherein that mutant MAG protein has been fused to the soluble Fc polypeptide from an Ig molecule.

The term "mutation" as used herein refers to any change in the nucleic acid or amino acid sequence of a gene product, e.g., of MAG.

The term "NgR binding inhibitor" as used herein refers to a molecule that can compete with (i.e., reduce the ability of) a full-length or soluble form of a NgR ligand (e.g., MAG, Nogo or OMgp) to bind to (associate with) Nogo receptor, NgR, in a receptor-ligand binding assay.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

The term "regulating neural growth or regeneration" refers to promoting or inhibiting neural growth or regeneration.

The term "allelic variant" refers to one of two or more alternative naturally-occurring forms of a gene, wherein each gene possesses a unique nucleotide sequence. In a preferred embodiment, different alleles of a given gene have similar or identical biological properties.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The term includes single and double stranded forms of DNA.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, provided that it is not an unidentified member of a library which has not been separated from other members, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non-native promoter sequence can be substituted (e.g., by homologous recombination) for the native promoter of a gene in the genome of a human cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site, a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences (Pearson, 1990, (herein incorporated by reference). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., supra, page 9.51, hereby incorporated by reference. For purposes herein, "high stringency conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product. See, e.g., Leung, D. W., et al., *Technique*, 1, pp. 11-15 (1989) and Caldwell, R. C. & Joyce G. F., *PCR Methods Applic.*, 2, pp. 28-33 (1992)); and "oligonucleotide-directed mutagenesis" (a process which enables the generation of site-specific mutations in any cloned DNA segment of interest. See, e.g., Reidhaar-Olson, J. F. & Sauer, R. T., et al., *Science*, 241, pp. 53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities. A preferred polypeptide of the invention comprises an inhibitory molecule derived from MAG ("MAG derivative"), as well as a fragment, mutant, analog and derivative thereof. Another preferred polypeptide of the invention comprises a fragment derived from MAG Ig-like domain 5 ("Igd5") or a related region from another NgR ligand, such as Nogo or OMgp, and is referred to herein as a "NgR binding inhibitor" based on its ability to reduce binding of a NgR ligand to NgR. Yet another preferred polypeptide of the invention comprises a fragment derived from MAG Ig-like domain 5 ("Igd5") or a related region from another NgR ligand, such as Nogo or OMgp, and is referred to herein as a "NgR activator" based on its ability to activate NgR signaling.

The term "isolated protein" or "isolated polypeptide" is a protein or polypeptide that by virtue of its origin or source of derivation (1) is not associated with naturally associated components that accompany it in its native state, (2) when it exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See Ausubel et al., 1992, hereby incorporated by reference.

The term fusion protein refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "non-peptide analog" refers to a compound with properties that are analogous to those of a reference polypeptide. A non-peptide compound may also be termed a "peptide mimetic" or a "peptidomimetic". See, e.g., Jones, (1992) Amino Acid and Peptide Synthesis, Oxford University Press; Jung, (1997) Combinatorial Peptide and Nonpeptide Libraries: A Handbook John Wiley; Bodanszky et al., (1993) Peptide Chemistry—A Practical Textbook, Springer Verlag; "Synthetic Peptides: A Users Guide", G. A. Grant, Ed, W. H. Freeman and Co., 1992; Evans et al. *J. Med. Chem.* 30:1229 (1987); Fauchere, *J. Adv. Drug Res.* 15:29 (1986); Veber and Freidinger TINS p. 392 (1985); and references sited in each of the above, which are incorporated herein by reference. Such compounds are often developed with the aid of computerized molecular modeling. Peptide mimetics that are structurally similar to useful peptides of the invention may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein. For instance, a mutein may have an increased or decreased neuron or NgR binding activity. In a preferred embodiment of the present invention, a MAG derivative that is a mutein (e.g., in MAG Ig-like domain 5) has decreased neuronal growth inhibitory activity compared to endogenous or soluble wild-type MAG.

A mutein has at least 70% overall sequence homology to its wild-type counterpart. Even more preferred are muteins having 80%, 85% or 90% overall sequence homology to the wild-type protein. In an even more preferred embodiment, a mutein exhibits 95% sequence identity, even more preferably 97%, even more preferably 98% and even more preferably 99% overall sequence identity. Sequence homology may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the left-hand direction is the amino terminal direction and the right hand direction is the carboxy-terminal direction, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences). In a preferred embodiment, a homologous protein is one that exhibits 60% sequence homology to the wild type protein, more preferred is 70% sequence homology. Even more preferred are homologous proteins that exhibit 80%, 85% or 90% sequence homology to the wild type protein. In a yet more preferred embodiment, a homologous protein exhibits 95%, 97%, 98% or 99% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, herein incorporated by reference).

The following six groups each contain amino acids that are conservative substitutions for one another:
1) Serine (S), Threonine (T);
2) Aspartic Acid (D), Glutamic Acid (E);
3) Asparagine (N), Glutamine (Q);
4) Arginine (R), Lysine (K);
5) Isoleucine (I), Leucine (L), Methionine (M), Alanine (A), Valine (V), and
6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A preferred algorithm when comparing a inhibitory molecule sequence to a database containing a large number of sequences from different organisms is the computer program BLAST, especially blastp or tblastn (Altschul et al., 1997, herein incorporated by reference). Preferred parameters for BLASTp are:

| | |
|---|---|
| Expectation value: | 10 (default) |
| Filter: | seg (default) |
| Cost to open a gap: | 11 (default) |
| Cost to extend a gap: | 1 (default |
| Max. alignments: | 100 (default) |
| Word size: | 11 (default) |
| No. of descriptions: | 100 (default) |
| Penalty Matrix: | BLOWSUM62 |

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

The term "patient" includes human and veterinary subjects.

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold. Typically, the affinity or avidity of a specific binding reaction is at least about 10-7 M (e.g., at least about 10-8 M or 10-9 M).

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an extracellular Ig domain (i.e., MAG Igd5), a transmembrane domain, and a cytoplasmic domain (i.e., MAG C-terminal domain).

As used herein, the term "molecule" means any compound, including, but not limited to, a small molecule, peptide, protein, sugar, nucleotide, nucleic acid, lipid, etc., and such a compound can be natural or synthetic.

As used herein the phrase "therapeutically effective amount" means an amount of a molecule of the invention, such that a subject shows a detectable improvement in neuronal growth or regeneration after being treated under the selected administration regime (e.g., the selected dosage levels and times of treatment). The term "treating" is defined as administering, to a subject (e.g., a mammal; a cell in culture), a therapeutically-effective amount of a compound of the invention, to prevent the occurrence of or to control or eliminate symptoms associated with a condition, disease or disorder associated with neuronal death or lack of neuronal growth. A subject is preferably a human or other animal patient in need of treatment.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Standard reference works setting forth the general principles of recombinant DNA technology known to those of skill in the art include Ausubel et al., CURRENT PROTOCOLS IN MOLECULAR BIOLOGY, John Wiley & Sons, New York (1998 and Supplements to 2001); Sambrook et al., MOLECULAR CLONING: A LABORATORY MANUAL, 2d Ed., Cold Spring Harbor Laboratory Press, Plainview, N.Y.

(1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991). Standard reference works setting forth the general principles of immunology known to those of skill in the art include: Harlow and Lane ANTIBODIES: A LABORATORY MANUAL, 2d Ed., Cold Spring Harbor Laboratory Press, Cold Spring Harbor, N.Y. (1999); and Roitt et al., IMMUNOLOGY, 3d Ed., Mosby-Year Book Europe Limited, London (1993). Standard reference works setting forth the general principles of medical physiology and pharmacology known to those of skill in the art include: Harrison's PRINCIPLES OF INTERNAL MEDICINE, 14th Ed., (Anthony S. Fauci et al., editors), McGraw-Hill Companies, Inc., 1998.

Throughout this specification and claims, the word "comprise" or variations such as "comprises" or "comprising", will be understood to imply the inclusion of a stated integer or group of integers but not the exclusion of any other integer or group of integers.

MAG Derivatives, NgR Binding Inhibitors and NgR Activators

Inhibitory Molecules—MAG Derivatives

This invention is based in part on the identification of novel mutant MAG proteins and peptides derived from MAG that can block MAG's ability to inhibit neurite outgrowth. The present invention identifies a region within and bordering MAG Ig-like domain 5 ("Igd5") that is required for MAG's ability to inhibit neurite outgrowth.

In particular, deleted and chimeric MAG derivative proteins comprising different Ig-like domains of MAG were constructed and tested for their ability to inhibit neurite outgrowth (Examples 1-2). As shown in FIG. 1, full-length MAG ("MAG") comprising MAG Ig-like domains 1-5; a deletion derivative comprising MAG Ig-like domains 3-5 and lacking MAG Ig-like domains 1 and 2 ("MAG3-5"); a chimeric MAG derivative comprising MAG Ig-like domains 4 and 5 fused to Ig-like domains 1-3 of another neuron binding protein, sialoadhesin (Sn) (Sn(1-3)MAG(4-5)); and a chimeric MAG derivative comprising MAG Ig-like domain 5 fused to Sn Ig-like domains 1-4 (Sn(1-4)MAG(5)); were each capable of inhibiting neurite outgrowth.

In contrast, MAG derivatives lacking Ig-like domain 5 did not show this effect. In particular, a deletion derivative comprising MAG Ig-like domains 1-3 and lacking MAG Ig-like domains 4-5 ("MAG1-3"); and a chimeric MAG derivative comprising MAG Ig-like domain 4 fused to Sn Ig-like domains 1-3 and 5 ((Sn(1-3) MAG(4)Sn(5)) did not significantly inhibit neurite outgrowth. See Example 2; FIG. 1. Thus, sequences within and/or at the boundaries of MAG Ig-like domain 5 ("Igd5") are necessary and sufficient for mediating inhibition of neurite outgrowth by MAG.

Figure 2:
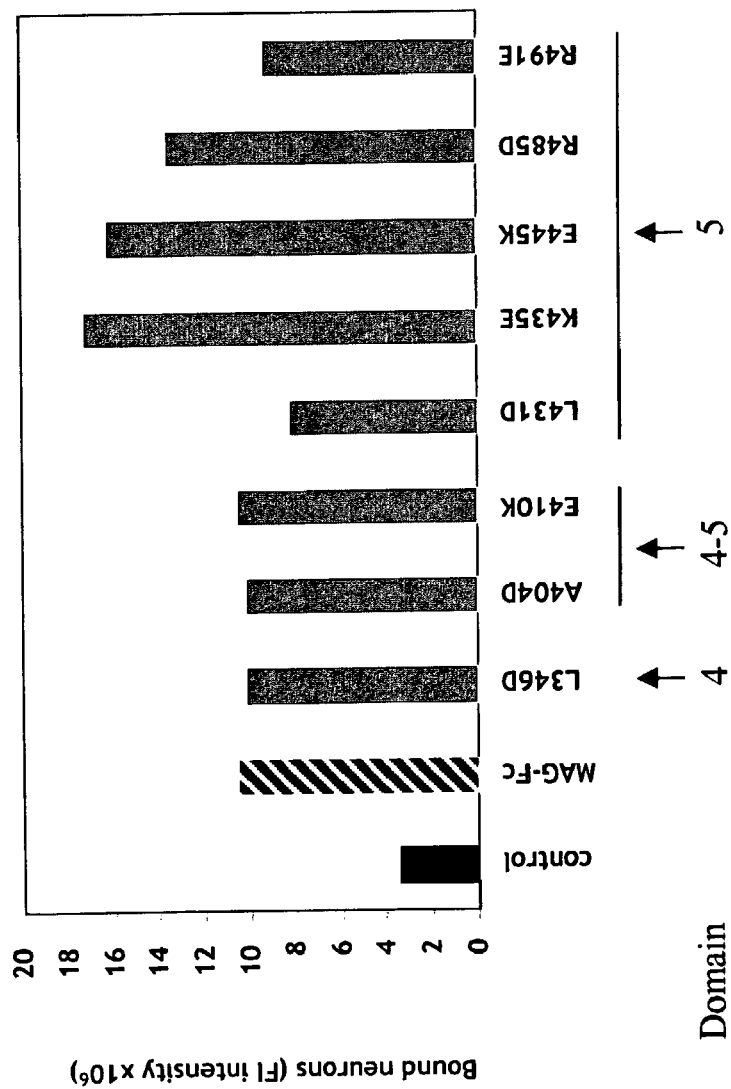
FIG. 2 Binding of mutant MAG-Fc to cerebellar neurons Wild-type or mutant MAG-Fc proteins adsorbed to microtiter plates were treated with cerebellar neurons labelled with the vital dye calcein AM. After washing, fluorescent intensity was measured to determine the number of neurons bound. Each experiment was performed in quadruplicate. Results are the mean of duplicate experiments.
Figure 3:
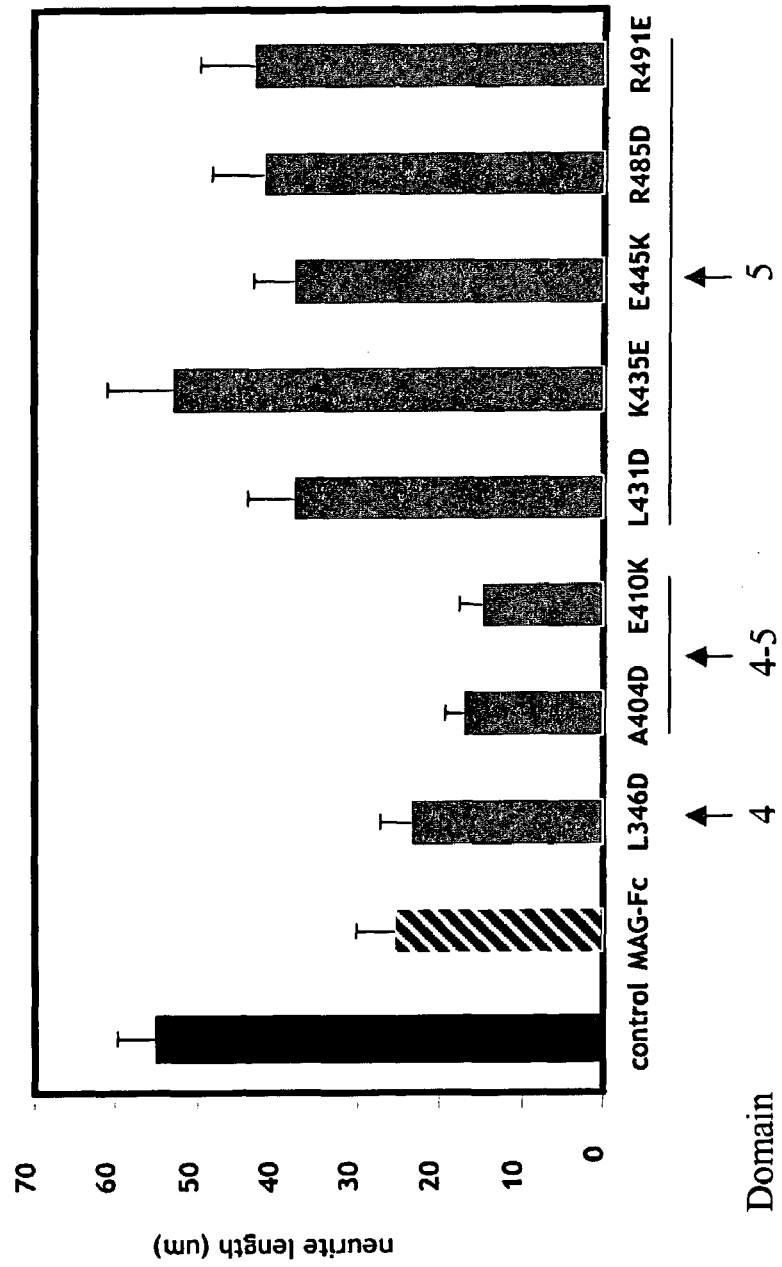
FIG. 3 Inhibition of neurite outgrowth from cerebellar neurons by MAG-FC Derivatives Cerebellar neurons were isolated (Example 1) and plated onto a growth promoting substrate of L1 protein (Example 4). A control MUC-FC fusion (clear bar), wild-type MAG-Fc (striped bar) and MAG-Fc derivatives having point mutations in MAG Ig-like domains 4 or 5 (grey bars) were constructed (Example 4) and added in soluble form to neurons (25 µg/ml). After 18 hours, cultures were fixed and stained for GAP-43 antigen. Neurite length was measured and the average length was calculated for 180-200 neurons (+/−SEM).

To delineate further the region of MAG responsible for mediating inhibition of neurite outgrowth, a series of mutations in and surrounding MAG Igd5 were constructed in MAG-Fc fusion proteins (soluble MAG derivatives) and tested for their ability to bind to neurons (Example 3) and to inhibit neurite outgrowth compared to mutations in MAG Igd4 and to controls (Example 4). As shown in FIG. 2, mutations in MAG Igd4 or Igd5 did not affect binding to neurons compared to a control Fc-chimeric protein (MUC 18-Fc). Thus, these sequences are not essential for neuron binding (at least in the context of a full-length MAG extracellular domain). Mutations in MAG Igd5, however, significantly reduced inhibition of neurite outgrowth (Example 4; FIG. 3).

As shown in FIG. 3, wild-type MAG-Fc (striped bar) inhibited neurite outgrowth by about 60% compared to the control Fc chimeric protein (MUC-Fc; clear bar). MAG-Fc chimeras mutated in Ig domain 4 (i.e., MAG(L346D)-Fc, MAG (A404D)-Fc, and MAG(E410K)-Fc) inhibited neurite outgrowth as effectively as MAG-Fc. In contrast, none of the MAG-Fc chimeras mutated in Ig domain 5 (i.e., MAG (L431D)-Fc, MAG(K435E)-Fc, MAG(E445K)-Fc. MAG (R485D)-Fc, and MAG(R491E)-Fc), inhibited neurite outgrowth compared to the control chimera. These results confirm that sequences within and at the boundaries of the fifth Ig-like domain of MAG (MAG Igd5) are required for MAG's ability to inhibit neurite outgrowth. Furthermore, the amino acids mutated in domain 5, i.e., L431D, K435E, E445K, R485D, and R491E, are essential for MAG to exert its inhibitory effect on neurite outgrowth but not for its ability to bind to neurons.

Accordingly, MAG derivatives having at least one mutation in or at the boundaries of Igd5 are useful MAG inhibitors, as they can bind to neurons (and hence compete for neuron binding with endogenous MAG) but do not inhibit neurite outgrowth. Thus, in one aspect, the present invention provides an inhibitory molecule derived from a MAG molecule having a mutation in Ig-like domain 5 (Igd5) or in a region flanking (i.e., within about 10 amino acid residues on either side of) Igd5, wherein the mutation reduces or eliminates the ability of the derivative to regulate (e.g., inhibit or promote) neurite outgrowth compared to endogenous or soluble MAG without eliminating binding to neuronal surfaces. In a preferred embodiment, the inhibitory molecule is derived from a rat, murine or human MAG having at least one mutation in or flanking Igd5 (SEQ ID NO: 7) corresponding to amino acid residues 432-488 of SEQ ID NOs: 2, 4 and 6 of rat, murine and human MAG, respectively. Preferably, the mutation in MAG Ig-like domain 5 reduces or eliminates its ability to activate signaling of the Nogo receptor (NgR) compared to endogenous or soluble MAG.

In one preferred embodiment, the MAG derivative has a mutation which is a partial or total deletion of Ig-like domain 5 ("Igd5") (SEQ ID NO: 7) and/or sequences flanking Igd5. Preferably, the deletion removes one or more amino acid residues in a region of MAG Igd5 (between amino acid residues 450 and 490 of SEQ ID NOs: 2, 4 or 6) in which there is sequence similarity with other known NgR ligands. More preferably, the deletion removes one or more amino acid residues between residues 450 and 453 of SEQ ID NOs: 2, 4 or 6. In another more preferred embodiment, the deletion removes one or more amino acid residues in a region of MAG Igd5 between amino acid residues 466 and 478 of SEQ ID NO: 2, 4 or 6, which also has some sequence similarity to other known NgR ligands. More preferably, the deletion removes one or more amino acid residues between 474 and 476 of SEQ ID NO: 2, 4 or 6. Preferred deletion mutations of the invention include but are not limited to MAGΔd5; MAGΔ450-490; MAGΔ450-453; MAGΔ466-478; and MAGΔ474-476.

A soluble MAG derivative lacking Ig-like domains 4 and 5 (MAG(d1-3)-Fc) has been described in the art. See, e.g., Kelm et al., *Current Biol.*, 4, pp. 965-72 (1994); U.S. Pat. Nos. 5,932,542; 6,203,792; and 6,399,577. This MAG derivative (or an equivalent MAG derivative in a full-length MAG background), which can bind to neurons and reduce inhibition of axonal outgrowth by MAG, is specifically excluded from the invention disclosed herein.

In another preferred embodiment, the at least one mutation in MAG is a point mutation in or flanking MAG Igd5 (SEQ ID NO: 7). Preferred inhibitors of this embodiment comprise one or more point mutations in MAG amino acid residues selected from the group consisting of residues 431, 435, 445, and 450-491 of SEQ ID NO: 2, 4 or 6. Preferred point mutations include, but are not limited to, L431D, K435E, E445K, R485D and R491E. Yet other preferred point mutations include, but are not limited to, point mutations at one or more amino acid residues in MAG regions 450-456, preferably 450-453; and 466-478, preferably 474-476 of SEQ ID NO:2, 4 or 6.

In a preferred embodiment, inhibitory MAG derivatives of the invention are soluble chimeric molecules comprising at least one extracellular domain of MAG, preferably Ig-like domain 1 of MAG (which carries a sialic acid binding site), and further comprising MAG extracellular sequences having at least one mutation (e.g., point mutation or deletion) in or flanking MAG Ig-like domain 5 (SEQ ID NO: 7). Preferred soluble MAG derivatives (e.g., MAG chimeric fusion proteins) replace the transmembrane and intracellular domains of MAG with a soluble domain, e.g., with an immunoglobulin Fc region. Other preferred soluble MAG derivatives comprises at least one extracellular domain from a heterologous protein, e.g., an Ig-like domain from a sialoadhesin molecule or another neuron binding molecule (e.g., Nogo, OMgp or other neuron binding proteins). One preferred MAG chimeric derivative of the invention is the chimeric fusion protein "Sn(1-3)MAG(4)Sn(5)" discussed above. Any preferred MAG derivative of the invention (e.g., having at least one deletion, point mutation or other mutation in MAG Igd5 which disrupts MAG inhibitory activity) may be constructed as a chimeric fusion protein, and preferably, a soluble chimeric fusion protein (i.e., lacking a transmembrane or membrane-association domain), according to methods well known to those of skill in the art.

Inhibitory Molecules—NgR Binding Inhibitors

Figure 4:
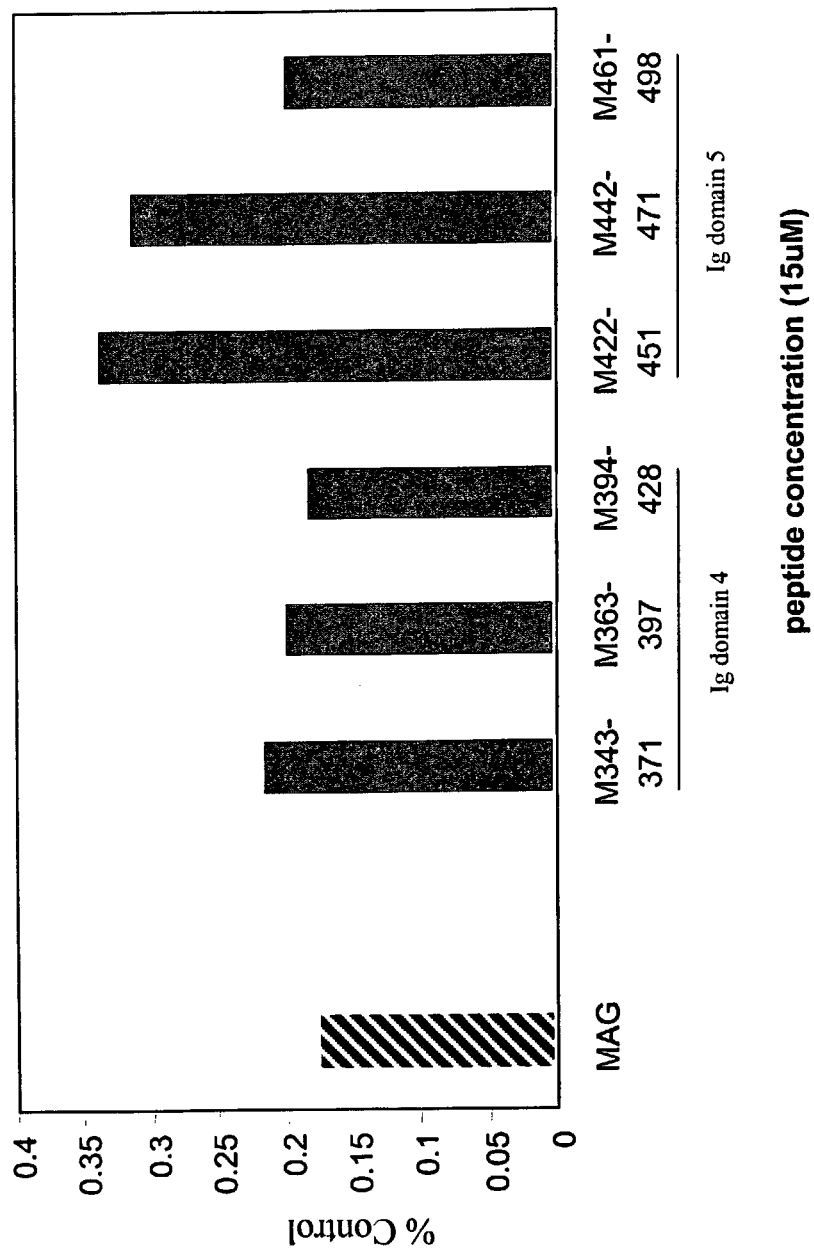
FIG. 4 Inhibition of neurite outgrowth from cerebellar neurons by MAC peptides Cerebellar neurons were isolated (Example 1) and grown overnight on a monolayer of control-transfected CHO cells (not shown) or CHO cells expressing MAG in the absence (striped bar) or the presence (grey bars) of MAG peptides (15 µM) derived from MAG Ig-like domain 4 or 5. Neurons were stained for GAP-43 antigen and neurite length was measured. Results are shown as number of neurons in each treatment having neurites longer than two times the length of the cell body.
Figure 5:
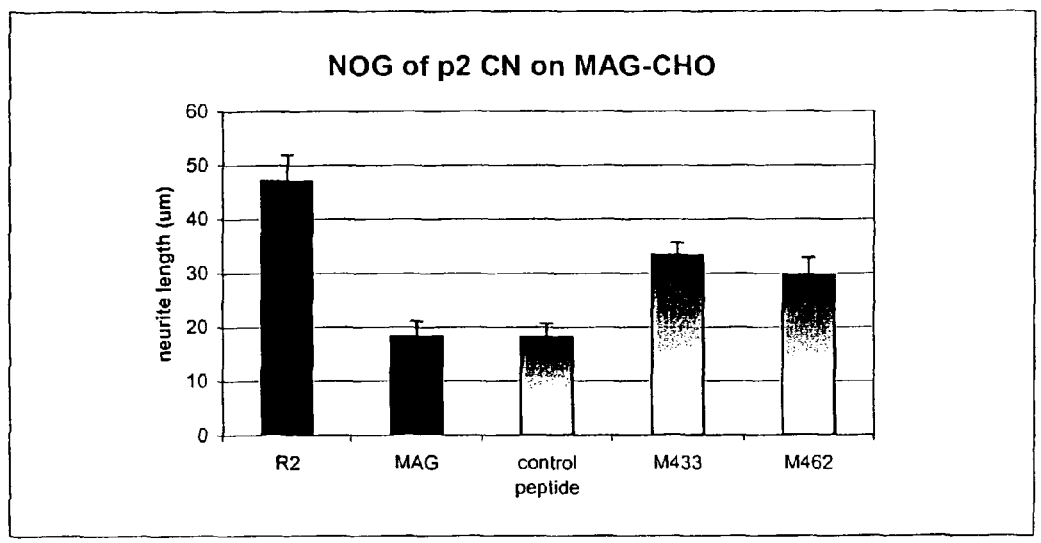
FIG. 5 Inhibition of neurite outgrowth from cerebellar neurons by MAG peptides Cerebellar neurons were isolated (Example 1) and grown for 18 hrs on a monolayer of control-transfected CHO cells (R2) or CHO cells expressing MAG in the absence of a peptide (MAG) or in the presence of a peptide derived from sialoadhesin Ig-like domain 5 (non-MAG "control peptide") or a MAG peptide (M433 or M462 at 20 µM) derived from MAG Ig-like domain 5. Neurons were stained for GAP-43 antigen and neurite length was measured and the average length was calculated for 180-200 neurons (+/−SEM).

This invention is also based on the identification of a region within and bordering MAG Ig-like domain 5 ("Igd5") that is required for MAG's ability to bind to Nogo receptor (NgR). In particular, MAG peptides consisting of consecutive amino acid residues of MAG Igd4 or MAG Igd5 were constructed and tested for their ability to reduce inhibition of neurite outgrowth by full-length, wild-type MAG (Example 5; FIGS. 4 and 5). As shown in FIG. 4, none of the peptides derived from MAG Igd4, i.e., MAG(343-371), MAG(363-397) and MAG(394-428), had a significant effect on the ability of the MAG-expressing cells to inhibit neurite outgrowth. In contrast, two of the peptides derived from MAG Igd5, MAG(422-451) ("M422") and MAG(442-471) ("M442"), strongly attenuated inhibition by MAG and allowed neurons grown on MAG-expressing cells to extend neurites that were at least twice as long as neurites extended without peptide or with any of the peptides derived from MAG Igd4. FIG. 5 shows that MAG peptides "M433" (433-457) and "M462" (462-486) even more strongly attenuated inhibition by MAG. These MAG peptides appear to block the ability of wild-type MAG to bind Nogo receptor (NgR) and thereby mediate inhibition of neurite outgrowth. Such peptides (and other agents such as peptide mimetics and analogs designed to mimic the structural features of these peptides) are an example of molecules of the invention referred to as "NgR binding inhibitors".

Interestingly, although MAG(461-498) ("M461") is also derived from MAG Igd5, this peptide had no apparent effect on inhibition of neurite outgrowth by MAG (FIG. 4). As described in more detail below, this 38 amino acid peptide spans a region of MAG Igd5 (residues 466-478 of SEQ ID NOs: 2, 4 or 6) that is conserved among ligands of NgR (e.g., MAG, Nogo-66 and OMgp). See FIGS. 16 and 17. It is likely that this conserved region represents a core NgR ligand binding site. The MAG-derived M461 peptide may thus bind to and activate NgR, which would then mask any apparent competitive effects with wild-type MAG for NgR binding (see below). As the M462 peptide consists of MAG amino acid residues 462-486 within the conserved region of Igd5 and yet behaves as an inhibitor rather than an activator, it is likely that M462 is not long enough to activate NgR signaling when bound. (Alternatively, MAG amino acid residues 487-498 may also be necessary for NgR activation).

Accordingly, in another embodiment of the invention, an inhibitory molecule comprises a peptide derived from amino acid residues that make up a Nogo receptor ligand binding site ("NgR binding inhibitor"). Preferred NgR binding inhibitors of the invention can inhibit the binding of a ligand to Nogo receptor (NgR) or to neurons. In one preferred embodiment, the NgR binding inhibitor comprises a peptide derived from MAG Ig-like domain 5 (SEQ ID NO: 7) that can bind to NgR and compete with another NgR ligand (e.g., soluble or membrane-bound MAG, Nogo or OMgp) for NgR or neuron binding. In a more preferred embodiment, the NgR binding inhibitor comprises a peptide of at least five, preferably six to ten, more preferably eleven to fifteen and most preferably greater than fifteen contiguous amino acid residues derived from a region of MAG Ig-like domain 5 (SEQ ID NO: 7), wherein the peptide blocks inhibition of neural growth and regeneration by MAG or myelin. Preferred peptides are selected from a region of MAG Ig-like domain 5 so that they bind to NgR but do not contain a stretch of amino acids sufficient for NgR activation.

Preferred peptides of the invention include peptides comprising or consisting of MAG amino acid residues 422-451 (M422) (SEQ ID NO: 15); MAG amino acid residues 442-471 (M442) (SEQ ID NO: 16); MAG amino acid residues 433-457 (M433) (SEQ ID NO: 20); and MAG amino acid residues 462-486 (M462) (SEQ ID NO: 24). Other preferred peptides include peptides comprising or consisting of MAG amino acid residues 437-441 (M437) (SEQ ID NO: 17); MAG amino acid residues 446-455 (M446) (SEQ ID NO: 18); MAG amino acid residues 450-455 (M450) (SEQ ID NO: 19); and as shown in FIGS. 15 and 18. Yet other preferred peptides include peptides comprising or consisting of MAG amino acid residues 466-471 (M466) (SEQ ID NO: 21) and MAG amino acid residues 472-477 (M472) (SEQ ID NO: 22) as shown in FIG. 18.

In general, peptides comprising or consisting of consecutive MAG amino acid residues within particular regions between 450-490; especially amino acid residues 450-453 and 462-490; and more especially amino acid residues 466-478 of SEQ ID NOs: 2, 4 or 6; should be avoided for use as NgR binding inhibitors, as these regions appear to be conserved among NgR ligands and may be sufficient for NgR signaling (see below). Peptides, preferably at least 30 amino acids in length and comprising or consisting of such consecutive amino acid residues, are useful, in contrast, as NgR activators of the invention. The MAG(461-498) peptide ("M461"), for example, does not reduce the ability of wild-type MAG to inhibit neurite outgrowth, a result which may be explained if the peptide can bind to and activate NgR (see below).

NgR Ligand Sequence Comparisons: NgR Ligand and Consensus Peptides

While there are no obvious regions of high sequence identity between NgR ligands (Domeniconi et al., supra), sequence alignments of MAG Ig-like domain 5 (MAG_d5) with OMgp (full-length) and Nogo66 using the program AlignX (component of Vector NTI Suite 8.0) by InforMax, Inc., revealed a region of sequence conservation (FIG. 16). As shown in FIG. 17, a consensus sequence derived from this region spans amino acid residues 1-59 of MAG Ig-like domain 5 (MAG_d5) (corresponding to amino acid residues 432-490 of SEQ ID NOs: 2, 4 or 6); amino acid residues 8-66 of Nogo-66 (SEQ ID NO: 11) and amino acid residues 201-259 of full length OMgp (SEQ ID NO: 13). Within that conserved region, there are particular stretches which, based on their complexity, are residues likely to be involved in NgR binding and activation:

1) MAG_d5 amino acid residues 19-24, and especially amino acid residues 19-22 (corresponding to MAG amino acid residues 450-455, and especially residues 450-453 of SEQ ID NOs: 2, 4 or 6; Nogo-66 amino acid residues 26-31, and especially residues 26-29 of SEQ ID NO: 11; and OMgp amino acid residues 219-224, and especially residues 219-222 of SEQ ID NO: 13); and 2) MAG_d5 amino acid residues 31-60, more particularly residues 35-47, even more particularly residues 37-46, and especially residues 43-45 of SEQ ID NO: 7 (corresponding to MAG amino acid residues 462-490, more particularly residues 466-478, even more particularly residues 468-477, and especially residues 474-476 of SEQ ID NOs: 2, 4 or 6; Nogo-66 amino acid residues 38-66, more particularly residues 42-54, even more particularly residues 44-53, and especially residues 50-52 of SEQ ID NO: 11; and OMgp amino acid residues 231-260, more particularly residues 235-247, even more particularly residues 237-246, and especially residues 243-245 of SEQ ID NO: 13).

Based on the above sequence comparisons and the NgR ligand consensus sequence shown in FIG. 17, NgR binding inhibitors comprising or consisting of peptides with conserved sequences derived from MAG Igd5 or from homologous regions of Nogo-66 and OMgp (including peptides comprising or consisting of sequences selected from either one of the NgR ligands or from the consensus sequence of FIG. 17) are designed and tested for their ability to reduce inhibition of neurite outgrowth by soluble or membrane-bound wild-type MAG (or alternatively, by Nogo or OMgp). See Example 6.

In particular, peptides consisting of MAG amino acid residues 437-441 (M437), 446-455 (M446), 450-455 (M450), 466-471 (M466); and 472-477 (M472) are constructed, as shown in FIG. 18. All peptides reduce the ability of the wild-type MAG-expressing cells to inhibit neurite outgrowth (Example 6).

Similarly, peptides consisting of Nogo-66 (SEQ ID NO: 11) amino acid residues 13-17 (N13) (SEQ ID NO: 25), 22-31(N22-1) (SEQ ID NO: 26), 22-34 (N22-2) (SEQ ID NO: 27), 26-31 (N26-1) (SEQ ID NO: 28); 26-34 (N26-2) (SEQ ID NO: 29); 9-33 (N9-1) (SEQ ID NO: 30); 9-34 (N9-2) (SEQ ID NO: 31); 38-62 (N38) (SEQ ID NO: 32); 42-47 (N42) (SEQ ID NO: 33); and 48-53 (N48) (SEQ ID NO: 34) are also constructed, as shown in FIG. 18. All peptides reduce the ability of wild-type MAG-expressing cells to inhibit neurite outgrowth (Example 6). These peptides are thus NgR binding inhibitors according to the invention.

Peptides consisting of OMgp (SEQ ID NO: 13) amino acid residues 206-210 (O206) (SEQ ID NO: 35), 215-224 (O215) (SEQ ID NO: 36), 219-224 (O219) (SEQ ID NO: 37), 202-226 (O202) (SEQ ID NO: 38); 231-255 (O231) (SEQ ID NO: 39), 235-240 (O235) (SEQ ID NO: 40) and 241-246 (O241) (SEQ ID NO: 41) are constructed, as shown in FIG. 17. All peptides reduce the ability of the wild-type MAG-expressing cells to inhibit neurite outgrowth (Example 6) and are thus NgR binding inhibitors of the invention.

Accordingly, in a more preferred embodiment, a NgR binding inhibitor of the invention comprises a peptide of at least five, preferably six to ten, more preferably eleven to fifteen and most preferably greater than fifteen (but less than full length) contiguous amino acid residues derived from a region of MAG Ig-like domain 5, or regions similar to MAG Ig-like domain 5 from another NgR ligand, such as Nogo or OMgp (see FIGS. 16 and 17).

In another preferred embodiment of the invention, a NgR binding inhibitor comprises or consists of a peptide derived from a region of Nogo-66 (SEQ ID NO: 13) (or Nogo (SEQ ID NO: 9)) that has sequence similarity to MAG Ig-like domain 5, wherein the peptide can bind to NgR and compete with another NgR ligand (e.g., soluble or membrane-bound MAG, Nogo and OMgp) for NgR or neuron binding. In a more preferred embodiment, the NgR binding inhibitor comprises a peptide of at least five, preferably six to ten, more preferably ten to fifteen and most preferably greater than fifteen contiguous amino acid residues derived from Nogo-66 (SEQ ID NO: 13) (or Nogo (SEQ ID NO: 9)) in a region having homology to MAG Ig-like domain 5 (SEQ ID NO: 7). Peptides are selected from a region of Nogo-66 (SEQ ID NO: 13) (or Nogo (SEQ ID NO: 9)) so that they bind to NgR but do not contain a stretch of amino acids sufficient for NgR activation. Preferred peptides of this embodiment include peptides comprising or consisting of Nogo-66 amino acid residues 13-17 (N13), Nogo-66 amino acid residues 22-31(N22-1), Nogo-66 amino acid residues 22-34 (N22-2), Nogo-66 amino acid residues 26-31 (N26-1); Nogo-66 amino acid residues 26-34 (N26-2); Nogo-66 amino acid residues 9-33 (N-9-1); and Nogo-66 amino acid residues 9-34 (N-9-2); as shown in FIG. 18. Other preferred peptides include peptides comprising or consisting of Nogo-66 amino acid residues 42-47 (N42) and Nogo-66 amino acid residues 48-53 (N48), as shown in FIG. 18.

In general, peptides comprising or consisting of consecutive Nogo-66 amino acid residues 38-62; especially 26-31 and 38-66; and more especially amino acid residues 26-29 and 42-54 should be avoided for use as NgR binding inhibitors, as these regions appear to be conserved among NgR ligands and are thus likely required for NgR signaling. Peptides preferably at least 30 amino acids in length and comprising or consisting of such consecutive amino acids residues are useful, in contrast, as NgR activators of the invention. A peptide of sufficient length comprising consecutive Nogo-66 amino acid residues 38-62 may thus be sufficient for NgR signaling (see section on NgR activator peptides, below).

Peptides derived from Nogo-66 (or human hNogo-A) have been described in the art. See, e.g., US2002/0077295; US2002/0012965; GrandPré et al., *Nature* 417:547-551 (2002); and GrandPré et al., *Nature* 403:439-444 (2000). In particular, peptides (or fusions derived therefrom) consisting of Nogo-66 amino acid residues 1-25, 1-35, 1-40 ("NEP-40"), 2-41, 6-40, 11-35 and 21-45 (see SEQ ID NO: 11) have been tested in assays for neuron binding and inhibition of axonal outgrowth. These Nogo-derived peptides, which can reduce inhibition of axonal outgrowth by Nogo, are specifically excluded from the invention disclosed herein.

In yet another preferred embodiment of the invention, a NgR binding inhibitor comprises a peptide derived from a region of OMgp that has sequence similarity to MAG Ig-like domain 5 wherein the peptide can bind to NgR and compete with another NgR ligand (e.g., soluble or membrane-bound MAG, Nogo and OMgp) for NgR or neuron binding. In a more preferred embodiment, the NgR binding inhibitor comprises a peptide of at least five, preferably six to ten, more preferably ten to fifteen and most preferably greater than fifteen contiguous amino acid residues derived from OMgp in a region having homology to MAG Ig-like domain 5. Peptides are selected from a region of OMgp so that they bind to NgR but do not contain a stretch of amino acids sufficient for NgR activation. Preferred peptides of this embodiment include peptides comprising or consisting of OMgp amino acid residues 206-210 (O206), OMgp amino acid residues 215-224 (O215), OMgp amino acid residues 219-224 (O219), and OMgp amino acid residues 202-226 (O202); as shown in FIG. 18. Other preferred peptides include peptides comprising or consisting of OMgp amino acid residues 235-240 (O235) and OMgp amino acid residues 241-246 (O241), as shown in FIG. 18.

In general, peptides comprising or consisting of consecutive OMgp amino acid residues within amino acid residues 219-260; especially amino acid residues 231-260; and more especially amino acid residues 219-222 and 235-247 should be avoided for use as NgR binding inhibitors, as these regions appear to be conserved among NgR ligands and are thus likely required for NgR signaling. Peptides preferably at least 30 amino acids in length and comprising or consisting of such consecutive amino acids residues are useful, in contrast, as NgR activators of the invention. A peptide of sufficient length comprising consecutive OMgp amino acid residues 219-260 may thus be sufficient for NgR signaling (see section on NgR activator peptides, below).

NgR Activators: NgR Ligand Sequence Comparisons and Consensus Sequence

Peptides derived from NgR ligand binding sites of MAG, Nogo (Nogo-66) and OMgp (including peptides designed using the consensus sequence derived from a sequence comparison of such NgR ligands) are expected to be useful, e.g., for triggering NgR signaling, and as such, will be useful for regulating neural sprouting and connectivity, e.g., for preventing aberrant sprouting and for preventing misconnections after injury, and for preventing pain and are thus also provided by the present invention. Such a peptide is designed and selected for its ability to bind to NgR and trigger receptor signaling based on receptor-ligand binding assays and biological signaling assays known in the art, such as those referred to herein.

Preferred NgR activator peptides may be derived from NgR ligand sequences, e.g., MAG, Nogo, OMgp or a consensus sequence derived from a comparison of such sequences (FIGS. 16 and 17; SEQ ID NO: 14). Accordingly, in one preferred embodiment, an NgR activator of the invention comprises a peptide derived from MAG sequences (but excluding a full length MAG extracellular domain) that can bind to and activate NgR signaling. Preferred peptides are selected from a region of MAG Ig-like domain 5 (or similar Nogo and OMgp regions) so that they bind to NgR and comprise a stretch of amino acids sufficient for NgR activation, whereby the peptide promotes inhibition of neural growth and regeneration by MAG or myelin. Preferred MAG-derived activator peptides are more than 30 amino acid residues in length and comprise or consist of MAG amino acid residues 450-490, preferably 462-490, more preferably 466-478, even more preferably 468-477 and especially amino acid residues 474-476 (see SEQ ID NOS: 2, 4 or 6). One preferred NgR activator is the peptide MAG(461-498) ("M461") (SEQ ID NO: 23), described above. This 38 amino acid peptide encompasses a region of MAG Igd5 (residues 466-478 of SEQ ID NOs: 2, 4 or 6) that is conserved among ligands of NgR (e.g., MAG, Nogo-66 and OMgp). See FIGS. 16 and 17.

Peptide M461 may comprise amino acid residues necessary and sufficient for binding and activation of NgR, which may mask apparent competitive effects with wild-type MAG for NgR binding. These and similarly designed peptides are useful as NgR activators of the invention.

The invention also provides MAG derivative polypeptide fragments that comprise MAG Ig-like domain 5 but lack one or more of Ig-like domains 1-4 of MAG. Such fragments can bind to and activate NgR signaling and are, as such, NgR activators according to the invention. Preferred MAG derivatives of this embodiment include "MAG(d3-5)", "MAG(d4-5)" and "MAG(d5)" constructs, where the recited MAG Ig-like domains are optionally constructed in the background of a chimeric fusion (see, e.g., FIG. 1 and Example 2: "MAG(3-5)", "Sn(1-3)MAG(4-5)", and "Sn(1-4)MAG(5)"), or as a soluble chimeric fusion (e.g., comprising an immunoglobulin Fc domain).

In another preferred embodiment, an NgR activator of the invention comprises a peptide derived from Nogo-66 sequences (but excluding a full length Nogo extracellular domain, i.e., full-length Nogo-66) that can bind to and activate NgR signaling. Preferred peptides of this embodiment are selected from a region of Nogo having sequence similarity with MAG Ig-like domain 5. Such peptides are selected so that they bind to NgR and comprise a stretch of amino acids sufficient for NgR activation, whereby the peptide promotes inhibition of neural growth and regeneration by MAG or myelin. Preferred Nogo-derived activator peptides are at least 30 amino acid residues in length and comprise or consist of Nogo-66 amino acid residues 26-66, preferably 38-66, more preferably 42-54, even more preferably 44-53 and especially amino acid residues 50-52 (see SEQ ID NO:11).

Peptides derived from Nogo-66 (or human hNogo-A) have been described in the art. See, e.g., US2002/0077295; US2002/0012965; GrandPré et al., Nature 417:547-551 (2002); and GrandPré et al., Nature 403:439-444 (2000). In particular, the prior art cited above has identified a peptide consisting of Nogo-66 amino acid residues 31-55 (hNogo-A amino acid residues 1085-1109 of SEQ ID NO: 9) as comprising the core Nogo sequences critical for inhibition of axonal outgrowth. This Nogo-derived peptide, which can bind to NgR and inhibit axonal outgrowth, is specifically excluded from the invention disclosed herein. Moreover, the present invention further defines the region critical for Nogo inhibitory activity as Nogo-66 amino acid residues 42-54 ("N-42"; SEQ ID NO: 11).

In yet another preferred embodiment, an NgR activator of the invention comprises a peptide derived from OMgp sequences (but excluding a full length OMgp extracellular domain) that can bind to and activate NgR signaling. Preferred peptides of this embodiment are selected from a region of OMgp having sequence similarity with MAG Ig-like domain 5. Such peptides are selected so that they bind to NgR and comprise a stretch of amino acids sufficient for NgR activation, whereby the peptide promotes inhibition of neural growth and regeneration by MAG or myelin. Preferred OMgp-derived peptides comprise or consist of OMgp amino acid residues 219-260, preferably 231-260, more preferably 235-247, even more preferably 237-246, and especially amino acid residues 243-245 (see SEQ ID NO:13).

NgR activators of the invention, including peptides derived from MAG, Nogo-66, OMgp or the NgR ligand consensus sequence of FIG. 17, are expected to be useful for triggering NgR signaling, and as such, will be useful for regulating neural sprouting and connectivity, e.g., for preventing aberrant sprouting and for preventing misconnections after injury, and for preventing pain and are thus also provided by the present invention.

Derivatives and Analogs of Inhibitory MAG Derivatives, NgR Binding Inhibitors and NgR Activators: Sequence and Structure Variations An inhibitory polypeptide (MAG derivative or NgR binding inhibitor) of the invention comprises a fragment, fusion, mutein, allelic variant, analog or other derivative of MAG or other NgR ligand as long as the polypeptide is capable of competing with endogenous, membrane-bound or soluble MAG for neuron binding and does not itself inhibit neuronal growth or regeneration. Similarly, an NgR activator of the invention comprises a fragment, fusion, mutein, allelic variant, analog or other derivative of MAG or other NgR ligand as long as the polypeptide is capable of competing with endogenous, membrane-bound or soluble MAG for neuron binding and is also capable of inhibiting neuronal growth or regeneration. Methods for assaying competitive MAG binding and neuronal growth inhibition are disclosed, e.g., in WO 97/01352; see also U.S. Pat. No. 5,932,542; U.S. Pat. No. 6,203,792; U.S. Pat. No. 6,399,577; and assays disclosed herein.

Minor variations in the amino acid sequences of MAG derivatives and NgR binding inhibitors and activators (e.g., mutant MAG proteins and NgR ligand-derived peptides) are considered to be part of the present invention, provided that the variations in the amino acid sequence maintain at least 75%, more preferably at least 80%, 90%, 95%, and most preferably 99% sequence identity and the molecule retains bioactivity (e.g., regulation of nerve growth and regeneration). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family.

For example, it is reasonable to expect that an isolated replacement of a leucine with an isoleucine or valine, an aspartate with a glutamate, a threonine with a serine, or a similar replacement of an amino acid with a structurally related amino acid will not have a major effect on the properties of the resulting molecule. Whether an amino acid change results in a functional peptide or protein can readily be determined by assaying the specific activity of the peptide or protein derivative using, e.g., the assays described in detail herein.

In another embodiment, the invention provides a derivative of a polypeptide of the invention. In a preferred embodiment, the derivative has been acetylated, carboxylated, phosphorylated, glycosylated or ubiquitinated. In another preferred embodiment, the derivative has been labeled with, e.g., radioactive isotopes such as $^{125}I$, $^{32}P$, $^{35}S$, and $^{3}H$. In another preferred embodiment, the derivative has been labeled with fluorophores, chemiluminescent agents, enzymes, and antiligands that can serve as specific binding pair members for a labeled ligand.

Fusion Proteins

The polypeptides of this invention may be fused to other molecules, such as genetic, enzymatic or chemical or immunological markers such as epitope tags. Fusion partners include, inter alia, myc, hemagglutinin (HA), GST, immunoglobulins, β-galactosidase, biotin trpE, protein A, β-lactamase, α-amylase, maltose binding protein, alcohol dehydrogenase, polyhistidine (for example, six histidine at the amino and/or carboxyl terminus of the polypeptide), lacZ, green fluorescent protein (GFP), yeast a mating factor, GAL4 transcription activation or DNA binding domain, luciferase, and serum proteins such as ovalbumin, albumin and the constant domain (e.g., Fc) of IgG. See, e.g., Godowski et al., 1988, and Ausubel et al., supra. Immunoglobulin Fe regions are especially useful fusion partners for making secreted fusion proteins as immunoglobulin molecules are secreted at high levels from the mature plasma cell, and the Fe region appears to be well suited as a "surrogate mother", accepting domains from other proteins and efficiently directing them through the endoplasmic reticulum and secretory pathway.

Fusion proteins may also contain sites for specific enzymatic cleavage, such as a site that is recognized by enzymes such as Factor XIII, trypsin, pepsin, or any other enzyme known in the art. Fusion proteins will typically be made by either recombinant nucleic acid methods, as described above, chemically synthesized using techniques such as those described in Merrifield, 1963, herein incorporated by reference, or produced by chemical cross-linking. Tagged fusion proteins permit easy localization, screening and specific binding via the epitope or enzyme tag. See Ausubel, 1991, Chapter 16. Some tags allow the protein of interest to be displayed on the surface of a phagemid, such as M13, which is useful for panning agents that may bind to the desired protein targets. Another advantage of fusion proteins is that an epitope or enzyme tag can simplify purification. These fusion proteins may be purified, often in a single step, by affinity chromatography. For example, a $His^6$ tagged protein can be purified on a Ni affinity column and a GST fusion protein can be purified on a glutathione affinity column. Similarly, a fusion protein comprising the Fe domain of IgG can be purified on a Protein A or Protein G column and a fusion protein comprising an epitope tag such as myc can be purified using an immunoaffinity column containing an anti-c-myc antibody. It is preferable that the epitope tag be separated from the protein encoded by the essential gene by an enzymatic cleavage site that can be cleaved after purification. A second advantage of fusion proteins is that the epitope tag can be used to bind the fusion protein to a plate or column through an affinity linkage for screening targets.

Accordingly, the invention provides a MAG derivative which is a fusion protein comprising all or a part of a MAG derivative having at least one mutation in or flanking Ig-like domain 5. The invention also provides a nucleic acid molecule that encodes such a fusion protein. In another preferred embodiment, the fusion protein is a soluble MAG fusion protein which lacks the transmembrane domain (amino acid residues 501-534 of SEQ ID NOs: 2, 4 or 6 [rat, murine and human MAG, respectively]) and which is fused to an agent, such as another protein domain, that renders the fusion protein soluble and which provides increased stability and/or bioavailability to the fusion protein. One example of such a domain is an immunoglobulin Fe domain. It is also envisioned that the NgR inhibitors and activators of the invention, including peptides or non-peptide analogs and mimetics (see below) designed to mimic regions of MAG IgdS or its homologs, may similarly be engineered as fusion proteins to add desirable protein domains and corresponding ancillary functions to those molecules.

Peptide Analogs and Mimetics

This invention also expressly includes peptide analogs and mimetics which mimic the three-dimensional structure of an inhibitory MAG derivative, NgR binding inhibitor or NgR activator of the invention. Such peptide mimetics can compete for neuron binding and/or NgR binding with MAG and other NgR ligands, and can block (inhibitors) or potentiate (activators) the inhibitory effects of MAG and other NgR ligands on neuronal growth and regeneration. Peptide mimetics are expected to be superior to naturally-occurring peptides for a variety of reasons, including greater chemical stability, enhanced bioactivity and pharmacological properties (half-life, absorption, potency, efficacy, etc.), the potential for altered specificity (e.g., a broad-spectrum of biological activities), reduced antigenicity, and economic considerations with regard to production.

Generally, peptidomimetics are structurally similar to a paradigm polypeptide (i.e., a polypeptide that has a desired biochemical property or pharmacological activity), but have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, —CH(OH)CH$_2$—, and BCH$_2$SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference); for example, by adding internal cysteine residues capable of forming intramolecular disulfide bridges which cyclize the peptide.

In one embodiment, mimetics of the invention are peptide-containing molecules that mimic elements of protein secondary structure by orienting chemical structural motifs to facilitate desired molecular interactions similar to the natural molecule (see, e.g., Johnson et al., (1993) Peptide Turn Mimetics, in Biotechnology and Pharmacy, Pezzuto et al., (editors) Chapman and Hall).

Polypeptide analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991), which are each incorporated herein by reference.

In another embodiment, peptide analogs of the invention are non-peptide compounds with properties analogous to those of a template peptide, also referred to as "peptide mimetics" or "peptidomimetics" and may be developed with the aid of computerized molecular modeling, as described (see, e.g., Fauchere, (1986) Adv. Drug Res. 15, 29-69; Veber & Freidinger, (1985) Trends Neurosci. 8, 392-396; Evans et al., (1987) J. Med. Chem. 30, 1229-1239, which are incorporated herein by reference).

Improved peptide mimetics may be designed using combinatorial chemistry to create drug libraries. The design of peptide mimetics can be aided by identifying amino acid mutations that increase or decrease binding of NgR ligands (such as MAG, Nogo or OMgp) to NgR. Approaches that can be used include the yeast two hybrid method (see Chien et al., (1991) Proc. Natl. Acad. Sci. USA 88, 9578-9582; Fields et al., (1989) Nature 340, 245-246) and phage display methods (see, e.g., Amberg et al., (1993) Strategies 6, 2-4; Hogrefe et al., (1993) Gene 128, 119-126). These and other related methods in the art allow positive and negative selection for protein-protein interactions and permit the sequences that determine these interactions to be identified. For additional information, see also Jones, (1992) Amino Acid and Peptide Synthesis, Oxford University Press; Jung, (1997) Combinatorial Peptide and Nonpeptide Libraries: A Handbook John Wiley; and Bodanszky et al., (1993) Peptide Chemistry—A Practical Textbook, Springer Verlag.

Methods Using MAG Derivatives, NgR Binding Inhibitors and NgR Activators of the Invention All three known inhibitors of neural regeneration, MAG, Nogo, and OMgp, bind to the same receptor (NgR) to exert their inhibitory effects. Furthermore, all three inhibitors bind to overlapping sites on the NgR receptor. Thus, an inhibitory molecule of the invention (e.g., a MAG derivative or NgR binding inhibitor) can inhibit the binding of endogenous, membrane-bound or soluble MAG, Nogo and/or OMgp to the NgR receptor. Accordingly, the present invention provides a method of inhibiting the binding of a ligand (e.g., MAG, Nogo, and/or OMgp) to the NgR receptor comprising the step of contacting the receptor with an inhibitory molecule, or composition comprising an inhibitory molecule, of the invention. In a preferred embodiment, the inhibitory molecule comprises a MAG derivative having at least one mutation in or flanking MAG Ig-like domain 5. In another preferred embodiment, the inhibitory molecule comprises a NgR binding inhibitor (e.g., a peptide or analog or mimetic thereof) derived from a region of MAG Ig-like domain 5 that is conserved among NgR ligands, and/or a homologous region from another NgR ligand (e.g., Nogo or OMgp), wherein the peptide can bind to NgR and compete with another NgR ligand for NgR or neuron binding and can reduce inhibition of neurite outgrowth by MAG. Any of numerous receptor-ligand or other molecular binding assays may be used to assess ligand binding and competition for ligand binding in the presence of a putative inhibitory molecule. Preferably, an inhibitory molecule of the invention will compete for (i.e., reduce) MAG or other NgR ligand binding to NgR in a dosage dependent manner, using one of the assays described below.

It is further contemplated that an inhibitory molecule of the invention (e.g., an inhibitory MAG derivative or NgR binding inhibitor) can inhibit the binding of endogenous, membrane-bound or soluble MAG, Nogo, and/or OMgp to a neuron. Thus, the present invention further provides a method of inhibiting the binding of a NgR ligand (e.g., MAG, Nogo, and/or OMgp) to a neuron comprising the step of contacting the neuron with an inhibitory molecule (e.g., MAG derivative or NgR binding inhibitor) of the invention. In a preferred embodiment, the inhibitory molecule comprises a MAG derivative having at least one mutation in or flanking MAG Ig-like domain 5. In another preferred embodiment, the inhibitory molecule comprises a NgR binding inhibitor (e.g., a peptide or analog or mimetic thereof) derived from a region of MAG Ig-like domain 5 that is conserved among NgR ligands, and/or a homologous region from another NgR ligand (e.g., Nogo or OMgp), wherein the peptide can bind to NgR and compete with another NgR ligand for NgR or neuron binding and can reduce inhibition of neurite outgrowth by MAG. Any of a number of known methods for measuring specific binding of a molecule to a neuron may be used to assess competition for neuron binding in the presence of a putative inhibitory molecule of the invention. An inhibitory molecule of the invention preferably will compete (i.e., reduce) the ability of endogenous, membrane-bound or soluble MAG to bind to a neuron in a dosage-dependent manner using one of the assays described below.

It is further contemplated that an inhibitory molecule of the invention (e.g., an inhibitory MAG derivative or NgR binding inhibitor) can reduce the ability of myelin—or inhibitory molecules present in myelin (e.g., MAG, Nogo and OMgp)—to inhibit axonal outgrowth by a neuron. Thus, the present invention provides a method for decreasing inhibition of axonal outgrowth by a neuron in the presence of myelin, MAG, Nogo or OMgp, the method comprising the step of contacting a neuron with an inhibitory molecule (e.g., MAG derivative or NgR binding inhibitor) of the invention. In a preferred embodiment, the method further comprises the step of monitoring growth of a neuron after administration of the inhibitory molecule or composition. In a preferred embodiment, the inhibitory molecule comprises a MAG derivative having at least one mutation in or flanking MAG Ig-like domain 5.

In another preferred embodiment, the inhibitory molecule comprises a NgR binding inhibitor (e.g., a peptide or analog or mimetic thereof) derived from a region of MAG Ig-like domain 5 that is conserved among NgR ligands, and/or a homologous region from another NgR ligand (e.g., Nogo or OMgp), wherein the peptide can bind to NgR and compete with another NgR ligand for NgR or neuron binding and can reduce inhibition of neurite outgrowth by MAG. Any of a number of known methods for measuring neuronal outgrowth in the presence of inhibitors may be used to assess the ability of a putative inhibitory molecule of the invention to reduce such inhibition. An inhibitory molecule of the invention preferably will compete (i.e., reduce) the ability of endogenous, membrane-bound or soluble MAG to inhibit axonal outgrowth from a neuron in a dosage-dependent manner using one of the assays described below.

It is further contemplated that an inhibitory molecule (e.g., an inhibitory MAG derivative or NgR binding inhibitor) or an NgR activator of the invention can regulate neuronal growth, regeneration, connectivity and repair in the nervous system. Accordingly, the invention further provides a method for regulating neural growth or regeneration in the nervous system comprising the step of administering an effective amount of a polypeptide (e.g., an inhibitory molecule or an NgR activator), or composition comprising a polypeptide, of the invention. In a preferred embodiment, the polypeptide is an inhibitory molecule of the invention (e.g., a MAG derivative or NgR binding inhibitor) and neural growth or regeneration is promoted. In a more preferred embodiment, the inhibitory molecule comprises a MAG derivative having at least one mutation in or flanking MAG Ig-like domain 5. In another more preferred embodiment, the inhibitory molecule comprises a NgR binding inhibitor (e.g., a peptide or analog or mimetic thereof) derived from a region of MAG Ig-like domain 5 that is conserved among NgR ligands, and/or a homologous region from another NgR ligand (e.g., Nogo or OMgp), wherein the peptide can bind to NgR and compete with another NgR ligand for NgR or neuron binding and can reduce inhibition of neurite outgrowth by MAG. In another preferred embodiment, the polypeptide of the invention is a NgR activator and neural growth and regeneration is reduced or re-routed. Any of a number of known methods for measuring neural growth and regeneration, in vitro or in vivo (including but not limited to those described herein) may be used to assess the ability of a putative polypeptide of the invention to regulate neural growth and regeneration.

The present invention still further provides a method of treating or preventing damage to nervous tissue or neurons comprising the step of administering, in a manner which can affect the nervous system, an inhibitory molecule (e.g., MAG derivative or NgR binding inhibitor), or composition comprising an inhibitory molecule, of the invention. In a preferred embodiment, the inhibitory molecule comprises a MAG derivative having at least one mutation in or flanking MAG Ig-like domain 5. In another preferred embodiment, the inhibitory molecule comprises a NgR binding inhibitor (e.g., a peptide or analog or mimetic thereof) derived from a region of MAG Ig-like domain 5 that is conserved among NgR ligands, and/or a homologous region from another NgR ligand (e.g., Nogo or OMgp), wherein the peptide can bind to NgR and compete with another NgR ligand for NgR or neuron binding and can reduce inhibition of neurite outgrowth by MAG. In a preferred embodiment, the damage results from peripheral nerve injury or neuropathy, cranial or cerebral trauma, aneurysm, spinal cord injury or stroke.

The present invention also provides a method of treating or preventing neural degeneration or damage associated with a disorder, disease or condition comprising the step of administering, in a manner which can affect the nervous system, an inhibitory molecule (e.g., MAG derivative or NgR binding inhibitors), or composition comprising an inhibitory molecule, of the invention. In a preferred embodiment, the inhibitory molecule comprises a MAG derivative having at least one mutation in or flanking MAG Ig-like domain 5. In another preferred embodiment, the inhibitory molecule comprises a NgR binding inhibitor (e.g., a peptide or analog or mimetic thereof) derived from a region of MAG Ig-like domain 5 that is conserved among NgR ligands, and/or a homologous region from another NgR ligand (e.g., Nogo or OMgp), wherein the peptide can bind to NgR and compete with another NgR ligand for NgR or neuron binding and can reduce inhibition of neurite outgrowth by MAG. In a preferred embodiment, the disorder, disease or condition is associated with apoptosis. In another preferred embodiment, the disorder, disease or condition results from a demyelinating disease. Diseases which may be treated include, but are not limited to: Alzheimer's disease, Parkinson's disease, Creutzfeldt-Jacob disease, kuru, Huntington's disease, multiple system atrophy, amyotropic lateral sclerosis (Lou Gehrig's disease), progressive supranuclear palsy, and demyelinating diseases including multiple sclerosis, monophasic demyelination, encephalomyelitis, multifocal leukoencephalopathy, panencephalitis, Marchiafava-Bignami disease, pontine myelinolysis, adrenoleukodystrophy, Pelizaeus-Maerzbacher disease, Spongy degeneration, Alexander's disease, Canavan's disease, metachromatic leukodystrophy and Krabbe's disease.

The present invention also provides a method of treating or preventing neural degeneration or damage associated with a disorder, disease or condition comprising the step of administering, in a manner which can affect the nervous system, a neuron which has been exposed to an inhibitory molecule (e.g., MAG derivative or NgR binding inhibitors), or composition comprising an inhibitory molecule, of the invention. In one embodiment, the neuron is exposed ex vivo (e.g., in culture) to an inhibitory molecule of the invention. In another embodiment, the neuron is exposed in vivo to an inhibitory molecule of the invention. In a preferred embodiment, the inhibitory molecule comprises a MAG derivative having at least one mutation in or flanking MAG Ig-like domain 5. In another preferred embodiment, the inhibitory molecule comprises a NgR binding inhibitor (e.g., a peptide or analog or mimetic thereof) derived from a region of MAG Ig-like domain 5 that is conserved among NgR ligands, and/or a homologous region from another NgR ligand (e.g., Nogo or OMgp), wherein the peptide can bind to NgR and compete with another NgR ligand for NgR or neuron binding and can reduce inhibition of neurite outgrowth by MAG.

Assays While not intended to be limiting, the following assays may be used in accordance with the invention, with variations that will be apparent to one of skill in the art (e.g., in the type of neuron, the type of transformed cells and the type of molecules on growth permissive substrate surfaces).

1. Neurite Outgrowth Assays. A variety of neurite outgrowth assays (e.g., using cultured neurons) are known in the art. Any of these assays may be used as described (or adapted using methods known to those of skill in the art) to determine whether a putative inhibitory MAG derivative or NgR binding inhibitor can reduce neuronal inhibition in the presence of myelin; of full-length or modified NgR ligands such as MAG, Nogo and OMgp; or of full-length or modified NgR. Similarly, a NgR activator molecule of the invention may be identified using the same assays but looking for molecules that enhance rather than reduce neuronal inhibition in the presence of myelin; full-length or modified NgR ligands; or full-length or modified NgR. Neurite outgrowth assays may be performed, for example, using cultured neurons in the presence of purified myelin. See, e.g., GrandPré et al., Nature 417:547-551 (2002); see also Norton and Poduslo, J. Neurochem. 21:749-757 (1983) for myelin preparations.

Alternatively, neurite outgrowth assays may be performed on a growth permissive substrate, e.g., on a monolayer of transfected cells (e.g., COS or CHO cells) that are engineered to express cell surface neural inhibitory molecules, such as MAG (see, e.g., Domeniconi et al., Neuron 35:283-290 (2002); WO 97/01352); OMgp (see, e.g., Wang et al., Nature 417:941-944 (2002); chimeric molecules derived therefrom (Example 2); or cells that express NgR or NgR derivatives (see, e.g., Domeniconi et al., Neuron 35:283-290 (2002); Liu et al., Science 297:1190-1193 (2002); Wang et al., Nature 417:941-944 (2002); GrandPré et al., Nature 417:547-551 (2002)).

The above neurite outgrowth assay may also be modified for use with soluble inhibitory molecules, such as soluble MAG, Nogo-66 or OMgp molecules (typically rendered soluble by replacement of the intracellular and transmembrane domains with a soluble protein domain that provides stability to the chimeric fusion molecule, e.g., an immunoglobulin Fc domain such as IgG-Fc). Assays using soluble inhibitory molecules may be performed on a monolayer of cells that express or which are treated with a growth permissive substrate that stimulates neurite outgrowth (e.g., a cell surface expressed cell adhesion molecule (CAM) such as the L1 glycoprotein or treatment with a soluble CAM such as L1-Fc) (see, e.g., Doherty et al., Neuron:57-66 (1995); WO 97/01352; each of which is incorporated herein by reference in its entirety. Preferred traceable fusion proteins are radioactively or fluorescently labeled using commercially available reagents and methods well known in the art.

Because NgR signaling (activation) mediates neuronal inhibition by MAG, Nogo and OMgp, neurite outgrowth assays, such as those described above, may be used to assess NgR activation/activation. In addition, NgR mediated growth cone morphology and growth cone collapse assays may be used to assess NgR activation/activation and may performed as described (e.g., Liu et al., Science 297: 1190-1193 (2002); Wang et al., Nature 417:941-944 (2002); GrandPré et al., Nature 417:547-551 (2002)).

2. Neuron Binding Assays

Different neuronal cell types can be isolated using methods well known in the art. For example, neurons can be isolated essentially as described in Doherty et al., Nature, 343, pp. 464-66 (1990); Neuron, 5, pp. 209-19 (1990); and Kleitman et al., Culturing Nerve Cells, pp. 337-78, MIT Press, Cambridge, Mass./London, England (G. Banker and K. Goslin, Eds.) (1991). Binding to neurons of soluble NgR ligands (e.g., soluble MAG- or Nogo-Fc-chimeras such as those described in Domeniconi et al., Neuron 35:283-290 (2002)) may be detected essentially as described in DeBallard et al., Mol. Cell. Neurosci. 7:89-101 (1996); see also WO 97/01352. Alternatively, transfected cells expressing such NgR ligands on the cell surface may be used in binding assays. Neuronal binding may be directly or indirectly detected in such assays, using conventional labeling and immunological techniques. These or other known binding assays may be used to determine whether a putative inhibitory MAG derivative or NgR binding inhibitor can interfere with the ability of MAG or another NgR ligand to bind to neurons.

3. NgR Binding

Binding of a molecule to NgR may be measured using one of many known ligand-receptor binding assays. Binding of labeled NgR ligand molecules to transfected cells expressing NgR or derivatives of NgR have been particularly useful assays and are available in the art. See, e.g., Domeniconi et al., Neuron 35:283-290 (2002); Liu et al., Science 297: 1190-1193 (2002); Wang et al., Nature 417:941-944 (2002); Fournier et al., Nature 409:341-346 (2001)). Similarly, binding of soluble NgR (e.g., NgR-AP) or NgR derivatives to cells expressing NgR ligands or derivatives thereof (e.g., MAG-expressing cells) may also be used (e.g., Domeniconi et al., Neuron 35:283-290 (2002)) to assess NgR binding. Ligand binding may be directly or indirectly detected in such assays, using conventional labeling and immunological techniques. These or other assays may be used to determine whether a putative inhibitory MAG derivative or NgR binding inhibitor can interfere with the ability of MAG or another NgR ligand to bind to NgR.

4. Competition Assays

Each of the above-described assays may be used to assess (and quantitate) the ability of a putative inhibitory MAG derivative or NgR binding inhibitor of the invention to compete with a known NgR ligand for neuron binding, NgR binding and/or neuronal growth inhibition (i.e., mediated by NgR activation). As will be readily appreciated by the skilled artisan, numerous combinations of full-length or truncated soluble fusions, or wild-type, mutated, altered or derivatized molecules (ligands or NgRs) may be used, as long as appropriate controls (e.g., in the presence and absence of the putative inhibitory molecule) are performed.

Production of Polypeptides

A polypeptide (including peptides) as defined herein may be produced recombinantly, as discussed in more detail below. A polypeptide of the invention may thus be isolated from a cell that expresses the protein, or may be chemically synthesized following the teachings of the specification and using methods well known to those having ordinary skill in the art.

Antibodies To MAG Derivatives, NgR Binding Inhibitors and NgR Activators

Antibodies

The polypeptides of this invention may be used to elicit polyclonal or monoclonal antibodies that bind to a polypeptide of this invention, as well as a fragment, mutein, homologous protein, analog, derivative or fusion protein thereof, using a variety of techniques well known to those of skill in the art. Antibodies directed against the polypeptides of this invention are immunoglobulin molecules or portions thereof that are immunologically reactive with the polypeptide of the present invention.

Antibodies directed against a polypeptide of the invention may be generated by immunization of a mammalian host. Such antibodies may be polyclonal or monoclonal. Preferably they are monoclonal. Methods to produce polyclonal and monoclonal antibodies are well known to those of skill in the art. For a review of such methods, see Harlow and Lane, *Antibodies: A Laboratory Manual* (1988) and Ausubel et al. supra, herein incorporated by reference. Determination of immunoreactivity with a polypeptide encoded by an essential gene may be made by any of several methods well known in the art, including by immunoblot assay and ELISA.

Monoclonal antibodies with affinities of $10^{-8}$ M or preferably $10^{-9}$ to $10^{-10}$ $M^{-1}$ or stronger are typically made by standard procedures as described, e.g., in Harlow and Lane, 1988. Briefly, appropriate animals are selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen. Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241, herein incorporated by reference. Also, recombinant immunoglobulins may be produced (see U.S. Pat. No. 4,816,567, herein incorporated by reference).

An antibody of this invention may also be a hybrid molecule formed from immunoglobulin sequences from different species (e.g., mouse and human) or from portions of immunoglobulin light and heavy chain sequences from the same species. An antibody may be a single-chain antibody or a humanized antibody. It may be a molecule that has multiple binding specificities, such as a bifunctional antibody prepared by any one of a number of techniques known to those of skill in the art including the production of hybrid hybridomas, disulfide exchange, chemical cross-linking, addition of peptide linkers between two monoclonal antibodies, the introduction of two sets of immunoglobulin heavy and light chains into a particular cell line, and so forth.

The antibodies of this invention may also be human monoclonal antibodies, for example those produced by immortalized human cells, by SCID-hu mice or other non-human animals capable of producing "human" antibodies, or by the expression of cloned human immunoglobulin genes. The preparation of humanized antibodies is taught by U.S. Pat. Nos. 5,777,085 and 5,789,554, herein incorporated by reference.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

In one preferred embodiment, an antibody of the present invention binds to a NgR activator. In a more preferred embodiment, the antibody binds to a polypeptide having an amino acid sequence selected from SEQ ID NOS: 23, 32 or 39 (peptides M461, N38 and 0231, respectively), or binds to a polypeptide that is fragment, mutein, homologous protein, derivative, analog or fusion protein thereof. Such antibodies will recognize a core NgR ligand binding site and as such, will disrupt NgR ligand-NgR interactions and thereby inhibit NgR signaling. They will also be useful diagnostic tools, especially when used in conjunction with monitoring the progress of a therapeutic method of the invention.

In another preferred embodiment, an antibody of the present invention binds to a MAG derivative or a NgR binding inhibitor. Antibodies directed against inhibitory molecules of the invention will be useful diagnostic tools, especially when used in conjunction with monitoring the progress of a therapeutic method of the invention.

Nucleic Acids Encoding MAG Derivatives and NgR Binding Inhibitors

In one aspect, the present invention provides a molecule comprising an isolated nucleic acid sequence which encodes a MAG derivative having at least one mutation in Ig-like domain 5 (Igd5) or in a region flanking (i.e., within about 10 amino acid residues on either side of) Igd5, wherein the mutation reduces or eliminates the ability of the derivative to regulate (e.g., inhibit or promote) neurite outgrowth compared to endogenous or soluble MAG without eliminating binding to neuronal surfaces. In a preferred embodiment, nucleic acid sequences encoding the MAG derivative are derived from rat, murine or human MAG sequences having a least one mutation in or flanking Igd5 (nucleic acid residues 1456-1626 of SEQ ID NO: 1 [rat MAG]; nucleic acid residues 1444-1614 of SEQ ID NO: 3 [murine MAG]; or nucleic acid residues 1443-1613 of SEQ ID NO: 5 [human MAG].

In one preferred embodiment, the molecule comprises nucleic acid sequences that encode a MAG derivative having a partial or total deletion of Ig-like domain 5 ("Igd5") (and/or sequences flanking Igd5, see supra). Preferably, the deletion removes one or more nucleotides in a region of MAG Igd5 which encodes amino acid residues 450 to 490 of SEQ ID NOs: 1, 3 or 5 [rat, murine, or human MAG proteins, respectively]. These residues are encoded by nucleic acid residues 1510-1632 of SEQ ID NO: 1 [rat MAG]; nucleic acid residues 1498-1620 of SEQ ID NO: 3 [murine MAG]; and nucleic acid residues 1497-1619 of SEQ ID NO: 5 [human MAG]. More preferably, the deletion removes one or more nucleic acid residues in a more conserved region of MAG Igd5 which encodes amino acid residues 466 to 478 of SEQ ID NOs: 1, 3 or 5 [rat, murine, or human MAG proteins, respectively]. These amino acid residues are encoded by nucleic acid residues 1558-1596 of SEQ ID NO: 1 [rat MAG]; nucleic acid residues 1546-1584 of SEQ ID NO: 3 [murine MAG]; and nucleic acid residues 1545-1583 of SEQ ID NO: 5 [human MAG]. Preferred nucleic acid molecules of this embodiment comprise nucleic acid sequences that encode deleted MAG polypeptides, including those which encode MAGΔd5, MAGΔ450-490 and MAGΔ466-478.

In another preferred embodiment, the molecule comprises isolated nucleic acid sequences that encode a MAG derivative having one or more point mutations in or flanking MAG Igd5. Preferred nucleic acid molecules of this embodiment encode MAG derivatives comprising one or more MAG point mutations selected from the group consisting of L431, K435, E445, N450, V451, T452, V453, N454, E455, T456, E457, R458, E459, F460, V461, Y462, S463, E464, R465, S466, G467, L468, L469, L470, T471, S472, I473, L474, T475, L476, R477, G478, Q479, A480, Q481, A482, P483, P484, R485, V486, I487, C488, T489, S490 and R491.

In a preferred embodiment, an isolated nucleic acid molecule of the invention comprises sequences that encode MAG derivatives that are soluble chimeric molecules preferably Ig-like domain 1 of MAG (which carries a sialic acid binding site), and further comprising at least one mutation in or flanking MAG Ig-like domain 5. Preferred nucleic acid molecules of the invention encode soluble MAG derivatives that comprise an immunoglobulin Fc domain or at least one Ig-like domain from a heterologous protein, e.g., from a sialoadhesin molecule.

In another embodiment, a nucleic acid molecule of the invention comprises isolated nucleic acid sequences that encode residues that make up a Nogo receptor ligand binding site ("NgR binding inhibitor"). In one preferred embodiment, the nucleic acid molecule comprises sequences that encode a peptide derived from MAG Ig-like domain 5 that can bind to NgR and compete with another NgR ligand (e.g., soluble or membrane-bound MAG, Nogo and OMgp) for NgR or neuron binding. In a more preferred embodiment, the nucleic acid molecule comprises sequences of at least fifteen, preferably eighteen to thirty, more preferably 33-45 and most preferably greater than 45 nucleic acid residues derived from a region of MAG Ig-like domain 5. Such nucleic acid molecules encode a peptide of at least five, preferably six to ten, more preferably eleven to fifteen and most preferably greater than fifteen contiguous amino acid residues, respectively, wherein the peptide reduces inhibition of neural growth and regeneration by MAG or myelin. Preferred nucleic acid molecules encode peptides selected from a region of MAG Ig-like domain 5 so that they bind to NgR but do not contain a stretch of amino acids sufficient for NgR activation. Preferred nucleic acid molecules of the invention comprise nucleic acid sequences that encode MAG amino acid residues 422-451 (M422) (encoded by nucleic acid residues 1426-1515 of SEQ ID NO: 1 [rat MAG]; nucleic acid residues 1414-1503 of SEQ ID NO: 3 [murine MAG]; and nucleic acid residues 1413-1502 of SEQ ID NO: 5 [human MAG]); MAG amino acid residues 433-457 (M433) (encoded by nucleic acid residues 1459-1533 of SEQ ID NO: 1 [rat MAG]; nucleic acid residues 1447-1521 of SEQ ID NO: 3 [murine MAG]; and nucleic acid residues 1446-1520 of SEQ ID NO: 5 [human MAG]); MAG amino acid residues 442-471 (M442) (encoded by nucleic acid residues 1486-1573 of SEQ ID NO: 1 [rat MAG]; nucleic acid residues 1474-1561 of SEQ ID NO: 3 [murine MAG]; and nucleic acid residues 1473-1560 of SEQ ID NO: 5 [human MAG]); and MAG amino acid residues 462-486 (M462) (encoded by nucleic acid residues 1546-1620 of SEQ ID NO: 1 [rat MAG]; nucleic acid residues 1558-1632 of SEQ ID NO: 3 [murine MAG]; and nucleic acid residues 1557-1631 of SEQ ID NO: 5 [human MAG]).

Other preferred nucleic acid molecules of the invention comprise isolated nucleic acid sequences that encode MAG amino acid residues 437-441 (M437) (encoded by nucleic acid residues 1471-1485 of SEQ ID NO: 1 [rat MAG]; nucleic acid residues 1459-1473 of SEQ ID NO: 3 [murine MAG]; and nucleic acid residues 1458-1472 of SEQ ID NO: 5 [human MAG]); MAG amino acid residues 446-455 (M446) (encoded by nucleic acid residues 1498-1527 of SEQ ID NO: 1 [rat MAG]; nucleic acid residues 1486-1515 of SEQ ID NO: 3 [murine MAG]; and nucleic acid residues 1485-1514 of SEQ ID NO: 5 [human MAG]); and MAG amino acid residues 450-455 (M450) (encoded by nucleic acid residues 1510-1527 of SEQ ID NO: 1 [rat MAG]; nucleic acid residues 1498-1515 of SEQ ID NO: 3 [murine MAG]; and nucleic acid residues 1497-1514 of SEQ ID NO: 5 [human MAG]). See FIG. 15. Yet other preferred nucleic acid molecules of the invention comprise nucleic acid sequences that encode MAG amino acid residues 466-471 (M466) (encoded by nucleic acid residues 1558-1575 of SEQ ID NO: 1 [rat MAG]; nucleic acid residues 1546-1563 of SEQ ID NO: 3 [murine MAG]; and nucleic acid residues 1545-1562 of SEQ ID NO: 5 [human MAG]) and MAG amino acid residues 472-477 (M472) (encoded by nucleic acid residues 1576-1593 of SEQ ID NO: 1 [rat MAG]; nucleic acid residues 1564-1581 of SEQ ID NO: 3 [murine MAG]; and nucleic acid residues 1563-1580 of SEQ ID NO: 5 [human MAG]). See FIG. 18.

In another preferred embodiment of the invention, a nucleic acid molecule of the invention comprises isolated nucleic acid sequences that encode a NgR binding inhibitor derived from Nogo-66 (SEQ ID NO: 10) or Nogo-A (SEQ ID NO: 8) that has amino acid sequence similarity to MAG Ig-like domain 5, wherein the encoded peptide can bind to NgR and compete with another NgR ligand (e.g., soluble or membrane-bound MAG, Nogo and OMgp) for NgR or neuron binding. In a more preferred embodiment, the nucleic acid molecule comprises sequences of at least fifteen, preferably eighteen to thirty, more preferably 33-45 and most preferably greater than 45 nucleic acid residues derived from a region of Nogo-66 (SEQ ID NO: 10) or Nogo-A (SEQ ID NO: 8) that has amino acid sequence similarity to MAG Ig-like domain 5. Such nucleic acid molecules encode a peptide of at least five, preferably six to ten, more preferably eleven to fifteen and most preferably greater than fifteen contiguous amino acid residues, respectively, wherein the peptide blocks inhibition of neural growth and regeneration by MAG or myelin. Preferred nucleic acid molecules encode peptides selected from a region of Nogo-66 (or Nogo) so that they bind to NgR but do not contain a stretch of amino acids sufficient for NgR activation.

Preferred nucleic acid molecules of this embodiment of the invention comprise isolated nucleic acid sequences that encode a peptide comprising or consisting of Nogo-66 amino acid residues 13-17 (N13) (encoded by nucleic acid residues 3199-3213 of SEQ ID NO: 8 (human Nogo-A cDNA; Nogo-66 amino acid residues 22-31 (N22-1) (encoded by nucleic acid residues 3226-3255 of SEQ ID NO: 8; Nogo-66 amino acid residues 22-34 (N22-2) (encoded by nucleic acid residues 3226-3264 of SEQ ID NO: 8; Nogo-66 amino acid residues 26-31 (N26-1) (encoded by nucleic acid residues 3238-3255 of SEQ ID NO: 8; Nogo-66 amino acid residues 26-34 (N26-2) (encoded by nucleic acid residues 3238-3264 of SEQ ID NO: 8; Nogo-66 amino acid residues 9-33 (N-9-1) (encoded by nucleic acid residues 3187-3261 of SEQ ID NO:

8; and Nogo-66 amino acid residues 9-34 (N-9-2) (encoded by nucleic acid residues 3187-3264 of SEQ ID NO: 8). Other preferred nucleic acid molecules of the invention comprise nucleic acid sequences that encode a peptide comprising or consisting of Nogo-66 amino acid residues 42-47 (N42) (encoded by nucleic acid residues 3286-3303 of SEQ ID NO: 8; and Nogo-66 amino acid residues 48-53 (N48) (encoded by nucleic acid residues 3304-3321 of SEQ ID NO: 8).

In another preferred embodiment of the invention, a nucleic acid molecule of the invention comprises isolated nucleic acid sequences that encode a NgR binding inhibitor derived from OMgp that has amino acid sequence similarity to MAG Ig-like domain 5, wherein the encoded peptide can bind to NgR and compete with another NgR ligand (e.g., soluble or membrane-bound MAG, Nogo and OMgp) for NgR or neuron binding. In a more preferred embodiment, the nucleic acid molecule comprises sequences of at least fifteen, preferably eighteen to thirty, more preferably 33-45 and most preferably greater than 45 nucleic acid residues derived from a region of OMgp that has amino acid sequence similarity to MAG Ig-like domain 5. Such nucleic acid molecules encode a peptide of at least five, preferably six to ten, more preferably eleven to fifteen and most preferably greater than fifteen contiguous amino acid residues, respectively, wherein the peptide blocks inhibition of neural growth and regeneration by MAG or myelin. Preferred nucleic acid molecules encode peptides selected from a region of OMgp so that they bind to NgR but do not contain a stretch of amino acids sufficient for NgR activation. Preferred nucleic acid molecules of the invention comprise nucleic acid sequences that encode a peptide comprising or consisting of OMgp amino acid residues 206-210 (O206) (encoded by nucleic acid residues 740-754 of SEQ ID NO: 12 (murine OMgp); OMgp amino acid residues 215-224 (O215) (encoded by nucleic acid residues 767-796 of SEQ ID NO: 12; OMgp amino acid residues 219-224 (O219) (encoded by nucleic acid residues 719-796 of SEQ ID NO: 12; and OMgp amino acid residues 202-226 (O202) (encoded by nucleic acid residues 728-792 of SEQ ID NO: 12). Other preferred nucleic acid molecules of the invention comprise nucleic acid sequences that encode a peptide comprising or consisting of OMgp amino acid residues 235-240 (O235) (encoded by nucleic acid residues 827-844 of SEQ ID NO: 12; and OMgp amino acid residues 241-246 (O241) (encoded by nucleic acid residues 845-862 of SEQ ID NO: 12. See FIG. 18.

Nucleic Acids Encoding NgR Activators

In another embodiment, a nucleic acid molecule of the invention comprises isolated nucleic acid sequences that encode residues that make up a Nogo receptor ligand binding site ("NgR binding inhibitor") which activate NgR signaling. In one preferred embodiment, the nucleic acid molecule comprises sequences that encode a peptide derived from MAG Ig-like domain 5 that can bind to NgR and compete with another NgR ligand (e.g., soluble or membrane-bound MAG, Nogo and OMgp) for NgR or neuron binding. In a more preferred embodiment, the nucleic acid molecule comprises sequences of at least fifteen, preferably eighteen to thirty, more preferably 33-45 and most preferably greater than 45 nucleic acid residues derived from a region of MAG Ig-like domain 5. Such nucleic acid molecules encode a peptide of at least five, preferably six to ten, more preferably eleven to fifteen and most preferably greater than fifteen contiguous amino acid residues, respectively, wherein the peptide potentiates inhibition of neural growth and regeneration by MAG or myelin. Preferred nucleic acid molecules encode peptides selected from a region of MAG Ig-like domain 5 so that they bind to NgR and contain a stretch of amino acids sufficient for NgR activation. Preferred nucleic acid molecules of the invention comprise nucleic acid sequences selected from those that encode an NgR ligand (e.g., MAG, Nogo and OMgp) or alternatively, are derived from sequences that encode a consensus sequence derived from a comparison of such sequences (FIGS. 16 and 17; SEQ ID NO: 14).

Preferred nucleic acid molecule of the invention comprises nucleic acid sequences that encode MAG-derived peptides that comprise or consist of MAG amino acid residues 450-490 (encoded by nucleic acid residues 1510-1632 of SEQ ID NO: 1 [rat MAG]; nucleic acid residues 1498-1620 of SEQ ID NO: 3 [murine MAG]; and nucleic acid residues 1497-1619 of SEQ ID NO: 5 [human MAG]), preferably 462-490 (encoded by nucleic acid residues 1586-1632 of SEQ ID NO: 1 [rat MAG]; nucleic acid residues 1574-1620 of SEQ ID NO: 3 [murine MAG]; and nucleic acid residues 1573-1619 of SEQ ID NO: 5 [human MAG]), more preferably 466-478 (encoded by nucleic acid residues 1558-1594 of SEQ ID NO: 1 [rat MAG]; nucleic acid residues 1546-1582 of SEQ ID NO: 3 [murine MAG]; and nucleic acid residues 1545-1581 of SEQ ID NO: 5 [human MAG]), even more preferably 468-477 (encoded by nucleic acid residues 1564-1593 of SEQ ID NO: 1 [rat MAG]; nucleic acid residues 1552-1581 of SEQ ID NO: 3 [murine MAG]; and nucleic acid residues 1550-1580 of SEQ ID NO: 5 [human MAG]), and especially amino acid residues 474-476 (encoded by nucleic acid residues 1582-1590 of SEQ ID NO: 1 [rat MAO]; nucleic acid residues 1570-1578 of SEQ ID NO: 3 [murine MAG]; and nucleic acid residues 1569-1577 of SEQ ID NO: 5 [human MAG]). One preferred nucleic acid molecule encodes the NgR activator MAG(461-498) ("M461") (SEQ ID NO: 23), described above. This 38 amino acid peptide encompasses a region of MAG Igd5 (residues 466-478 of SEQ ID NOs: 2, 4 or 6) that is conserved among ligands of NgR (e.g., MAG, Nogo-66 and OMgp). See FIGS. 16 and 17.

The invention also provides nucleic acid molecules comprising or consisting of sequences that encode a MAG derivative polypeptide fragment which comprises MAG Ig-like domain 5 but lacks one or more of Ig-like domains 1-4 of MAG (i.e., an NgR activator). Preferred nucleic acid molecules of this embodiment encode "MAG(d3-5)", "MAG(d4-5)" and "MAG(d5)" constructs, where the recited MAG Ig-like domains are optionally constructed in the background of a chimeric fusion (see, e.g., FIG. 1 and Example 2: "MAG(3-5)", "Sn(1-3)MAG(4-5)", and "Sn(1-4)MAG(5)"), or as a soluble chimeric fusion (e.g., comprising an immunoglobulin Fc domain).

In another preferred embodiment, a nucleic acid molecule of the invention comprises or consists of sequences that encode a NgR activator of the invention comprising a peptide derived from Nogo-66 sequences (but excluding a full length Nogo extracellular domain, i.e., full-length Nogo-66) that can bind to and activate NgR signaling. Preferred nucleic acid molecules encode peptides selected from a region of Nogo having sequence similarity with MAG Ig-like domain 5 so that the encoded peptides bind to NgR and comprise a stretch of amino acids sufficient for NgR activation, whereby the peptide promotes inhibition of neural growth and regeneration by MAG or myelin. Preferred Nogo-derived peptides comprise or consist of Nogo-66 amino acid residues 26-66 (encoded by hNogo-A nucleotide residues 3238-3360 (SEQ ID NO: 8)), preferably 38-66 (encoded by hNogo-A nucleotide residues 3274-3360 (SEQ ID NO: 8)), more preferably 42-54 (encoded by hNogo-A nucleotide residues 3286-3324 (SEQ ID NO: 8)), even more preferably 44-53 (encoded by hNogo-A nucleotide residues 3292-3321 (SEQ ID NO: 8)), and especially amino acid residues 50-52 (encoded by hNogo-A nucleotide residues 3310-3318 (SEQ ID NO: 8)) of SEQ ID NO: 11.

In yet another preferred embodiment, a nucleic acid molecule of the invention comprises or consists of sequences that encode a NgR activator of the invention comprising a peptide derived from OMgp sequences (but excluding a full length OMgp extracellular domain) that can bind to and activate NgR signaling. Preferred nucleic acid molecules of this embodiment encode a peptide selected from a region of OMgp having sequence similarity with MAG Ig-like domain 5 selected so that it can bind to NgR and comprise a stretch of amino acids sufficient for NgR activation, whereby the peptide promotes inhibition of neural growth and regeneration by MAG or myelin. Preferred nucleic acid molecules of this embodiment encode OMgp-derived peptides that comprise or consist of OMgp amino acid residues 219-260 (encoded by nucleotide residues 779-904 of SEQ ID NO: 12), preferably 231-260 (encoded by nucleotide residues 815-904 of SEQ ID NO: 12), more preferably 235-247 (encoded by nucleotide residues 827-865 of SEQ ID NO: 12), more preferably 237-246 (encoded by nucleotide residues 833-862 of SEQ ID NO: 12), and especially amino acid residues 243-245 (encoded by nucleotide residues 851-859 of SEQ ID NO: 12) of SEQ ID NO:13.

Nucleic acid molecules of the invention which encode NgR activators, including peptides derived from MAG, Nogo-66, OMgp or the NgR ligand consensus sequence of FIG. 17, are expected to be useful for gene delivery methods that can trigger NgR signaling, and as such, will be useful for regulating neural sprouting and connectivity, e.g., for preventing aberrant sprouting and for preventing misconnections after injury, and for preventing pain and are thus also provided by the present invention. Nucleic acid molecule of the invention include those which comprise or consist of sequences that encode an inhibitory polypeptide (MAG derivative or NgR binding inhibitor) of an NgR activator of the invention—including those that comprise a fragment, fusion, mutein, allelic variant, analog or other derivative of MAG or other NgR ligand—as long as the encoded polypeptide is capable of competing with endogenous, membrane-bound or soluble MAG for neuron binding.

In another aspect, the invention provides a nucleic acid molecule comprising isolated sequences that are homologous to sequences encoding an inhibitory molecule (e.g., MAG derivative or NgR binding inhibitor) or an NgR activator of the invention. In a preferred embodiment, the nucleic acid molecule is homologous to a nucleic acid molecule encoding an inhibitory molecule comprising a polypeptide consisting of sequences selected from SEQ ID NOS: 15-22, 25-31, 33-40 (MAG, Nogo and OMgp derived NgR binding inhibitor peptides). In another preferred embodiment, the nucleic acid molecule is homologous to a nucleic acid molecule encoding a NgR activator of the invention comprising a polypeptide consisting of sequences selected from SEQ ID NO: 23 (activator peptide M461). In another preferred embodiment, the nucleic acid molecule encodes a polypeptide that comprises at least 3 and preferably 4 or more contiguous amino acid residues selected from the NgR ligand consensus sequence shown in FIGS. 16 and 17.

In a preferred embodiment, a homologous nucleic acid molecule is one that has at least 90% sequence identity with a nucleic acid molecule described herein, more preferably 95%, more preferably 97%, even more preferably 98%, and still more preferably 99%. Further, in one embodiment, a homologous nucleic acid molecule is homologous over its entire length to a nucleic acid molecule encoding an inhibitory molecule (MAG derivative or a NgR binding inhibitor) or NgR activator of the invention. In another preferred embodiment, a homologous nucleic acid molecule is homologous over only a part of its length to a nucleic acid molecule described herein, wherein the part is homologous to a nucleic acid encoding part or all of MAG Ig-like domain 5.

In yet another aspect, the invention provides a nucleic acid molecule that encodes a derivative or analog of an inhibitory molecule or NgR activator of the invention, e.g., a fusion protein, a homologous protein, a polypeptide fragment, a mutein, allelic variant, analog or derivative of the polypeptides of the invention, as described in detail above.

Methods of Using Nucleic Acid Molecules as Probes and Primers

In one embodiment, a nucleic acid molecule of the invention may be used as a probe or primer to identify or amplify a nucleic acid molecule that selectively hybridizes to the nucleic acid molecule. In a preferred embodiment, the probe or primer is derived from a nucleic acid molecule encoding MAG Ig-like domain 5, and more preferably, from the region of MAG which has detectable homology to OMgp and to Nogo-66 (see FIGS. 16 and 17). Using such a probe or primer, one may be able to identify other nucleic acid molecules encoding proteins that form domains that bind to NgR. Thus, in a preferred embodiment, the probe or primer is derived from nucleic acid residues encoding MAG Ig-like domain 5 (e.g., 1456-1626 of SEQ ID NO: 1 [rat MAG]; nucleic acid residues 1444-1614 of SEQ ID NO: 3 [murine MAG]; or nucleic acid residues 1443-1613 of SEQ ID NO: 5 [human MAG]). Preferably, the probe or primer is derived from nucleic acid residues encoding a region of MAG Igd5 which encodes amino acid residues 450 to 490 of SEQ ID NOs: 1, 3 or 5 [rat, murine, or human MAG proteins, respectively]. These residues are encoded by nucleic acid residues 1510-1632 of SEQ ID NO: 1 [rat MAG]; nucleic acid residues 1498-1620 of SEQ ID NO: 3 [murine MAG]; and nucleic acid residues 1497-1619 of SEQ ID NO: 5 [human MAG]. More preferably, the probe or primer is derived from nucleic acid residues encoding a more conserved region of MAG Igd5 from amino acid residues 466 to 478 of SEQ ID NOs: 1, 3 or 5 [rat, murine, or human MAG proteins, respectively]. These amino acid residues are encoded by nucleic acid residues 1558-1596 of SEQ ID NO: 1 [rat MAG]; nucleic acid residues 1546-1584 of SEQ ID NO: 3 [murine MAG]; and nucleic acid residues 1545-1583 of SEQ ID NO: 5 [human MAG].

In general, a probe or primer is at least 10 nucleotides in length, more preferably at least 12, more preferably at least 14 and even more preferably at least 16 nucleotides in length. In an even more preferred embodiment, the probe or primer is at least 18 nucleotides in length, even more preferably at least 20 nucleotides and even more preferably at least 22 nucleotides in length. Primers and probes may also be longer in length. For instance, a probe or primer may be 25 nucleotides in length, or may be 30, 40 or 50 nucleotides in length. Methods of performing nucleic acid hybridization using oligonucleotide probes are well-known in the art. See, e.g., Sambrook et al., supra. See, e.g., Chapter 11 and pages 11.31-11.32 and 11.40-11.44, which describes radiolabeling of short probes, and pages 11.45-11.53, which describes hybridization conditions for oligonucleotide probes, including specific conditions for probe hybridization (pages 11.50-11.51). Methods of performing PCR using primers are also well-known in the art. See, e.g., Sambrook et al., supra and Ausubel et al., supra. PCR methods may be used to identify and/or isolate allelic variants and fragments of the nucleic acid molecules of the invention; PCR may also be used to identify and/or isolate nucleic acid molecules that hybridize to the primers and that may be amplified, and may be used to isolate nucleic acid molecules that encode homologous proteins, analogs, fusion protein or muteins of the invention.

Vectors, Host Cells and Recombinant Methods of Producing Polypeptides

The present invention provides vectors that comprise nucleic acid molecules of the invention, and especially, vectors that can express inhibitory molecules (e.g., MAG derivatives and NgR binding inhibitors) or NgR activators of the invention in a host cell. The recombinant nucleic acid molecules and more particularly, the expression vectors of this invention may be used to express the inhibitory (e.g., MAG derivatives and NgR binding inhibitors) and NgR activator polypeptides of this invention as recombinant polypeptides in a heterologous host cell. Such polypeptides of this invention, including analogs, derivatives and muteins as described herein, may be recombinantly expressed from the nucleic acid sequences according to this invention using skills well known in the art, as summarized below.

Nucleic acid sequences may be expressed by operatively linking them to an expression control sequence in an appropriate expression vector and employing that expression vector to transform an appropriate unicellular host. Expression control sequences are sequences which control the transcription, post-transcriptional events and translation of nucleic acid sequences. Such operative linking of a nucleic sequence of this invention to an expression control sequence, of course, includes, if not already part of the nucleic acid sequence, the provision of a translation initiation codon, ATG or GTG, in the correct reading frame upstream of the nucleic acid sequence.

A wide variety of host/expression vector combinations may be employed in expressing the nucleic acid sequences of this invention. Useful expression vectors, for example, may consist of segments of chromosomal, non-chromosomal and synthetic nucleic acid sequences. Useful expression vectors for bacterial and eukaryotic host cells, such as yeast or mammalian cells, may be used and are well known in the art. Expression in mammalian cells, for example, can be achieved using a variety of plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL941. (See below for a more detailed discussion on gene delivery using viral vectors).

In addition, any of a wide variety of expression control sequences may be used in these vectors to express the DNA sequences of this invention. A multitutde of xpression control sequences are available in the art and may be selected to direct appropriate expression of the nucleic acids and/or polypeptides of the invention. Some such control sequences are described, e.g., in Goeddel; Gene Expression Technology: Methods in Enzymology 185, Academic Press, San Diego, Calif. (1990). For instance, any of a wide variety of expression control sequences-sequences that control the expression of a DNA sequence when operatively linked to it may be used in vectors to express sequences encoding the polypeptides of this invention. Expression control sequences that control transcription include, e.g., promoters, enhancers and transcription termination sites. Expression control sequences in eukaryotic cells that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct targeted expression of the polypeptide to or within particular cellular compartments, and sequences in the 5' and 3' untranslated regions that modify the rate or efficiency of translation and/or mRNA degradation.

Many examples of useful expression control sequences—including constitutive, inducible and tissue-specific promoter and/or enhancer sequences—are known to control the expression of genes of prokaryotic or eukaryotic cells and their viruses. Promoters suitable for use with prokaryotic hosts include the regulated beta-lactamase, lactose, tryptophan (trp) and lambda phage promoter systems, alkaline phosphatase, and hybrid promoters such as the tac promoter. Promoters for use in bacterial systems will preferably contain a Shine-Dalgarno (S.D.) sequence operably linked to the DNA encoding the polypeptide of interest. Examples of suitable promoters for use in yeast hosts include the promoters for 3-phosphoglycerate kinase or other glycolytic enzymes. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

Transcription from vectors in mammalian host cells may be controlled, for example, by promoters obtained from the genomes of viruses such as polyoma virus, fowlpox virus, adenovirus (such as Adenovirus 2 or 5), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems. Other useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage 1, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof.

Transcription of a DNA encoding a polypeptide of the invention by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus (CMV) immediate early promoter/enhancer, the polyoma enhancer on the late side of the replication origin, and adenovirus enhancers. The enhancer may be spliced into the vector at a position 5' or 3' to the coding sequence of interest, but is preferably located at a site 5' from the promoter.

In a preferred embodiment, the promoter and/or regulatory sequences are designed specifically for expression (preferably regulated expression) in a cell of the nervous system, e.g., a neural or glial cell. In a more preferred embodiment, the promoter is a neural specific promoter, e.g., a neural specific enolase promoter. Other neural specific promoters are known in the art (see, e.g., U.S. Pat. Nos. 6,066,726 and 5,753,502). Thus, in a preferred embodiment, the nucleic acid of the invention is operably linked to at least one transcriptional regulatory sequence which is useful for treating or preventing an injury, condition or disease in a patient characterized by diminished potential for axonal growth.

Expression vectors used in eukaryotic host cells (yeast, fungi, insect, plant, animal, human, or nucleated cells from other multicellular organisms) will preferably also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide of the invention.

Preferred nucleic acid vectors also include a selectable and optionally, an amplifiable marker gene (e.g., DHFR) and means for amplifying the copy number of the gene of interest. Such marker genes are well-known in the art. Nucleic acid vectors may also comprise stabilizing sequences (e.g., ori- or ARS-like sequences and telomere-like sequences), or may alternatively be designed to favor directed or non-directed integration into the host cell genome.

In a preferred embodiment, nucleic acid sequences of this invention are inserted in frame into an expression vector that allows high level expression of an RNA which encodes a protein comprising the encoded nucleic acid sequence of interest. Nucleic acid cloning and sequencing methods are well known to those of skill in the art and are described in an assortment of laboratory manuals, including Sambrook et al., supra; and Ausubel et al., supra. Product information from manufacturers of biological, chemical and immunological reagents also provide useful information.

Of course, not all vectors and expression control sequences will function equally well to express the nucleic acid sequences of this invention. Neither will all hosts function equally well with the same expression system. However, one of skill in the art may make a selection among these vectors, expression control sequences and hosts without undue experimentation and without departing from the scope of this invention. In selecting an expression control sequence, a variety of factors should also be considered. These include, for example, the relative strength of the sequence, its controllability, and its compatibility with the nucleic acid sequence of this invention, particularly with regard to potential secondary structures. The design of the expression vector may also depend on such factors as the choice of the host cell to be transformed and/or the type of protein desired to be expressed. Moreover, the copy number and ability to control the copy number of the vector and the expression of any other proteins encoded by the vector, such as markers, should also be considered.

Unicellular hosts (e.g., bacteria, yeasts, and animal or plant cells in culture) should be selected by consideration of their compatibility with the chosen vector, the toxicity of the product coded for by the nucleic acid sequences of this invention, their secretion characteristics, their ability to fold the polypeptide correctly, their fermentation or culture requirements, and the ease of purification from them of the products coded for by the nucleic acid sequences of this invention.

Suitable host cells for the expression of polypeptides of the invention are derived from multicellular organisms. Examples of invertebrate cells include insect cells such as Drosophila S2 and Spodoptera Sf9, as well as plant cells. Examples of useful mammalian host cell lines include but are not limited to Chinese hamster ovary (CHO) and COS cells. Other examples include monkey kidney CV1 line transformed by SV40 (COS-7, ATCC CRL 1651); human embryonic kidney line (293 or 293 cells selected for growth in suspension culture); CHO cells lacking a functional DHFR gene (e.g., Urlaub and Chasin, Proc. Natl. Acad. Sci. USA, 77:4216 (1980)); mouse sertoli cells (e.g., TM4); human lung cells (W138, ATCC CCL 75); human liver cells (e.g., Hep G2, BB 8065); and mouse mammary tumor cells (e.g., MMT 060562, ATCC CCL51). Human stem cells (see, e.g., U.S. Pat. Nos. 6,245,566 and 6,090,622) and particularly neural stem cells and associated delivery systems (see, e.g., U.S. 20020164309 and 20020064873) may also be used in accordance with the invention. The selection of appropriate host cells takes into consideration the vector on which the nucleic acid of the invention is carried and is within the skill in the art.

Transformation and other methods of introducing nucleic acids into a host cell (e.g., conjugation, protoplast transformation or fusion, transfection, electroporation, liposome delivery, membrane fusion techniques, high velocity DNA-coated pellets, viral infection and protoplast fusion) can be accomplished by a variety of methods which are well known in the art (see, for instance, Ausubel, supra, and Sambrook et al., supra). Depending upon the host cell, vector, and method of transformation used, transient or stable expression of the polypeptide will be constitutive or inducible. One having ordinary skill in the art will be able to decide whether to express a polypeptide transiently or in a stable manner, and whether to express the protein constitutively or inducibly.

Particular details of the transfection, expression and purification of recombinant proteins are well documented and are understood by those of skill in the art. Further details on the various technical aspects of each of the steps used in recombinant production of foreign genes in bacterial cell expression systems can be found in a number of texts and laboratory manuals in the art. See, e.g., Ausubel et al., supra, and Sambrook et al., supra, and Kieser et al., supra, herein incorporated by reference.

Transgenic Animals and Plants

Polypeptides of the invention (i.e., inhibitory molecules and NgR activators of the invention) may also be produced transgenically through the generation of a mammal or plant that is transgenic for the sequences of interest and production of the polypeptide in a recoverable form therefrom. In connection with the transgenic production in mammals, inhibitory molecules (MAG derivatives and NgR binding inhibitors) and NgR activators of the invention can be produced in, and recovered from, the milk of goats, cows, or other mammals. See, e.g., U.S. Pat. Nos. 5,827,690, 5,756,687, 5,750, 172, and 5,741,957. See also, e.g., U.S. Pat. Nos. 6,448,469 and 6,441,145 for production of membrane proteins in milk.

In some embodiments, non-human transgenic animals or plants are produced by introducing one or more nucleic acid molecules encoding a polypeptide of the invention into the animal or plant by standard transgenic techniques. See Hogan and U.S. Pat. No. 6,417,429. The transgenic cells used for making the transgenic animal can be embryonic stem cells or somatic cells. The transgenic non-human organisms can be chimeric, nonchimeric heterozygotes, and nonchimeric homozygotes. See, e.g., Hogan et al., *Manipulating the Mouse Embryo: A Laboratory Manual* 2ed., Cold Spring Harbor Press (1999); Jackson et al., *Mouse Genetics and Transgenics: A Practical Approach*, Oxford University Press (2000); and Pinkert, *Transgenic Animal Technology: A Labo-*

*ratory Handbook*, Academic Press (1999). In some embodiments, the transgenic non-human animals have a targeted disruption and replacement by a targeting construct that encodes a polypeptide of interest. The polypeptides of the invention may be made in any transgenic animal. In a preferred embodiment, the non-human animals are mice, rats, sheep, pigs, goats, cattle or horses. The non-human transgenic animal expresses said encoded polypeptides in blood, milk, urine, saliva, tears, mucus and other bodily fluids. Nucleic acids of the invention, or modified forms thereof, can also be used to generate either transgenic animals or "knock out" animals which, in turn, are useful in the development and screening of therapeutically useful reagents. A transgenic animal (e.g., a mouse, rat, pig, cow or goat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. Methods for generating transgenic animals, particularly animals such as mice or rats, have become conventional in the art and are described, for example, in U.S. Pat. Nos. 4,736,866 and 4,870,009. Typically, particular cells would be targeted for transgene incorporation with tissue-specific enhancers. Transgenic animals that include a copy of a transgene encoding a polypeptide of the invention introduced into the germ line of the animal at an embryonic stage can be used to examine the effect of increased expression of the trangene and its product (i.e., a MAG derivative, NgR binding inhibitor or NgR activator) in an animal. Such animals can be used as tester animals for reagents thought to influence, for example, pathological conditions associated with aberrant NgR signaling. In accordance with this facet of the invention, an animal is treated with the reagent and a reduced incidence of the pathological condition, compared to untreated animals bearing the transgene, would indicate a potential therapeutic intervention for the pathological condition.

Pharmaceutical Compositions and Treatments Using MAG Derivatives, NgR Binding Inhibitors and NgR Activators The inhibitory molecules (MAG derivatives and NgR binding inhibitors) and NgR activators of this invention may be formulated into pharmaceutical compositions and administered in vivo at an effective dose to treat the particular clinical condition addressed. Administration of one or more of the pharmaceutical compositions according to this invention will be useful for regulating and for promoting neural growth or regeneration in the nervous system, for treating injuries or damage to nervous tissue or neurons, and for treating neural degeneration associated with traumas to the nervous system, disorders, conditions or diseases. Such traumas, conditions, diseases, disorders or injuries include, but are not limited to: cranial or cerebral trauma, aneurysms, strokes, spinal cord injury, Alzheimer's disease, Parkinson's disease, Creutzfeldt-Jacob disease, kuru, Huntington's disease, multiple system atrophy, amyotropic lateral sclerosis (Lou Gehrig's disease), progressive supranuclear palsy, and demyelinating diseases including multiple sclerosis, monophasic demyelination, encephalomyelitis, multifocal leukoencephalopathy, panencephalitis, Marchiafava-Bignami disease, pontine myelinolysis, adrenoleukodystrophy, Pelizaeus-Maerzbacher disease, Spongy degeneration, Alexander's disease, Canavan's disease, metachromatic leukodystrophy and Krabbe's disease.

The compositions of this invention may be administered alone or in combination with one or more therapeutic or diagnostic agents. For example, the compositions of this invention may be administered together with but not limited to, e.g., anti-inflammatory agents, anticoagulants, antithrombotics, or tissue plasminogen activators.

The patient to be treated may be a human or a veterinary animal.

Determination of a preferred pharmaceutical formulation and a therapeutically efficient dose regiment for a given application is within the skill of the art taking into consideration, for example, the condition and weight of the patient, the extent of desired treatment and the tolerance of the patient for the treatment.

Administration of the MAG derivative, NgR binding inhibitors and NgR activators of this invention, including isolated and purified forms, their salts or pharmaceutically acceptable derivatives thereof, may be accomplished using any of the conventionally accepted modes of administration of agents which are used to treat neuronal injuries or disorders.

In one embodiment of the invention, cells which have been engineered to express one or more inhibitory molecules or NgR activators of the invention may be used in therapeutic treatment regimes. Such engineered cells may be used to synthesize a therapeutic agent which can then be administered independently to a host. Alternatively, cells transformed, transfected, or infected with exogenous nucleic acid such as DNA or RNA that expresses an inhibitory or activator molecule of the invention that is secreted or released from the engineered cell may be used directly as a therapeutic, e.g., by implanting such engineered cells into a host at a region which is in communication with the targeted tissue or cells in need of treatment.

Soluble inhibitory (MAG derivative and NgR binding inhibitors) and NgR activator molecules such as those described herein can be prepared from the culture media of transfected cells, e.g., COS cells (fibroblasts) transfected with expression plasmids encoding a soluble inhibitory molecule (e.g., a soluble MAG-Fc derivative having at least one mutation in MAG Ig-like domain 5) which is secreted by these cells. It is anticipated that, as has been carried out for hybridoma cells that secrete antibodies (Schnell, L. and Schwab, M. E., *Nature*, 343, pp. 269-72 (1990); Schnell et al., *Nature*, 367, pp. 170-73 (1993), COS cells or other transfectants secreting a soluble molecule of the invention, such as a MAG derivative or a NgR binding inhibitor peptide, may be implanted into damaged spinal cord. The cells will secrete the inhibitory molecule, which reduces or prevents endogenous MAG from interacting with the neuronal surface, reduces or prevents MAG and other endogenous NgR ligands (Nogo and OMgp) from binding and activating NgR signaling, and thereby reduces or prevents inhibition of axonal growth and regeneration by endogenous MAG and other myelin inhibitors.

Viral or non-viral gene delivery into cells which then over (or under) express an inhibitory or activator molecule of the invention may be performed in vitro or in vivo by any of a number of techniques well known to those of skill in the art. A number of such delivery methods have been shown to work with neurons. See, e.g., US 20020168760 (Retroviral vectors for gene transfer into neuronal cells); US 20020168338 (DNA delivery to the central nervous system); Cherksey et al., U.S. Pat. No. 6,210,664 (Method for gene transfer to the central nervous system involving a recombinant retroviral expression vector); Kaplitt et al., U.S. Pat. No. 6,180,613 (AAV-mediated delivery of DNA to cells of the nervous system); Hayes et al., U.S. Pat. No. 6,096,716 (Liposome-mediated transfection of central nervous system cells); Kochanek et al, U.S. Pat. No. 5,981,225 (Gene transfer vector, recombinant adenovirus particles containing same, method for producing the same and method of use of the same); Gage et al., U.S. Pat. No. 5,762,926 (Method of grafting genetically modified cells to treat defects, disease or damage to the central nervous system); WO/008192 (Herpes viral vectors for gene delivery); and CA2247912 (Genetically engineered primary oligodendrocytes for transplantation-mediated gene delivery in the central nervous system); the entire disclosures of which are incorporated herein by reference.

Accordingly, the invention also provides means for delivery to a neural cell of an inhibitory molecule (MAG derivative or NgR binding inhibitor) or NgR activator of the invention. In one embodiment, a vector—and in another embodiment, a host cell—comprising a nucleic acid encoding a MAG derivative, NgR binding inhibitor or NgR activator is provided. As used herein the term "vector" refers to a molecule which carries a nucleic acid of the invention into a host cell and preferably, which enables the nucleic acid to be expressed in the host cell. Preferably, the host cell is a mammalian cell. In a preferred embodiment, the host cell is derived from (e.g., is a neuron or glial cell) or is otherwise introduced into the mammalian central nervous system.

For example, neuronal cells can be infected with a viral which causes the infected host cells to express a molecule (e.g., a polypeptide) of the invention at high levels. If the polypeptide of the invention is not normally a secreted protein, it can be engineered to possess a signal peptide required for secretion of a protein from a host cell. Such signal peptides are characterized by their length (about 16-30 amino acids) and hydrophobicity and which are not highly conserved at the amino acid sequence level (see, e.g., Lodish et al., Molecular Cell Biology, 3d ed., Scientific American Books, W.H. Freeman and Company, New York, 1995, Chapter 16). Amino acid residues which function as a signal sequence for secretion in a eukaryotic cell may be engineered onto the N-terminus of a heterologous protein by any of a number of routine genetic engineering methods well known to those of skill in the art. See, e.g., Farrell et al., Proteins, 41, pp. 144-53 (2000) (see also http://www.healthtech.com/2001/pex); Borngraber et al., Protein Expr. Purif., 14, pp. 237-46 (1998); Collins-Racie et al., Biotechnology, 13, pp. 982-987 (1995); U.S. Pat. No. 5,747,662; WO00/50616; WO99/53059; and WO96/27016; each of which is incorporated herein by reference in its entirety. Host cells which express a secreted form of a polypeptide of the invention would be expected to elevate levels of that polypeptide in the cerebrospinal fluid (CSF) which bathes the nervous system. Alternatively, it is possible to provide a molecule of the invention, e.g., by injection, directly to the CSF. Transfected cells, secreting other forms of a molecule of the invention, may be administered to a site of neuronal injury or degeneration in a similar manner.

Viral Vectors for Nucleic Acid Delivery In Vitro And In Vivo

Nucleic acid molecules of the invention may be administered in a biologically effective carrier, e.g. any formulation or composition capable of effectively delivering the nucleic acids to cells in vivo. Representative approaches include insertion of subject nucleic acid sequences into viral vectors, including but not limited to a recombinant retroviruses, adenovirus, adeno-associated virus, and herpes simplex virus-1, or other attenuated viruses, or recombinant bacterial or eukaryotic plasmids which can be taken up by a damaged axon. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or calcium phosphate precipitation carried out in vivo. The choice of a particular nucleic acid delivery system will depend on such factors as the intended target and the route of administration, e.g. locally or systemically. In a preferred embodiment, a vector construct is used in such a way that the expression product can cross the blood brain barrier. Furthermore, it will be recognized that vectors enabling in vivo regulation of expression are also useful for in vitro modulation of expression in cells, such as for use in ex vivo assay systems such as those described herein.

In addition, it is possible to target endogenous genes directly by homologous recombination techniques. Such techniques allow the skilled worker to replace or modify endogenous genes in a mammalian cell—for activation, inactivation or alteration of gene coding, including intracellular targeting sequences, and non-coding (regulatory) sequences, such as transcription control sequences and other regulatory sequences which control expression levels of a gene of interest. Accordingly, an inhibitory molecule comprising a MAG derivative having at least one mutation in MAG Ig-like domain 5, for example, may be constructed in a target cell using homologous recombination techniques. See, e.g., U.S. Pat. Nos. 6,214,622 and 6,054,288, which are incorporated herein by reference.

A nucleic acid molecule of the invention may be introduced into a cell in vivo using a viral vector comprising the nucleic acid, e.g. a DNA, encoding the particular form of the polypeptide desired. Infection of cells with a viral vector is an efficient way to introduce a desired nucleic acid molecule into a large proportion of targeted cells. In addition, sequences encoded by a viral vector are often expressed efficiently in infected cells. The specificity of viral gene delivery can be enhanced by the use of tissue- or cell-specific transcriptional regulatory sequences which control expression of the gene of interest residing in the viral vector (see supra).

One preferred viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, e.g., Berkner et al. *BioTechniques* 6:616(1988); Rosenfeld et al. *Science* 252:431-434(1991); and Rosenfeld et al. *Cell* 68:143-155(1992). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types (Rosenfeld et al. supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham J. Virol. 57:267 (1986)). Most replication-defective adenoviral vectors currently in use and therefore favored by the present invention are deleted for all or parts of the viral E1 and E3 genes but retain as much as 80% of the adenoviral genetic material (see, e.g., Jones et al. Cell 16:683(1979); Berkner et al., supra; and Graham et al. in Methods in Molecular Biology, E. J. Murray, Ed. (Humana, Clifton, N.J., 1991) vol. 7. pp. 109-127).

Expression of the inserted nucleic acid sequences can be under control of, for example, the E1A promoter, the major late promoter (MLP) and associated leader sequences, the E3 promoter, or exogenously added promoter sequences.

Another preferred viral vector system useful for delivery of the nucleic acid molecule of the invention is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. Curr. Topics in Micro. and Immunol. 158: 97-129(1992)). It is also one of the few viruses that may integrate its DNA into non-dividing cells, and exhibits a high frequency of stable integration (see for example Flotte et al. Am. J. Respir. Cell. Mol. Biol. 7:349-356(1992); Samulski et al. J. Virol. 63:3822-3828(1989); and McLaughlin et al. J. Virol. 62:1963-1973 (1989)). A variety of nucleic acids have been introduced into different cell types using AAV vectors (see for example Hermonat et al. Proc. Natl. Acad. Sci. USA 81:6466-6470(1984); Tratschin et al. Mol. Cell. Biol. 4:2072-2081(1985); Wondisford et al. Mol. Endocrinol. 2:3239(1988); Tratschin et al. J. Virol. 51:611-619 (1984); and Flotte et al. J. Biol. Chem. 268:3781-3790(1993)).

Yet another preferred viral vector system useful for delivery of the nucleic acid molecule of the invention is a replication defective Herpes simplex virus-1 (HSV-1) vector, which has been shown to achieve efficient transduction and expression of heterologous genes in the nervous system (Dobson et al. Neuron. 5:353(1990); Federoff et al. Proc. Natl. Acad. Sci. U.S.A. 89:1636(1992); Andersen et al. Hum Gene Ther. 3:487(1992); Huang et al. Exp Neurol. 115:303(1992); Fink et al. Hum Gene Ther. 3:11(1992); Breakefield et al. in Gene Transfer and Therapy in the Nervous System. Heidelberg, FRG: Springer-Verlagpp 45-48(1992); and Ho et al. Proc Natl. Acad. Sci U.S.A. 90:3655(1993)). HSV-2 vectors have also been described (Linnik et al. Stroke. 26:1670(1995); Lawrence et al. J. Neuroscience. 16:486(1996)).

Retrovirus vectors and adeno-associated virus (AAV) vectors are preferred vectors according to the invention for transferring nucleic acids encoding inhibitory molecules and NgR activators of the invention into cells in vivo, particularly into human cells. These vectors provide efficient delivery of genes into cells, and the transferred nucleic acids are stably integrated into the chromosomal DNA of the host. The development of specialized cell lines ("packaging cells") that produce replication-defective retroviruses are especially preferred for gene therapy applications (see, e.g., Miller, A. D. Blood 76:271(1990)). Recombinant retrovirus may be constructed in which part of the retroviral coding sequence (gag, pol, env) has been replaced by nucleic acid encoding one of the subject receptors rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses may be found, e.g., in Current Protocols in Molecular Biology, Ausubel, F. M. et al. (eds.) Greene Publishing Associates, (1989), Sections 9.10-9.14 and other standard laboratory manuals. Representative examples of retroviruses include pLJ, pZIP, pWE and pEM which are well known to those skilled in the art. Representative examples of packaging virus lines for preparing both ecotropic and amphotropic retroviral systems include psi.Crip, psi.Cre, psi 2 and psi.Am. Retroviruses have been widely used to introduce a variety of genes into many different cell types in vitro and/or in vivo. Moreover, it is useful to limit the infection spectrum of retroviruses and retroviral-based vectors by modifying the viral packaging proteins on the surface of the viral particle (see, for example PCT publications WO93/25234 and WO94/06920; Roux et al. PNAS 86:9079-9083(1989); Julan et al. J. Gen Virol 73:3251-3255(1992); and Goud et al. Virology 163: 251-254(1983)); Neda et al. J. Biol Chem 266:14143-14146 (1991)).

Inhibitory molecules and NgR activators of this invention can be delivered by spinal implantation (e.g., into the cerebrospinal fluid) of cells or other biocompatible materials engineered to release or secrete such molecules according to this invention. Cell secretion rates or material release rates of the agent are measured in vitro (e.g., in cell culture where applicable) and then extrapolated based on relative volumes, in vivo half-lives, and other parameters understood by those of skill in the art. For example, about $5 \times 10^7$ transfected COS cells will secrete about 1 mg of an inhibitory MAG derivative over a 5-day period. A concentration of 50 µg/ml of an inhibitory MAG derivative effectively reverses the inhibitory effects of wild-type MAG. Finally, within the perineurium of an adult rat spinal cord is a volume of about 0.5 ml. Therefore, if $2 \times 10^6$ MAG derivative-secreting COS cells are implanted into an injured spinal cord, then the concentration of MAG-Fc inhibitory derivative should be maintained at about 400 µg/ml, i.e., 8-fold more concentrated than the concentration shown herein to be effective in cultured cells. Finally, calculations to correct for the difference between the volume of the perineurium of an adult rat spinal cord compared to the subject being treated can be made by one of skill in the art.

Optionally, transfected cells that release or secrete one or more molecules or the invention may be encapsulated into immunoisolatory capsules or chambers and implanted into the brain or spinal cord region using available methods that are known to those of skill in the art. See, e.g., U.S. Pat. Nos. 6,179,826, 6,083,523; 5,676,943; 5,653,975; 5,487,739; 4,298,002; 4,670,014; and U.S. Pat. No. 5,487,739; WO 89/04655; WO 92/19195; WO93/00127; and references cited therein, all of which are incorporated herein by reference.

Alternatively, for inhibitory molecules (e.g., MAG derivatives and NgR binding inhibitors) or NgR activators that are not secreted by transfected cells, a pump and catheter-like device may be used. A pump, such as one designed for subcutaneous administration, and/or a catheter-like device may be implanted at or inserted into the site of injury, e.g., subcutaneously or intrathecally, to administer an inhibitory or activator molecule of the invention on a timely basis and at the desired concentration, which can be selected and empirically modified by one of skill in the art. Such pharmaceutical delivery systems are well known to those of skill in the art. See, e.g., U.S. Pat. No. 4,578,057 and references cited therein; for implantable pumps, see, e.g., http://www.medtronic.com); which are each incorporated herein by reference.

If the molecule of the invention is capable of crossing the blood brain barrier, it may be administered using a pump and catheter-like device implanted at or inserted at a location distant from the site of injury on a timely basis and at the desired concentration, which can be selected and empirically modified by one of skill in the art. If the molecule of the invention does not cross the blood brain barrier, it can be delivered intrathecally using a pump and catheter-like device either close to or at a distance from the lesion site. Accordingly, in another aspect, the invention provides a pump containing an inhibitory molecule (MAG derivative or NgR binding inhibitor) or NgR activator of the invention.

Inhibitory molecules and NgR activators of the invention may be administered, alone or in combination with one or more agents that provide an environment favorable to axonal growth, by a variety of means. In one embodiment, they may be incorporated into or administered in conjunction with a vector of the invention. In another embodiment, they may be injected, either locally or systemically, and are preferably co-administered with a molecule or composition of the invention. In yet another embodiment, such agents may be supplied in conjunction with nerve guidance channels as described in U.S. Pat. Nos. 5,092,871 and 4,955,892. Examples of classes of such agents include trophic factors, receptors, extracellular matrix proteins, or intrinsic factors. Exemplary trophic factors include but are not limited to NGF, BDNF, NT-3, -4, -5, or -6, CNTF, LIF, IGFI, IGFII, GDNF, GPA, bFGF, TGFb, and apolipoprotein E. Exemplary receptors include but are not limited to the Trk family of receptors. An exemplary extracellular matrix protein is laminin. Exemplary intrinsic factors include but are not limited to GAP-43 and ameloid precursor protein (APP). Exemplary adhesion molecules include but are not limited to NCAM and L1.

The pharmaceutical compositions of this invention may be in a variety of forms, which may be selected according to the preferred modes of administration. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The inhibitory and activator molecules of this invention may, for example, be placed into sterile, isotonic formulations with or without cofactors which stimulate uptake or stability. The formulation is preferably liquid, or may be lyophilized powder. For example, the inhibitory and activator molecules may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

The pharmaceutical compositions of this invention may also be administered using microspheres, liposomes, other microparticulate delivery systems or sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773,319; EP 58,481), copolymers of L-glutamic acid and gamma ethyl-L-glutamate (Sidman et al., *Biopolymers,* 22, pp. 547-56 (1985)); poly(2-hydroxyethyl-methacrylate) or ethylene vinyl acetate (Langer et al., *J. Biomed. Mater. Res.,* 15, pp. 167-277 (1981); Langer, *Chem. Tech.,* 12, pp. 98-105 (1982)).

Liposomes containing inhibitory and activator molecules of the invention can be prepared by well-known methods (See, e.g. DE 3,218,121; Epstein et al., *Proc. Natl. Acad. Sci. U.S.A.,* 82, pp. 3688-92 (1985); Hwang et al., *Proc. Natl. Acad. Sci. U.S.A.,* 77, pp. 4030-34 (1980); U.S. Pat. Nos. 4,485,045 and 4,544,545). Ordinarily the liposomes are of the small (about 200-800 Angstroms) unilamellar type in which the lipid content is greater than about 30 mol. % cholesterol. The proportion of cholesterol is selected to control the optimal rate of inhibitory and activator molecule release.

The inhibitory and activator molecules of this invention may also be attached to liposomes, which may optionally contain other agents to aid in targeting or administration of the compositions to the desired treatment site. Attachment of inhibitory and activator molecules to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., *J. Cell. Biochem.* Abst. Suppl. 16E 77 (1992)).

Utility of MAG Derivatives, NgR Binding Inhibitors and NgR Activators

The identification of inhibitory molecules that can reduce inhibition of neuronal growth and regeneration by myelin and its associated components has significant potential clinical use in the situations of nervous system injury—both of the peripheral and central nervous systems—and in particular for CNS injury. The mammalian central nervous system does not regenerate after injury even though there are many molecules present that promote and encourage a nerve to grow. The result is paralysis or brain damage. It has been shown that there are molecules present in the adult CNS that will actively prevent a nerve from regenerating. Three such neuron-inhibitory molecules have been identified: MAG, Nogo and OMgp. It had also been shown that all three molecules bind to the NgR receptor to exert their inhibitory effects. Furthermore, the binding sites of all three molecules on the NgR receptor overlap such that preventing the binding of one of these molecules will likely block binding of the other two. The present invention provides inhibitory molecules that are capable of blocking the inhibitory effects of MAG and it is anticipated that these MAG inhibitors will also be capable of preventing Nogo and OMgp from exerting their inhibitory effects. Thus, the inhibitory molecules (e.g., MAG derivatives and NgR binding inhibitors) of this invention are useful for promoting nerve growth, regeneration and repair.

It is anticipated that in vivo, after injury, application of inhibitory molecule of the invention will block the inhibitory effects of MAG and/or other inhibitory molecules, e.g., Nogo or OMgp, that act through a common receptor, e.g., the NgR receptor, and encourage axonal regeneration to proceed. The use of inhibitory molecules and NgR activators of the invention as a guidance cue in precise regions of the regenerating nervous system to keep growing axons on the correct path and moving towards the correct target is also contemplated.

The following are examples which illustrate the compositions and methods of this invention. These examples should not be construed as limiting: the examples are included for the purposes of illustration only.

EXAMPLE 1

Isolation of Cerebellar Neurons

Cerebellar neurons were isolated essentially as described in Doherty et al., *Nature,* 343, pp. 464-66 (1990); *Neuron,* 5, pp. 209-19 (1990); and Kleitman et al., *Culturing Nerve Cells*, pp. 337-78, MIT Press, Cambridge, Mass./London, England (G. Banker and K. Goslin, Eds.) (1991). Briefly, for animals up to nine days of age, the cerebellum was removed from two animals, and placed in 5 ml of 0.025% trypsin in PBS, triturated, and incubated for a further 10 minutes (min) at 37° C. Trypsinization was stopped by addition of 5 ml DMEM containing 10% fetal calf serum (FCS) and cells were centrifuged at 800 rpm for 6 min. The cells were resuspended to a single cell suspension in 2 ml of SATO containing 2% FCS.

EXAMPLE 2

Neurite Outgrowth Assays on Transfected CHO cells

Production of MAG and MAG Derivatives

Expression plasmids comprising a dhfr gene and, in a 5'-3' orientation, a cDNA encoding either full-length MAG containing all five Ig-like domains ("MAG"), internally deleted MAG containing Ig-like domains 1-3 ("MAG(1-3)" in FIG. 1; see "MAG(d1-3)-TM" below); truncated MAG containing Ig-like domains 3-5 ("MAG(3-5)" in FIG. 1; see "MAG(d3-5)-TM", below); chimeric MAG containing Sn Ig domains 1-3 fused to MAG Ig domains 4 and 5 ("Sn(1-3)MAG(4-5)" in FIG. 1;), chimeric MAG containing Sn Ig domains 1-3 fused to MAG Ig domain 4 fused to Sn domain 5 (Sn(1-3)MAG(4)Sn(5)), and chimeric MAG containing Sn Ig domains 1-4 fused to MAG Ig domain 5 (Sn(1-4)MAG(5)) were constructed, as described below.

MAG(d1-3)-TM (referred to as "MAG(1-3)" in FIG. 1); contains murine MAG Ig-like domains 1-3 fused to the murine MAG transmembrane domain. DNA composition: murine MAG nucleotide residues 160-1077 (SEQ ID NO: 3) fused to murine MAG nucleotide residue 1627 (SEQ ID NO: 3) in cloning vector "pECE" (Invitrogen, Carlsbad, Calif.). This nucleic acid fusion encodes a MAG fusion protein comprising murine MAG amino acid residues 4 (Leu)-309 (Asn) fused to amino acid residues 493 (Leu)-582 (His) (SEQ ID NO: 4).

MAG(d3-5)-TM (referred to as "MAG(3-5)" in FIG. 1); contains murine MAG Ig-like domains 3-5 and the adjacent MAG transmembrane domain. DNA composition: murine MAG nucleotide residues 943-(SEQ ID NO: 3) in cloning vector "pECE" (Invitrogen, Carlsbad, Calif.). This nucleic acid fusion encodes a MAG fusion protein comprising murine MAG amino acid residues 265 (Ser)-582 (His), which includes the MAG transmembrane domain amino acid residues 493 (Leu)-582 (His) (SEQ ID NO: 4).

Sn(d1-3)MAG(d4,5)-TM (referred to as "Sn(1-3)MAG(4-5)" in FIG. 1); contains the murine sialoadhesin protein Ig-like domains 1-3 fused to rat MAG Ig-like domains 4 and 5 and the adjacent MAG transmembrane domain. DNA composition: murine sialoadhesin nucleotide residues 529-1640 fused to rat MAG nucleotide residues 1132-2043 (SEQ ID NO: 1). This nucleic acid fusion encodes a MAG fusion protein comprising sialoadhesin amino acid residues 1 (Met)-325 (Phe) fused to rat MAG amino acid residues 324 (Tyr)-626 (Lys) (SEQ ID NO: 2).

Sn(d1-3)MAG(d4)Sn(d5)-TM (referred to as "Sn(1-3)MAG(4)Sn(5)" in FIG. 1); contains, in sequential order, the murine sialoadhesin protein Ig-like domains 1-3 fused to rat MAG Ig-like domain 4 fused to murine sialoadhesin protein Ig-like domain 5 fused to the rat MAG transmembrane domain. DNA composition: murine sialoadhesin nucleotide residues 529-1640 fused to rat MAG nucleotide residues 1132-1395 (SEQ ID NO: 1) fused to murine sialoadhesin nucleotide residues 1902-2204 fused to rat MAG nucleotide residues 1663-2043 (SEQ ID NO: 1). This nucleic acid fusion encodes a MAG fusion protein comprising sialoadhesin amino acid residues 1 (Met)-325 (Phe) fused to rat MAG amino acid residues 324 (Tyr)-411 (Phe) (SEQ ID NO: 2) fused to sialoadhesin amino acid residues 413 (Pro)-523 (Arg) fused to rat MAG amino acid residues 501 (Leu)-626 (Lys) (SEQ ID NO: 1.

Sn(d1-4)MAG(d5)-TM (referred to as "Sn(1-4)MAG(5)" in FIG. 1); contains the murine sialoadhesin protein Ig-like domains 1-4 fused to rat MAG Ig-like domain 5 and the adjacent MAG transmembrane domain. DNA composition: murine sialoadhesin nucleotide residues 529-1901 fused to rat MAG nucleotide residues 1396-2043 (SEQ ID NO: 1) subcloned into vector pcDNA3.1(+) (between HindIII and XbaI) (Invitrogen, Carlsbad, Calif.). This nucleic acid fusion encodes a MAG fusion protein comprising sialoadhesin amino acid residues 1 (Met)-412 (Pro) fused to rat MAG amino acid residues 412 (Ala)-626 (Lys) (SEQ ID NO: 2).

Briefly, chimeric Sn-MAG fusions were constructed as follows: Sn- and MAG-specific PCR primers having 15-20 nucleotides containing each individual fusion site were designed and produced by GibcoGRL. Fusion DNA fragments were generated by PCR amplification using fusion primers. PCR products were inserted into a pPCR-Script Amp SK(+) cloning vector using a PCR-Script Amp Cloning Kit (Stratagene #211188). Ampicillin-resistant cloning vectors carrying fusion DNA fragments were transformed into XL-10 Gold Kan ultracompetent cells (Stratagene, Inc.) and positive clones selected for ampicillin resistance (50 ug/ml). Plasmid DNA from positive clones was isolated and inserts analyzed by endonuclease digestions and DNA sequencing. Positive and verified clones were digested with restriction endonucleases and subcloned into pcDNA3.1 (+) (Invitrogen, Inc., Carlsbad, Calif.). Positive clones were selected for ampicillin resistance and plasmid DNA analyzed by restriction endonuclease digestion and DNA sequencing. DNA from verified subclones was isolated and used to transfect DG44 CHO cells, which were selected for G418 resistance. Details pertaining to the construction of each fusion protein are discussed below.

Sn(d1-3)MAG(d4,5)-TM: Sn-MAG chimeric nucleic acid sequences constructed by PCR as described above were first cloned in pPBK-CMV phagemid vector (Stratagene, #200403) and then subcloned into vector pcDNA3.1 (+) (between HindIII and XbaI) (Invitrogen, Inc., Carlsbad, Calif.).

Sn(d1-3)MAG(d4)Sn(d5)-TM: A DNA fragment containing the fusion (Sn(?-1640)-MAG(1132-1395)-Sn(1902-2204)-MAG(1663-?) was produced by PCR as described above. PCR products were inserted into a pPCR-Script Amp SK(+) cloning vector using PCR-Script Amp Cloning Kit (Stratagene #211188). Verified clones were digested with ScaI+XbaI, and the released DNA fragment purified and ligated into phagemid pPBK-CMV/Sn(d1-3)MAG(d4,5)TM (see above) previously linearized by digestion with endonucleases ScaI and XbaI and gel-purified. XL1-Blue MRF' ultracompetent *E. coli* cells (Stratagene) were transformed with the ligations and positive clones selected for ampicillin resistance. Verified clones were digested with HindIII and XbaI, ligated into the pcDNA3.1(+) plasmid (Invitrogen, Inc., Carlsbad, Calif.) between the HindIII and XbaI sites, and ligation reactions used to transform XL1-Blue ultracompetent cells (Stratagene). Plasmid DNA from verified subclones was isolated and used to transfect DG44 CHO cells, which were selected for G418 resistance. Sn(d1-4)MAG(d5)-TM: A DNA fragment containing the fusion Sn(d4)MAG(d5)-TM in the pPCR-Script Amp SK(+)vector was constructed as described above. The resulting plasmid was digested with restriction enzymes EcoRV and XbaI, and the released Sn(d4) MAG(d5)-TM fragment was gel-purified and inserted into a similarly digested (phosphatased) and gel-purified vector comprising a DNA fragment with Ig-like domains 1-4 of sialoadhesin (Sn(d1-4)) in pcDNA3.1(+) plasmid (Invitrogen, Inc., Carlsbad, Calif.) between the BamHI and EcoRV sites. The resulting subclone, plasmid "pcDNA3.1(+)/Sn(d1-4)MAG(d5)" was transfected into DG44 CHO cells as described above.

Expression of MAG, Truncated, Deleted or Chimeric MAG Derivatives by Transfected CHO Cells Chinese hamster ovary (CHO) cells deficient in the dihydrofolate reductase (dhfr) gene (Urlaub and Chasin, *Proc. Natl. Acad. Sci. USA,* 77, pp. 4216-20 (1980)) were transfected with each of the cDNA expression plasmids described above. Cells with multiple copies of dhfr were selected by growing in increasing concentrations of methotrexate, and the expression of MAG or MAG derivatives by individually transfected CHO cell lines were characterized as described in Mukhopadhyay et al., *Neuron,* 13, pp. 757-67 (1994), which is incorporated herein by reference. Transfected cells were maintained in DMEM supplemented with 10% dialyzed FCS, proline (40 mg/liter), thymidine (0.73 mg/liter), and glycine (7.5 mg/liter) at 37 C in 7.5% $CO_2$.

Neurite Outgrowth Assays

Confluent monolayers of control, MAG-, truncated MAG- or chimeric MAG-Sn-expressing CHO cells were established over a 24-hour (h) period in individual chambers of an 8-well tissue culture slide (Lab-Tek). Co-cultures were established as described previously (Doherty et al., *Nature,* 343, pp. 464-66 (1990); *Neuron,* 5, pp. 209-19 (1990); Mukhopadhyay et al., *Neuron,* 13, pp. 757-67 (1994)) by adding approximately 5000 cerebellar neurons to the CHO monolayers. Culture medium was SATO containing 2% FCS. After periods of time as indicated, the co-cultures were fixed for 30 minutes (min) with 4% paraformaldehyde and permeabilized with ice-cold methanol for 2 min. The cells were then blocked for 30 min with DMEM containing 10% FCS and incubated for 2 h with a rabbit polyclonal antibody against the neuronal marker GAP43 (1:4000). Cells were washed three times with PBS-BSA (2%) and then incubated for 30 min at room temperature with a biotinylated donkey anti-rabbit Ig (1:300, Amersham), washed three times, and incubated with streptavidin-conjugated Texas Red (1:300, Amersham) for 30 min. After three more washes, the slides were mounted in Permfluor (Baxter) and viewed with a Zeiss fluorescent microscope. The length of the longest neurite for each GAP43-positive neuron was determined using the Biological Detection System image analysis program (Pittsburgh).

Other available mammalian cell lines (e.g., COS cells) may alternatively be used with vectors having appropriate selectable markers, to express MAG, MAG derivatives (or other NgR ligands or the NgR receptor). Likewise, other neuron-specific antibodies such as anti-neurofilament monoclonal antibodies, which are commercially available (e.g., Boehringer Mannheim, Sigma Immunochemicals), may be used starting at dilutions recommended by the manufacturer. The appropriate species-specific, biotinylated anti-Ig secondary antibody is then selected according to the species in which the primary anti-neural antibody was generated. In addition, various vital dyes (e.g., Molecular Probes, Oregon) which stain neurites may be used in this assay in place of a fluorescent neural-specific antibody.

EXAMPLE 3

Binding of Wild-type and Mutant

MAG-Fc Chimeras to Neurons

Expression plasmids encoding various forms of soluble MAG-Fc fusion proteins (such as those referred to herein as MAG(L346D)-Fc), MAG(A404D)-Fc, MAG(E410K)-Fc, MAG(L431D)-Fc, MAG(K435E)-Fc, MAG(E445K)-Fc, MAG(R485D)-Fc, MAG(R491E)-Fc), and a control Fc-chimeric protein (MUC 18-Fc) were constructed using standard molecular biological procedures, as described below. For general discussions and protocols for making soluble recombinant adhesion molecules, see D. L. Simmons, "Cloning cell surface molecules by transient expression in mammalian cells," in *Cellular Interactions in Development—A Practical Approach,* pp. 118-125, IRL Press, Oxford (Ed. D. A. Hartley) (1993); *Development* (Supp.), pp. 193-203 (1993); and P. R. Crocker and S. Kelm, "Methods for studying the cellular binding properties of lectin-like receptors," in *Handbook of Experimental Immunology,* pp. 1-30 (1995), which are incorporated herein by reference.

The following point mutations were constructed in the background of a murine MAG-Fc chimeric fusion protein:

| Mutation Site (amino acid) | Mutation Site (nucleotides) | MAG Ig domain |
|---|---|---|
| L346D | CTG/GAC 1186-1188 | 4 |
| E378K | GAA/AAA 1282-1284 | 4 |
| W391D | TGG/GAC 1321-1323 | 4 |
| E395K | GAG/AAG 1333-1335 | 4/5 |
| A404D | GCC/GAC 1360-1362 | 4/5 |
| E410K | GAG/AAG 1378-1380 | 4/5 |
| Q429D | CAG/GAC 1435-1437 | 4/5 |
| L431D | CTA/GAC 1441-1443 | 5 |
| K435E | AAA/GAA 1453-1455 | 5 |
| E445K | GAG/AAG 1483-1485 | 5 |
| R485D | CGC/GAC 1603-1605 | 5 |
| R491E | AGG/AGG 1621-1623 | 5/TM |

Cloning of Mutant MAG-Fc Constructs:

DNA primers about 35-40 nucleotides in length were designed having at least about fifteen nucleotides of wild-type murine MAG sequences flanking each of the above triplet nucleotide mutations. Primers were synthesized by Invitrogen (Carlsbad, Calif.). Purified primers were then used to introduce the corresponding mutation into a wild-type murine MAG-Fc construct on a plasmid by polymerase chain reaction (PCR) following the protocol given by QuikChange Site-Directed Mutagenesis Kit (STRATAGENE #200518). The template plasmid used was one that carries an insert of murine MAG(d1-5)-Fc cDNA (see, e.g., U.S. Pat. No. 5,932, 542). (*E. coli* cell samples transformed with plasmids that express the MAG(d1-5)-Fc, MAG(d1-3)-Fc and MUC18-Fc chimeric proteins as described in Kelm et al., *Curr. Biol.* 4:965-972 (1994) were deposited on Jun. 27, 1996 with the American Type Culture Collection (ATCC) (Rockville, Md.) according to the provisions of the Budapest Treaty, and were assigned the ATCC accession numbers designated as shown:

|   | CELL LINE | Accession No. |
|---|---|---|
| a) | MAG[1-3]-Fc | ATCC 98089 |
| b) | MAG[1-5]-Fc | ATCC 98090 |
| c) | MUC18-Fc | ATCC 98088. |

After PCR reaction, products were digested with DpnI restriction enzyme (QuikChange Site-Directed Mutagenesis Kit; Stratagene #200518) according to manufacturers' instructions to deplete the template DNA before transformation into MC1061/P3 supercompetent cells (Invitrogen, Carlsbad, Calif.; #C663-03).

Production of Mutant MAG-Fc Proteins:

Plasmid DNA from transformed cell colonies was isolated and analyzed by endonuclease digestion and DNA sequencing to verify correct cloning of each of the above MAG mutations into the MAG-FC background. DNA was isolated from verified clones and used to transfect CHO cells. The wild-type MAG-Fc chimeric construct, upon translation, expresses a fused chimeric protein with the MAG extracellular domain (ECD) N-terminal to the hinge-constant 2-constant 3 region of IgG Fc. A CHO cell line comprising each such MAG mutant-Fc plasmid was established and grown in liquid culture. Cell supernatants were harvested and various MAG-Fc proteins were isolated from the supernatants by affinity chromatography using Protein A Sepharose CL-4B (Pharmacia; bead form: spherical, diameter 45-165 um, swollen form) according to the instructions of the manufacturer (see also Maniatis P18.12-18.13). Some Fc-proteins have been found to be unstable during the extended culture periods required for protein accumulation. In these cases it is important to monitor the production of Fe-proteins on a daily basis. If necessary, the Fc-protein was extracted with Protein A Sepharose and the medium recycled.

In addition, Fc-protein was dialyzed prior to concentration as many Fc-proteins exhibit reduced solubility in the Tris-neutralized buffer used in elution. The dialyzed proteins were concentrated to about 1-2 mg/ml using Centricon-30 microcentrators, sterilized by filtering with sterile Ultrafree-MC filter units (Cat. No. UFC30 OGV 25 0.2 um filter, Millipore). For all but short term culture use, concentrated fusion proteins were then sterilized by transferring the concentrated protein, about 500 ul, into a sterile Ultrafree-MC filter unit (Cat. No. UFC30 OGV 25 0.2 μm filter, Millipore), microcentriftiging at 4° C. at medium speed for 2 min. It is often desirable to concentrate further the purified Fc fusion protein (ultrafiltration) to avoid protein degradation at neutral pH. MAG-FC and MUC18-Fc are relatively stable in neutralized, high salt elution buffer. The apparent molecular weight and appearance of each fusion protein is checked by denaturing SDS-PAGE, and the protein concentration measured. Fusion proteins are aliquoted under sterile conditions and stored at −70° C.

Binding of Fc-Chimeras to Neurons

Plasmids encoding the various mutant MAG-Fc chimeras or the control chimeric fusion (MUC 18-Fc) described above were transfected into COS cells and the Fc-chimeric proteins were purified from the media as described in Kelm et al., Current Biol., 4, pp. 965-72 (1994) and P. R. Crocker and S. Kelm, "Methods for studying the cellular binding properties of lectin-like receptors," in Handbook of Experimental Immunology, pp. 1-30 (1995).

Neuron binding assays were performed essentially as described in DeBallard et al., Mol. Cell. Neuroscience, 7, pp. 89-101 (1996), which is incorporated herein by reference. Fc-chimeric proteins were adsorbed for 3 hours (h) at 37° C. to wells of microtiter plates that had been coated for 2 h at 37° C. with anti-human IgG at 15 μg/ml in 0.1M bicarbonate buffer, pH 9.6. Prior to the binding assay, cerebellar neurons, isolated as described in Example 1, were vitally labeled with the fluorescent dye calcein AM (Molecular Probes) by incubating $2\times10^6$ neurons in 5 ml of 101M calcein AM in PBS for 15 minutes (min) at 37° C. before being washed and resuspended in PBS. One hundred μl of a suspension of vitally labeled neurons, containing $1-2\times10^5$ cells was added to each well and allowed to incubate for 1 h at room temperature. The plates were washed three times with PBS applied to each well under gravity and the fluorescence was measured in a FluorImager (Molecular Dynamics). Results from these experiments are illustrated in FIG. 2. MAG-Fc shows significant binding to neurons as compared to binding by a control chimera. All of the mutant MAG-Fc chimeras could bind to cerebellar neurons as well as the wild-type MAG-FC protein.

EXAMPLE 4

Neurite Outgrowth Assays on a Growth Permissive Substrate in the Presence or Absence of Mutant MAG-Fc Chimera Growth Permissive Substrate Comprising an L1-Fc Chimera The L1 glycoprotein is a cell adhesion molecule (CAM) expressed on the surface of a wide variety of mammalian neuronal cell types which stimulates neurite outgrowth. Soluble L1-Fc chimera may be constructed using procedures known to those of skill in the art (such as those cited in Example 2; Doherty et al., Neuron, pp. 57-66 (1995), incorporated herein by reference). Soluble L1-Fc chimera, when presented to neurons, are as effective at promoting neurite outgrowth as the normal cell surface-associated L1 (Doherty et al., supra, and references cited therein which are incorporated herein by reference). As described in Doherty et al., L1-Fc chimera can stably associate with the surface of fibroblast 3T3 cells or polylysine/collagen or polylysine/fibronectin-coated substrates.

Individual wells of an eight-chamber tissue culture plastic slide (Lab-Tek, Nuc. Inc.) were incubated with 0.3 ml of 16.6 μg/ml poly-1-lysine in sterile water for at least one hour under sterile conditions. Each well was washed twice with 400 μl of a 0.1M sodium bicarbonate solution, pH 9.6, and then received 0.3 ml of 0.1M sodium bicarbonate solution, pH 9.6, containing 15 μg/ml goat anti-human IgG (Fc-specific) monoclonal antibody (Sigma). The wells were incubated for 2 hours (h) at 37° C., and washed three times with 0.4 ml of ice-cold DMEM. Each well then received 0.3 ml of DMEM containing 40 μg/ml of L1-Fc and was incubated for 2-4 h at 37° C. The wells were washed twice DMEM.

Neurite Outgrowth on L1-Fc Substrate:

A Soluble MAG-Fc Binding Assay

Cerebellar neurons (post-natal days 2-7) were dissociated by trypsinization as described in Example 1, except that the dissociated neurons were resuspended in 5 ml of SATO medium containing 2% dialyzed FBS. To an individual well coated with a monolayer of L1-Fc as described above, $5.0\times10^4$ cerebellar neurons were added, followed by addition of one of the mutant MAG-Fc or MUC 18-Fc chimeric soluble protein described above at a concentration of 25 µg/ml. Neurons were cultured for 18 hours at 37° C., and then fixed and stained for GAP43 essentially as described in Example 2. Neurite length was measured for 180-200 neurons.

FIG. 3 depicts the results of these experiments. Wild-type MAG-Fc inhibited neurite outgrowth by about 60% while a control chimera had no effect. MAG(L346D)-Fc, MAG(A404D)-Fc, and MAG(E410K)-Fc inhibited neurite outgrowth as effectively as MAG-Fc. In contrast, none of the MAG-Fc chimeras mutated in Ig domain 5, i.e., MAG(L431D)-Fc, MAG(K435E)-Fc, MAG(E445K)-Fc. MAG(R485D)-Fc, and MAG(R491E)-Fc, inhibited neurite outgrowth as compared to the control chimera.

EXAMPLE 5

Neurite Outgrowth Assays on a Growth Permissive Substrate in the Presence or Absence of MAG Peptides Peptides corresponding to amino acid residues 343-372 of MAG (MAG(343-371)), amino acid residues 363-397 (MAG(363-397)), amino acid residues 394-428 (MAG(394-428)), amino acid residues 422-451 (MAG(422-451)), amino acid residues 442-471 (MAG(442-471)), and amino acid residues 461-498 (MAG(461-498)) were synthesized. Peptides were obtained from SynPep Corp. (Dublin, Calif.). MAG(343-371), MAG(363-397) and MAG(394-428) correspond to amino acid residues from the Ig4 domain of MAG. MAG(422-451), MAG(442-471) and MAG(461-498) corresponds to amino acid residues from the Ig5 domain of MAG. Isolated p2 cerebellar neurons (Example 1) were plated onto monolayers of CHO expressing MAG cells in the presence of the different peptides at 15 µM, as indicated in FIG. 4, and cultured overnight before being fixed for neurite outgrowth assays, as described in Example 2. Results are shown in FIG. 4 (and are represented as number of neurons with processes longer than 2-times the cell diameter). Peptides corresponding to MAG amino acid residues 433-457 (M433) and 462-486 (M462) and a peptide derived from sialoadhesin Ig-like domain 5 (Sn447-476 SHGGLTLASNSGENDFNPRFRIS-SAPNSLR) (SEQ ID NO: 42) were similarly synthesized and tested for inhibitory activity using isolated p2 cerebellar neurons (Example 1), plated onto monolayers of CHO expressing MAG cells in the presence of the different peptides at 20 µM, as indicated in FIG. 5, and cultured for 18 hours before being fixed for neurite outgrowth assays, as described in Example 2. Results are shown in FIG. 5 (and are represented as average neurite length for 180-200 neurons).

EXAMPLE 6

Neurite Outgrowth Assays on a Growth Permissive Substrate in the Presence or Absence of MAG, Nogo and OMgp Peptides Peptides corresponding to MAG amino acid residues 437-441 (M437), 446-455 (M446), 450-455 (M450), 466-471 (M466); and 472-477 (M472) are constructed and tested in neurite outgrowth assays as described in Example 5. (See peptides in FIG. 18). All MAG peptides reduce the ability of the wild-type MAG-expressing-cells to inhibit neurite outgrowth.

Peptides corresponding to Nogo-66 amino acid residues 13-17 (N13), 22-31(N22-1), 22-34 (N22-2), 26-31 (N26-1); 26-34 (N26-2); 9-33 (N-9-1); 9-34 (N-9-2); 38-62 (N38); 42-47 (N42); and 48-53 (N48) are also constructed and tested in neurite outgrowth assays as described in Example 5. All peptides reduce the ability of the wild-type MAG-expressing cells to inhibit neurite outgrowth.

Peptides corresponding to OMgp amino acid residues 206-210 (O206), 215-224 (O215), 219-224 (O219), 202-226 (O202); 231-255 (O231), 235-240 (O235) 241-246 (O241) are constructed and tested in neurite outgrowth assays as described in Example 5. All peptides reduce the ability of the wild-type MAG-expressing cells to inhibit neurite outgrowth.

EXAMPLE 7

Experimental Modulation of Neuronal Growth and Regeneration in Vivo

Delivery to animals, including humans, of molecules (polypeptides or nucleic acids) and compositions comprising the molecules of the invention (i.e., delivery of MAG derivatives, NgR binding inhibitors and NgR activators) are effective in regulating (e.g., controlling or relieving inhibition of) regeneration and repair in the nervous system. The delivery of such molecules to neurons in vivo may be achieved in a variety of ways that will be apparent to those of skill in the art, e.g., by standard techniques for delivery of molecules to the nervous system as well as by gene transfer techniques.

Methods for viral or non-viral-mediated gene transfer into neurons and glial cells of the nervous system are known in the art. (See, e.g., Basic Science and Gene Therapy (2000) Cid-Arregui, A. and A. Garcia-Carranca, editors. Natick, Mass.: Eaton Publishing. Polynucleotides encoding secreted forms of the molecules of the invention (i.e., MAG derivatives, NgR binding inhibitors and NgR activators) may be transferred into a desired target cell and expression products will appear in the fluids which bathe the cells of the nervous system, e.g., the CSF, which may then be transported into cells in communication with those fluids. Inducible and other regulated expression of polynucleotides of the invention are contemplated to be within the scope of this invention using known and available transcription control sequences and expression systems for regulating heterologous genes.

Mammalian cells (e.g., CHO or COS cells) transfected with an expression plasmid of the invention, e.g., one that encodes an expressed and secreted form of a MAG derivative, NgR binding inhibitor or NgR activator, are cultured and the cultures assayed for rate of secretion. Approximately $2 \times 10^6$ cells—which secrete about 1 mg of a MAG derivative—Fc fusion protein over a 5-day period—are surgically implanted into the cerebrospinal fluid surrounding the spinal cord of a diseased or injured subject in the vicinity of nerve damage in need of repair. Optionally, repeated administrations are performed. The cells secrete the MAG derivative which is capable of inhibiting endogenous MAG activity in the myelin of the implant site, and neural regeneration is stimulated.

Molecules of the invention may be administered directly or indirectly to the nervous system using techniques for in vivo protein and peptide delivery known to those of skill in the art (see supra).

We claim:

1. An isolated polypeptide comprising a neuronal binding region consisting of an Ig-like domain 1 (Igd1) of a protein, wherein said protein has at least 75% sequence identity to SEQ ID NO: 2, 4 or 6 and said neuronal binding region is capable of binding said polypeptide to neuronal surfaces;
    the polypeptide further comprises at least one of MAG Ig-like domain 5 (Igd5) amino acid residues 432 to 488 and lacks MAG Igd5 amino acid residues 450 to 490 or 450 to 453 of SEQ ID NO: 2, 4, or 6; and
    whereby the ability of the polypeptide to regulate neurite outgrowth as compared to endogenous or soluble MAG is reduced or eliminated.

2. The polypeptide according to claim 1, wherein said polypeptide comprises at least one extracellular domain of MAG other than Igd5.

3. The polypeptide according to claim 1, wherein said polypeptide comprises at least one Ig-like domain from a heterologous protein.

4. The polypeptide according to claim 1, wherein said polypeptide comprises an Ig Fc domain.

5. An isolated polypeptide comprising a MAG Ig5 amino acid sequence and optionally further comprising a genetic, enzymatic, chemical or immunological marker; wherein said MAG Ig5 sequence consists of amino acid residues 433-457, 422-451, 442-471, 446-455, 450-455, 466-471, or 472-477 of SEQ ID NO:2, 4, or 6; whereby the ability of the polypeptide to regulate neurite outgrowth as compared to endogenous or soluble MAG is reduced or eliminated without eliminating binding of the polypeptide to neuronal surface.

6. The polypeptide according to claim 5, optionally fused to said genetic, enzymatic, chemical or immunological marker, wherein said MAG Ig5 sequence consists of residues 433-457, 422-451, or 442-471 of SEQ ID NO: 2, 4, or 6.

7. The polypeptide according to claim 1 or 5, which has a decreased ability to inhibit neurite outgrowth as compared to endogenous or soluble MAG.

8. The polypeptide according to claim 1 or 5, wherein the polypeptide is derived from a rat, murine or human MAG.

9. The polypeptide according to claim 1 or 5, which has a reduced ability to activate signaling of Nogo receptor (NgR) as compared to endogenous or soluble MAG.

10. The polypeptide according to claim 1 or 5, wherein said polypeptide can decrease inhibition of neural regeneration by myelin.

11. The polypeptide according to claim 1 or 5, wherein said polypeptide can decrease inhibition of axonal outgrowth by a neuron.

12. The polypeptide according to claim 1 or 5, wherein said polypeptide can regulate neural growth or regeneration.

13. The polypeptide according to claim 12, wherein the neural growth or regeneration is promoted.

14. A composition comprising the polypeptide according to claim 1 or 5.

15. The composition according to claim 14, further comprising a pharmaceutically acceptable carrier.

16. An isolated polypeptide consisting of amino acid residues 437-441 of SEQ ID NO: 2, 4 or 6.

17. An isolated polypeptide consisting of amino acid residues 462-486 of SEQ ID NO: 2, 4 or 6.

18. An isolated polypeptide that differs from wild-type MAG in that the polypeptide lacks residues 466-478, residues being numbered any of SEQ ID NO:2, 4, or 6; wherein the ability of the polypeptide to regulate neurite outgrowth as compared to endogenous or soluble MAG is reduced or eliminated without eliminating binding of the polypeptide to neuronal surface.

* * * * *

SEQUENCE LISTING

<160> NUMBER OF SEQ ID NOS: 43

<210> SEQ ID NO 1
<211> LENGTH: 2475
<212> TYPE: DNA
<213> ORGANISM: Rattus norvegicus

<400> SEQUENCE: 1

| | | | | | |
|---|---|---|---|---|---|
| cagaagccag | accatccaac | cttctgtatc | agtgctcctc | gtcgcctcac | tgtacttcac | 60 |
| ggaagagact | tggttgactg | gccacttgga | gcggaatcag | gagacattcc | caactcaggg | 120 |
| agactgaggt | gagggcccta | gctcgcccac | ttgctggaca | agatgatatt | ccttaccacc | 180 |
| ctgcctctgt | tttggataat | gatttcagct | tctcgagggg | ggcactgggg | tgcctggatg | 240 |
| ccctcgtcca | tctcagcctt | cgagggcacg | tgtgtctcca | tccctgccg | tttcgacttc | 300 |
| ccggatgagc | tcagaccggc | tgtggtacat | ggcgtctggt | atttcaacag | tccctacccc | 360 |
| aagaactacc | cgccagtggt | cttcaagtcc | cgcacacaag | tggtccacga | gagcttccag | 420 |
| ggccgtagcc | gcctgttggg | agacctgggc | ctacgaaact | gcaccctgct | tctcagcacg | 480 |
| ctgagccctg | agctgggagg | gaaatactat | ttccgaggtg | acctgggcgg | ctacaaccag | 540 |
| tacaccttct | cggagcacag | cgtcctggac | atcatcaaca | cccccaacat | cgtggtgccc | 600 |
| ccagaagtgg | tggcaggaac | ggaagtagag | gtcagctgca | tggtgccgga | caactgccca | 660 |
| gagctgcgcc | ctgagctgag | ctggctgggc | acgaggggc | taggggagcc | cactgttctg | 720 |
| ggtcggctgc | gggaggatga | aggcacctgg | gtgcaggtgt | cactgctaca | cttcgtgcct | 780 |
| actagagagg | ccaacggcca | ccgtctgggc | tgtcaggctg | ccttccccaa | caccaccttg | 840 |
| cagttcgagg | gttacgccag | tctggacgtc | aagtaccccc | cggtgattgt | ggagatgaat | 900 |
| tcctctgtgg | aggccattga | gggctcccat | gtcagcctgc | tctgtggggc | tgacagcaac | 960 |
| ccgccaccgc | tgctgacttg | gatgcgggat | gggatggtgt | tgagggaggc | agttgctgag | 1020 |
| agcctgtacc | tggatctgga | ggaggtgacc | ccagcagagg | acggcatcta | tgcttgcctg | 1080 |
| gcagagaatg | cctatggcca | ggacaaccgc | acggtggagc | tgagcgtcat | gtatgcacct | 1140 |
| tggaagccca | cagtgaatgg | gacggtggtg | gcggtagagg | gggagacagt | ctccatcctg | 1200 |
| tgttccacac | agagcaaccc | ggaccctatt | ctcaccatct | tcaaggagaa | gcagatcctg | 1260 |
| gccacggtca | tctatgagag | tcagctgcag | ctggaactcc | ctgcagtgac | gcccgaggac | 1320 |
| gatggggagt | actggtgtgt | agctgagaac | cagtatggcc | agagagccac | cgccttcaac | 1380 |
| ctgtctgtgg | agtttgctcc | cataatcctt | ctggaatcgc | actgtgcagc | ggccagagac | 1440 |
| accgtgcagt | gcctgtgtgt | ggtaaaatcc | aacccggaac | cctccgtggc | ctttgagctg | 1500 |
| ccttcccgca | acgtgactgt | gaacgagaca | gagagggagt | ttgtgtactc | agagcgcagc | 1560 |
| ggcctcctgc | tcaccagcat | cctcacgctc | cggggtcagg | cccaagcccc | accccgcgtc | 1620 |
| atttgtacct | ccaggaacct | ctacggcacc | cagagcctcg | agctgccttt | ccagggagca | 1680 |
| caccgactga | tgtgggccaa | aatcggccct | gtgggtgctg | tggtcgcctt | tgccatcctg | 1740 |
| attgccattg | tctgctacat | cacccagaca | agaagaaaaa | agaacgtcac | agagagcccc | 1800 |
| agcttctcag | cggagacaa | ccctcatgtc | ctgtacagcc | ccgaattccg | aatctctgga | 1860 |
| gcacctgata | agtatgagag | tgagaagcgc | ctggggtccg | agaggaggct | gctgggcctt | 1920 |
| agggggaac | cccagaact | ggacctcagt | tattcccact | cagacctggg | gaaacgaccc | 1980 |
| accaaggaca | gctacaccct | gacagaggag | ctggctgagt | acgcagaaat | ccgagtcaag | 2040 |

-continued

```
tgaggaagct gggggctggc cctgtggctc accccccatc aggaccctcg cttggccccc    2100 actgccgtg ggctcccttt ctcttgagag tggtaggggt gggggcggga aggggcgggg    2160
caggaaacag tgaggtctta ggggcccggc ctcccctcct tcccggctgc tcctctctgc    2220
caacatcctg cacctatgtt acagctccct ctcccctcct tttaacctca gctgttgaga    2280
ggggtgctct gtctgtccat gttatttatt gttatcctgg tctcctgtcc ccttacccgg    2340
ccccaggacc tgtacaaaag ggacatgaaa taaatgtcct aatgacaagt gccagtctag    2400
acccatcctt tggaggaaag ggcatatta gtaatacttt tctcgttgct gtaacaaaat    2460
actggacaaa aacac                                                     2475
```

<210> SEQ ID NO 2
<211> LENGTH: 626
<212> TYPE: PRT
<213> ORGANISM: Rattus norvegicus

<400> SEQUENCE: 2

```
Met Ile Phe Leu Thr Thr Leu Pro Leu Phe Trp Ile Met Ile Ser Ala
  1               5                  10                  15

Ser Arg Gly Gly His Trp Gly Ala Trp Met Pro Ser Ser Ile Ser Ala
                 20                  25                  30

Phe Glu Gly Thr Cys Val Ser Ile Pro Cys Arg Phe Asp Phe Pro Asp
             35                  40                  45

Glu Leu Arg Pro Ala Val Val His Gly Val Trp Tyr Phe Asn Ser Pro
         50                  55                  60

Tyr Pro Lys Asn Tyr Pro Pro Val Val Phe Lys Ser Arg Thr Gln Val
 65                  70                  75                  80

Val His Glu Ser Phe Gln Gly Arg Ser Arg Leu Leu Gly Asp Leu Gly
                 85                  90                  95

Leu Arg Asn Cys Thr Leu Leu Leu Ser Thr Leu Ser Pro Glu Leu Gly
            100                 105                 110

Gly Lys Tyr Tyr Phe Arg Gly Asp Leu Gly Gly Tyr Asn Gln Tyr Thr
        115                 120                 125

Phe Ser Glu His Ser Val Leu Asp Ile Ile Asn Thr Pro Asn Ile Val
    130                 135                 140

Val Pro Pro Glu Val Val Ala Gly Thr Glu Val Glu Val Ser Cys Met
145                 150                 155                 160

Val Pro Asp Asn Cys Pro Glu Leu Arg Pro Glu Leu Ser Trp Leu Gly
                165                 170                 175

His Glu Gly Leu Gly Glu Pro Thr Val Leu Gly Arg Leu Arg Glu Asp
            180                 185                 190

Glu Gly Thr Trp Val Gln Val Ser Leu Leu His Phe Val Pro Thr Arg
        195                 200                 205

Glu Ala Asn Gly His Arg Leu Gly Cys Gln Ala Ala Phe Pro Asn Thr
    210                 215                 220

Thr Leu Gln Phe Glu Gly Tyr Ala Ser Leu Asp Val Lys Tyr Pro Pro
225                 230                 235                 240

Val Ile Val Glu Met Asn Ser Ser Val Glu Ala Ile Glu Gly Ser His
                245                 250                 255

Val Ser Leu Leu Cys Gly Ala Asp Ser Asn Pro Pro Pro Leu Leu Thr
            260                 265                 270

Trp Met Arg Asp Gly Met Val Leu Arg Glu Ala Val Ala Glu Ser Leu
        275                 280                 285
```

```
Tyr Leu Asp Leu Glu Glu Val Thr Pro Ala Glu Asp Gly Ile Tyr Ala
    290                 295                 300
Cys Leu Ala Glu Asn Ala Tyr Gly Gln Asp Asn Arg Thr Val Glu Leu
305                 310                 315                 320
Ser Val Met Tyr Ala Pro Trp Lys Pro Thr Val Asn Gly Thr Val Val
                325                 330                 335
Ala Val Glu Gly Glu Thr Val Ser Ile Leu Cys Ser Thr Gln Ser Asn
            340                 345                 350
Pro Asp Pro Ile Leu Thr Ile Phe Lys Glu Lys Gln Ile Leu Ala Thr
        355                 360                 365
Val Ile Tyr Glu Ser Gln Leu Gln Leu Glu Leu Pro Ala Val Thr Pro
    370                 375                 380
Glu Asp Asp Gly Glu Tyr Trp Cys Val Ala Glu Asn Gln Tyr Gly Gln
385                 390                 395                 400
Arg Ala Thr Ala Phe Asn Leu Ser Val Glu Phe Ala Pro Ile Ile Leu
                405                 410                 415
Leu Glu Ser His Cys Ala Ala Ala Arg Asp Thr Val Gln Cys Leu Cys
            420                 425                 430
Val Val Lys Ser Asn Pro Glu Pro Ser Val Ala Phe Glu Leu Pro Ser
        435                 440                 445
Arg Asn Val Thr Val Asn Glu Thr Glu Arg Glu Phe Val Tyr Ser Glu
    450                 455                 460
Arg Ser Gly Leu Leu Leu Thr Ser Ile Leu Thr Leu Arg Gly Gln Ala
465                 470                 475                 480
Gln Ala Pro Pro Arg Val Ile Cys Thr Ser Arg Asn Leu Tyr Gly Thr
                485                 490                 495
Gln Ser Leu Glu Leu Pro Phe Gln Gly Ala His Arg Leu Met Trp Ala
            500                 505                 510
Lys Ile Gly Pro Val Gly Ala Val Ala Phe Ala Ile Leu Ile Ala
        515                 520                 525
Ile Val Cys Tyr Ile Thr Gln Thr Arg Arg Lys Lys Asn Val Thr Glu
    530                 535                 540
Ser Pro Ser Phe Ser Ala Gly Asp Asn Pro His Val Leu Tyr Ser Pro
545                 550                 555                 560
Glu Phe Arg Ile Ser Gly Ala Pro Asp Lys Tyr Glu Ser Glu Lys Arg
                565                 570                 575
Leu Gly Ser Glu Arg Arg Leu Leu Gly Leu Arg Gly Glu Pro Pro Glu
            580                 585                 590
Leu Asp Leu Ser Tyr Ser His Ser Asp Leu Gly Lys Arg Pro Thr Lys
        595                 600                 605
Asp Ser Tyr Thr Leu Thr Glu Glu Leu Ala Glu Tyr Ala Glu Ile Arg
    610                 615                 620
Val Lys
625

<210> SEQ ID NO 3
<211> LENGTH: 2429
<212> TYPE: DNA
<213> ORGANISM: Mus sp.

<400> SEQUENCE: 3
gtcagatcgt ccaaccttct gtgttagcgt tcctcagctc ctcattgcag ttccctgaag      60
agacttggtt gaaaggccac ttcaagtgga atcaggagac atccccaact cagggagact     120
aagccctagc tcaatcactt gctaaacaag atgatattcc tcgccaccct gccgctgttt     180
```

-continued

```
tggataatga tttcagcttc tcgaggggc cactggggtg cctggatgcc ctcgaccatc        240
tcagccttcg agggcacgtg tgtctccatt ccctgccgtt tcgacttccc cgatgagctc       300
agaccggctg tggtacatgg cgtctggtat ttcaatagtc cctaccccaa gaactaccca       360
ccggtggtct tcaagtcccg cacacaagtg gtccatgaga gtttccaggg ccgcagccgc       420
ctattgggag acctgggcct acgaaactgt accctgcttc tcagcacact gagccccgag       480
ctgggaggca atactatttt ccgaggcgac ctgggtggct acaaccagta caccttctcg       540
gagcacagcg tcctggacat cgtcaacacc cccaacattg tggttccccc ggaagtggtg       600
gcaggaacgg aagtggaggt cagttgtatg gtgccggaca actgcccaga gctgcggcca       660
gagctgagct ggctgggcca cgaggggctg ggagagccca ctgtgctggg tcggctgcgt       720
gaggatgaag gcacctgggt gcaggtgtcg ctgctacact tcgtgcctac tagagaggcc       780
aacggccacc gtctgggctg tcaggctgcc ttccccaaca ccaccttgca gttcgagggt       840
tacgccagtt tggacgtcaa gtaccccca gtgattgtgg agatgaattc ctctgtggag        900
gccattgagg gctcccatgt cagcctgctc tgtggggctg acagcaaccc gccgccgctg       960
ctgacttgga tgcgggatgg gatggtgttg agggaggcag ttgccaagag cctctacctg      1020
gatctggagg aggtgacccc aggagaggac ggcgtctatg cttgcctagc agagaacgcc      1080
tatggccagg acaaccgcac ggtggagctg agtgtcatgt atgcaccttg gaagcccaca      1140
gtgaatggga cggtggtggc cgtagagggg gagactgtct ctatcctgtg ttccacacag      1200
agcaacccgg accccatcct taccatcttc aaggagaagc agatcctagc cacggtcatc      1260
tatgagagtc agctgcagct ggaactcccc gcagtgaccc ccgaggatga tggggaatac      1320
tggtgtgtgg ctgagaacca gtatggccag agagccactg ccttcaacct gtctgtggag      1380
tttgccccca taatccttct ggagtcacac tgtgcagcgg ccagagacac cgtgcagtgt      1440
ctatgtgtgg taaaatccaa cccggaaccc tctgtggcct tgagctgcc ttcccgcaac       1500
gtgactgtga atgagacgga gagggagttt gtgtactccg agcgcagtgg cctcctgctc      1560
accagcatcc tcacgatccg gggtcaggcc caagcccac cccgcgtcat ttgtacctcc       1620
aggaacctct atggcaccca gagcctcgag ctgccttttcc agggagcaca ccgactgatg      1680
tgggccaaaa tcggtcctgt gggtgctgtg gtcgcctttg ccatcctgat tgccattgtg      1740
tgctacatca cccagacgag aagaaaaaag aatgtcacgg agagctccag cttctcaggg      1800
ggagacaacc ctcatgtcct gtacagcccc gaattcagaa tctctggggc acctgataag      1860
tatgagtcca gagaggtctc tacccgggat tgtcactgag agccccagga gagtgagaag      1920
cagcgcctgg gatctgagag gaggctgctg ggccttcggg gggaatcccc agaactggac      1980
ctcagttatt cccactcaga cctgggaaaa cgacccacca aggacagcta caccctgaca      2040
gaggagctgc tgagtatgc agaaatccga gtcaagtgag gacgctgggg gctggccctg       2100
tggctcaccc cccatcaaga ccctcgctgg gccccactg gctgtgggct ccctttctct       2160
tgagagtagt aggggtgagg gcgggaaggg gcaggacagg aaacagtgag gtcctggggg      2220
cctggcctcc cctccttccc agctgttcct ccttgccaac attccttgcc tacattagag      2280
ctccctctc ccttccttttt aacctcagct gttgagaggg gtgctctgtc tgtccatgtt       2340
atttattgct atccctttcc tggtctcctg tcccttacct ggccccagga cctgtacaaa      2400
aagggacatg aaataaatgt cctaatgac                                        2429
```

<210> SEQ ID NO 4

<211> LENGTH: 582
<212> TYPE: PRT
<213> ORGANISM: Mus sp.

<400> SEQUENCE: 4

```
Met Ile Phe Leu Ala Thr Leu Pro Leu Phe Trp Ile Met Ile Ser Ala
 1               5                  10                  15

Ser Arg Gly Gly His Trp Gly Ala Trp Met Pro Ser Thr Ile Ser Ala
            20                  25                  30

Phe Glu Gly Thr Cys Val Ser Ile Pro Cys Arg Phe Asp Phe Pro Asp
        35                  40                  45

Glu Leu Arg Pro Ala Val Val His Gly Val Trp Tyr Phe Asn Ser Pro
 50                  55                  60

Tyr Pro Lys Asn Tyr Pro Pro Val Val Phe Lys Ser Arg Thr Gln Val
 65                  70                  75                  80

Val His Glu Ser Phe Gln Gly Arg Ser Arg Leu Leu Gly Asp Leu Gly
                85                  90                  95

Leu Arg Asn Cys Thr Leu Leu Leu Ser Thr Leu Ser Pro Glu Leu Gly
            100                 105                 110

Gly Lys Tyr Tyr Phe Arg Gly Asp Leu Gly Gly Tyr Asn Gln Tyr Thr
        115                 120                 125

Phe Ser Glu His Ser Val Leu Asp Ile Val Asn Thr Pro Asn Ile Val
130                 135                 140

Val Pro Pro Glu Val Val Ala Gly Thr Glu Val Glu Val Ser Cys Met
145                 150                 155                 160

Val Pro Asp Asn Cys Pro Glu Leu Arg Pro Glu Leu Ser Trp Leu Gly
                165                 170                 175

His Glu Gly Leu Gly Glu Pro Thr Val Leu Gly Arg Leu Arg Glu Asp
            180                 185                 190

Glu Gly Thr Trp Val Gln Val Ser Leu Leu His Phe Val Pro Thr Arg
        195                 200                 205

Glu Ala Asn Gly His Arg Leu Gly Cys Gln Ala Ala Phe Pro Asn Thr
210                 215                 220

Thr Leu Gln Phe Glu Gly Tyr Ala Ser Leu Asp Val Lys Tyr Pro Pro
225                 230                 235                 240

Val Ile Val Glu Met Asn Ser Ser Val Glu Ala Ile Glu Gly Ser His
                245                 250                 255

Val Ser Leu Leu Cys Gly Ala Asp Ser Asn Pro Pro Leu Leu Thr
            260                 265                 270

Trp Met Arg Asp Gly Met Val Leu Arg Glu Ala Val Ala Lys Ser Leu
        275                 280                 285

Tyr Leu Asp Leu Glu Glu Val Thr Pro Gly Glu Asp Gly Val Tyr Ala
290                 295                 300

Cys Leu Ala Glu Asn Ala Tyr Gly Gln Asp Asn Arg Thr Val Glu Leu
305                 310                 315                 320

Ser Val Met Tyr Ala Pro Trp Lys Pro Thr Val Asn Gly Thr Val Val
                325                 330                 335

Ala Val Glu Gly Glu Thr Val Ser Ile Leu Cys Ser Thr Gln Ser Asn
            340                 345                 350

Pro Asp Pro Ile Leu Thr Ile Phe Lys Glu Lys Gln Ile Leu Ala Thr
        355                 360                 365

Val Ile Tyr Glu Ser Gln Leu Gln Leu Glu Leu Pro Ala Val Thr Pro
370                 375                 380

Glu Asp Asp Gly Glu Tyr Trp Cys Val Ala Glu Asn Gln Tyr Gly Gln
```

-continued

```
            385                 390                 395                 400
Arg Ala Thr Ala Phe Asn Leu Ser Val Glu Phe Ala Pro Ile Ile Leu
                405                 410                 415
Leu Glu Ser His Cys Ala Ala Ala Arg Asp Thr Val Gln Cys Leu Cys
            420                 425                 430
Val Val Lys Ser Asn Pro Glu Pro Ser Val Ala Phe Glu Leu Pro Ser
        435                 440                 445
Arg Asn Val Thr Val Asn Glu Thr Glu Arg Glu Phe Val Tyr Ser Glu
    450                 455                 460
Arg Ser Gly Leu Leu Leu Thr Ser Ile Leu Thr Ile Arg Gly Gln Ala
465                 470                 475                 480
Gln Ala Pro Pro Arg Val Ile Cys Thr Ser Arg Asn Leu Tyr Gly Thr
                485                 490                 495
Gln Ser Leu Glu Leu Pro Phe Gln Gly Ala His Arg Leu Met Trp Ala
            500                 505                 510
Lys Ile Gly Pro Val Gly Ala Val Val Ala Phe Ala Ile Leu Ile Ala
        515                 520                 525
Ile Val Cys Tyr Ile Thr Gln Thr Arg Arg Lys Lys Asn Val Thr Glu
    530                 535                 540
Ser Ser Ser Phe Ser Gly Gly Asp Asn Pro His Val Leu Tyr Ser Pro
545                 550                 555                 560
Glu Phe Arg Ile Ser Gly Ala Pro Asp Lys Tyr Glu Ser Arg Glu Val
                565                 570                 575
Ser Thr Arg Asp Cys His
            580

<210> SEQ ID NO 5
<211> LENGTH: 2380
<212> TYPE: DNA
<213> ORGANISM: Homo sapiens

<400> SEQUENCE: 5
ctagaccctg gaaggcaggg gactgcgagc tgggctggcg gagcagaggt gcagaagcaa      60
ctgagtccaa gttgtctggc ggcttcaggt ggacccagaa gacgtcccca actcagggag     120
attcagcgat cactcactcg ctgtacagaa tgatattcct cacggcactg cctctgttct     180
ggattatgat ttcagcctcc cgagggggtc actggggtgc ctggatgccc tcgtccatct     240
cggccttcga aggcacgtgc gtctccatcc cctgccgctt tgacttcccg gatgagctgc     300
ggcccgctgt ggtgcatggt gtctggtact tcaatagccc ctaccccaag aactacccc      360 cggtggtctt caagtcgcgc acccaagtag tccacgagag cttccagggc cgcagccgcc     420
tcctggggga cctgggcctg cgaaactgca ccctcctgct cagcaacgtc agccccgagc     480
tgggcgggaa gtactacttc cgtggggacc tgggcggcta caaccagtac accttctcag     540
agcacagcgt cctggatatc gtcaacaccc ccaacatcgt ggtgccccca gaggtggtgg     600
caggcacgga ggtggaggtc agctgcatgg tgccggacaa ctgcccagag ctgcgccctg     660
agctgagctg gctgggccac gaggggctgg ggagcccgc tgtgctgggc ggctgcgggg     720
aggacgaggg cacctgggtg caggtgtcac tgctgcactt cgtgcccacg agggaggcca     780
acggccacag gctgggctgc caggcctcct tccccaacac caccctgcag ttcgagggct     840
acgccagcat ggacgtcaag taccccccgg tgattgtgga gatgaactcc tcggtggagg     900
ccatcgaggc tcccacgtg agcctgctct gtggggctga cagcaacccc cgccgctgc      960 tgacctggat gcgggacggg acagtcctcc gggaggcggt ggccgagagc ctgctcctgg    1020
```

-continued

```
agctggagga ggtgaccccc gccgaagacg gcgtctatgc ctgcctggcc gagaatgcct     1080
atggccagga caaccgcacc gtggggctca gtgtcatgta tgcaccctgg aagccaacag     1140
tgaacgggac aatggtggcc gtagaggggg agacggtctc tatcttgtgc tccacacaga     1200
gcaacccgga ccctattctc accatcttca aggagaagca gatcctgtcc acggtcatct     1260
acgagagcga gctgcagctg agctgccgg ccgtgtcacc cgaggatgat ggagagtact      1320
ggtgtgtggc tgagaaccag tatggccaga gggccaccgc cttcaacctg tctgtggagt     1380 cgcccctgt gctcctcctg gagtcccact cgcgcggcagc ccgagacacg gtgcagtgcc    1440
tgtgcgtggt gaagtccaac ccggagccgt ccgtggcctt tgagctgcca tcgcgcaatg     1500
tgaccgtgaa cgagagcgag cgggagttcg tgtactcgga gcgcagcggc ctcgtgctca     1560
ccagcatcct cacgctgcgg ggcaggccc aggccccgcc ccgcgtcatc tgcaccgcga     1620
ggaacctcta tggcgccaag agcctggagc tgcccttcca gggagcccat cgactgatgt     1680
gggccaagat cgggcctgtg gcgccgtgg tcgccttgtgc catcctgatt gccatcgtct     1740
gctacattac ccagacacgc aggaaaaaga acgtgacaga gagccccagc ttctcggcag     1800
gggacaaccc tcccgtcctg ttcagcagcg acttccgcat ctctgggcca ccagagaagt     1860
acgagagcga gaggcgcctg ggatctgaga ggaggctgct gggccttcgg ggtgagcccc     1920
cagagctgga cctgagctat tctcactcgg acctggggaa acggcccacc aaggacagct     1980
acacgctgac ggaggagcta gctgagtatg ctgaaatccg ggtcaagtga aggagctggg     2040
ggcagcctgc gtggctgacc cccctcagga ccctcgctgg cccccactgg ctgtgggctc     2100
ccttcctccc aaaagtatcg ggggctgggg caggagggga gtgaggcagg tgacagtgag     2160
gtcctggggg cctgacctcc ccctccttcc cagctgcccc tccctgccag cacccccacg     2220
ccctcattac ggctcctctc taacctcctt taccctcatc tgtctggagg ggagctctgt     2280
ctgtccgtgt tatttattgc tacttcctgc ctggtctcct gccccacac ctggccctgg     2340 ggcctgtaca aagggacat gaaataaatg ccccaaagcc                            2380
```

<210> SEQ ID NO 6
<211> LENGTH: 626
<212> TYPE: PRT
<213> ORGANISM: Homo sapiens

<400> SEQUENCE: 6

```
Met Ile Phe Leu Thr Ala Leu Pro Leu Phe Trp Ile Met Ile Ser Ala
 1               5                  10                  15

Ser Arg Gly Gly His Gly Ala Trp Met Pro Ser Ser Ile Ser Ala
                20                  25                  30

Phe Glu Gly Thr Cys Val Ser Ile Pro Cys Arg Phe Asp Phe Pro Asp
            35                  40                  45

Glu Leu Arg Pro Ala Val Val His Gly Val Trp Tyr Phe Asn Ser Pro
        50                  55                  60

Tyr Pro Lys Asn Tyr Pro Pro Val Phe Lys Ser Arg Thr Gln Val
 65                  70                  75                  80

Val His Glu Ser Phe Gln Gly Arg Ser Arg Leu Leu Gly Asp Leu Gly
                85                  90                  95

Leu Arg Asn Cys Thr Leu Leu Leu Ser Asn Val Ser Pro Glu Leu Gly
            100                 105                 110

Gly Lys Tyr Tyr Phe Arg Gly Asp Leu Gly Gly Tyr Asn Gln Tyr Thr
        115                 120                 125
```

```
Phe Ser Glu His Ser Val Leu Asp Ile Val Asn Thr Pro Asn Ile Val
    130                 135                 140

Val Pro Pro Glu Val Val Ala Gly Thr Glu Val Glu Val Ser Cys Met
145                 150                 155                 160

Val Pro Asp Asn Cys Pro Glu Leu Arg Pro Glu Leu Ser Trp Leu Gly
                165                 170                 175

His Glu Gly Leu Gly Glu Pro Ala Val Leu Gly Arg Leu Arg Glu Asp
                180                 185                 190

Glu Gly Thr Trp Val Gln Val Ser Leu Leu His Phe Val Pro Thr Arg
            195                 200                 205

Glu Ala Asn Gly His Arg Leu Gly Cys Gln Ala Ser Phe Pro Asn Thr
    210                 215                 220

Thr Leu Gln Phe Glu Gly Tyr Ala Ser Met Asp Val Lys Tyr Pro Pro
225                 230                 235                 240

Val Ile Val Glu Met Asn Ser Ser Val Glu Ala Ile Glu Gly Ser His
                245                 250                 255

Val Ser Leu Leu Cys Gly Ala Asp Ser Asn Pro Pro Pro Leu Leu Thr
                260                 265                 270

Trp Met Arg Asp Gly Thr Val Leu Arg Glu Ala Val Ala Glu Ser Leu
            275                 280                 285

Leu Leu Glu Leu Glu Glu Val Thr Pro Ala Glu Asp Gly Val Tyr Ala
    290                 295                 300

Cys Leu Ala Glu Asn Ala Tyr Gly Gln Asp Asn Arg Thr Val Gly Leu
305                 310                 315                 320

Ser Val Met Tyr Ala Pro Trp Lys Pro Thr Val Asn Gly Thr Met Val
                325                 330                 335

Ala Val Glu Gly Glu Thr Val Ser Ile Leu Cys Ser Thr Gln Ser Asn
            340                 345                 350

Pro Asp Pro Ile Leu Thr Ile Phe Lys Glu Lys Gln Ile Leu Ser Thr
    355                 360                 365

Val Ile Tyr Glu Ser Glu Leu Gln Leu Glu Leu Pro Ala Val Ser Pro
370                 375                 380

Glu Asp Asp Gly Glu Tyr Trp Cys Val Ala Glu Asn Gln Tyr Gly Gln
385                 390                 395                 400

Arg Ala Thr Ala Phe Asn Leu Ser Val Glu Phe Ala Pro Val Leu Leu
                405                 410                 415

Leu Glu Ser His Cys Ala Ala Ala Arg Asp Thr Val Gln Cys Leu Cys
                420                 425                 430

Val Val Lys Ser Asn Pro Glu Pro Ser Val Ala Phe Glu Leu Pro Ser
            435                 440                 445

Arg Asn Val Thr Val Asn Glu Ser Glu Arg Glu Phe Val Tyr Ser Glu
    450                 455                 460

Arg Ser Gly Leu Val Leu Thr Ser Ile Leu Thr Leu Arg Gly Gln Ala
465                 470                 475                 480

Gln Ala Pro Pro Arg Val Ile Cys Thr Ala Arg Asn Leu Tyr Gly Ala
                485                 490                 495

Lys Ser Leu Glu Leu Pro Phe Gln Gly Ala His Arg Leu Met Trp Ala
                500                 505                 510

Lys Ile Gly Pro Val Gly Ala Val Val Ala Phe Ala Ile Leu Ile Ala
            515                 520                 525

Ile Val Cys Tyr Ile Thr Gln Thr Arg Arg Lys Lys Asn Val Thr Glu
    530                 535                 540

Ser Pro Ser Phe Ser Ala Gly Asp Asn Pro Pro Val Leu Phe Ser Ser
```

```
                545                 550                 555                 560

Asp Phe Arg Ile Ser Gly Ala Pro Glu Lys Tyr Glu Ser Glu Arg Arg
                565                 570                 575

Leu Gly Ser Glu Arg Arg Leu Leu Gly Leu Arg Gly Glu Pro Pro Glu
            580                 585                 590

Leu Asp Leu Ser Tyr Ser His Ser Asp Leu Gly Lys Arg Pro Thr Lys
        595                 600                 605

Asp Ser Tyr Thr Leu Thr Glu Glu Leu Ala Glu Tyr Ala Glu Ile Arg
    610                 615                 620

Val Lys
625

<210> SEQ ID NO 7
<211> LENGTH: 57
<212> TYPE: PRT
<213> ORGANISM: Unknown Organism
<220> FEATURE:
<223> OTHER INFORMATION: Description of Unknown Organism: Mammalian MAG
      Idg5 sequence

<400> SEQUENCE: 7

Cys Val Val Lys Ser Asn Pro Glu Pro Ser Val Ala Phe Glu Leu Pro
 1               5                  10                  15

Ser Arg Asn Val Thr Val Asn Glu Thr Glu Arg Glu Phe Val Tyr Ser
            20                  25                  30

Glu Arg Ser Gly Leu Leu Leu Thr Ser Ile Leu Thr Leu Arg Gly Gln
        35                  40                  45

Ala Gln Ala Pro Pro Arg Val Ile Cys
    50                  55

<210> SEQ ID NO 8
<211> LENGTH: 3579
<212> TYPE: DNA
<213> ORGANISM: Homo sapiens

<400> SEQUENCE: 8
atggaagacc tggaccagtc tcctctggtc tcgtcctcgg acagcccacc ccggccgcag      60
cccgcgttca gtaccagtt cgtgagggag cccgaggacg aggaggaaga agaggaggag     120
gaagaggagg acgaggacga agacctggag gagctggagg tgctggagag gaagcccgcc     180
gccgggctgt ccgcggcccc agtgcccacc gccctgccg ccggcgcgcc cctgatggac     240
ttcggaaatg acttcgtgcc gccggcgccc cggggacccc tgccgccgc tcccccgtc      300 gccccggagc ggcagccgtc ttgggacccg agcccggtgt cgtcgaccgt gcccgcgcca     360
tccccgctgt ctgctgccgc agtctcgccc tccaagctcc ctgaggacga cgagcctccg     420
gcccggcctc cccctcctcc cccggccagc gtgagcccc aggcagagcc cgtgtggacc     480
ccgccagccc cggctcccgc cgcgcccccc tccaccccgg ccgcgcccaa gcgcaggggc     540
tcctcgggct cagtggatga gacccttttt gctcttcctg ctgcatctga gcctgtgata     600
cgctcctctg cagaaaatat ggacttgaag gagcagccag gtaacactat ttcggctggt     660
caagaggatt tcccatctgt cctgcttgaa actgctgctt ctcttccttc tctgtctcct     720
ctctcagccg cttctttcaa agaacatgaa taccttggta atttgtcaac agtattaccc     780
actgaaggaa cacttcaaga aaatgtcagt gaagcttcta agaggtctc agagaaggca     840 aaaactctac tcatagatag agatttaaca gagtttttcag aattagaata ctcagaaatg     900
ggatcatcgt tcagtgtctc tccaaaagca gaatctgccg taatagtagc aaatcctagg     960
```

```
gaagaaataa tcgtgaaaaa taaagatgaa gaagagaagt tagttagtaa taacatcctt    1020
cataatcaac aagagttacc tacagctctt actaaattgg ttaaagagga tgaagttgtg    1080
tcttcagaaa aagcaaaaga cagttttaat gaaagagagt tgcagtgga agctcctatg     1140 agggaggaat atgcagactt caaaccattt gagcgagtat gggaagtgaa agatagtaag    1200
gaagatagtg atatgttggc tgctggaggt aaaatcgaga gcaacttgga aagtaaagtg    1260
gataaaaaat gttttgcaga tagccttgag caaactaatc acgaaaaaga tagtgagagt    1320
agtaatgatg atacttcttt ccccagtacg ccagaaggta taaaggatcg tccaggagca    1380
tatatcacat gtgctccctt taacccagca gcaactgaga gcattgcaac aaacattttt    1440
cctttgttag gagatcctac ttcagaaaat aagaccgatg aaaaaaaaat agaagaaaag    1500
aaggcccaaa tagtaacaga gaagaatact agcaccaaaa catcaaaccc tttctcttgta  1560 gcagcacagg attctgagac agattatgtc acaacagata atttaacaaa ggtgactgag    1620
gaagtcgtgg caaacatgcc tgaaggcctg actccagatt tagtacagga agcatgtgaa    1680
agtgaattga atgaagttac tggtacaaag attgcttatg aaacaaaaat ggacttggtt    1740
caaacatcag aagttatgca agagtcactc tatcctgcag cacagctttg cccatcattt    1800
gaagagtcag aagctactcc ttcaccagtt ttgcctgaca ttgttatgga agcaccattg    1860
aattctgcag ttcctagtgc tggtgcttcc gtgatacagc ccagctcatc accattagaa    1920
gcttcttcag ttaattatga aagcataaaa catgagcctg aaaacccccc accatatgaa    1980
gaggccatga gtgtatcact aaaaaaagta tcaggaataa aggaagaaat taaagagcct    2040
gaaaatatta atgcagctct tcaagaaaca gaagctcctt atatatctat tgcatgtgat    2100
ttaattaaag aaacaaagct ttctgctgaa ccagctccgg atttctctga ttattcagaa    2160
atggcaaaag ttgaacagcc agtgcctgat cattctgagc tagttgaaga ttcctcacct    2220
gattctgaac cagttgactt atttagtgat gattcaatac ctgacgttcc acaaaaacaa    2280
gatgaaactg tgatgcttgt gaaagaaagt ctcactgaga cttcatttga gtcaatgata    2340
gaatatgaaa ataaggaaaa actcagtgct ttgccacctg agggaggaaa gccatatttg    2400
gaatctttta agctcagttt agataacaca aaagatccc  tgttacctga tgaagtttca    2460
acattgagca aaaaggagaa aattcctttg cagatggagg agctcagtac tgcagtttat    2520
tcaaatgatg acttatttat ttctaaggaa gcacagataa gagaaactga aacgttttca    2580
gattcatctc caattgaaat tatagatgag ttccctacat tgatcagttc taaaactgat    2640
tcattttcta aattagccag ggaatatact gacctagaag tatcccacaa aagtgaaatt    2700
gctaatgccc cggatggagc tgggtcattg ccttgcacag aattgcccca tgacctttct    2760
ttgaagaaca tacaacccaa agttgaagag aaaatcagtt tctcagatga cttttctaaa    2820
aatgggtctg ctacatcaaa ggtgctctta ttgcctccag atgtttctgc tttggccact    2880
caagcagaga tagagagcat agttaaaccc aaagttcttg tgaaagaagc tgagaaaaaa    2940
cttccttccg atacagaaaa agaggacaga tcaccatctg ctatattttc agcagagctg    3000
agtaaaactt cagttgttga cctcctgtac tggagagaca ttaagaagac tggagtggtg    3060
tttggtgcca gcctattcct gctgctttca ttgacagtat tcagcattgt gagcgtaaca    3120
gcctacattg ccttggccct gctctctgtg accatcagct ttaggatata caagggtgtg    3180
atccaagcta tccagaaatc agatgaaggc cacccattca gggcatatct ggaatctgaa    3240
gttgctatat ctgaggagtt ggttcagaag tacagtaatt ctgctcttgg tcatgtgaac    3300
```

-continued

```
tgcacgataa aggaactcag gcgcctcttc ttagttgatg atttagttga ttctctgaag   3360
tttgcagtgt tgatgtgggt atttacctat gttggtgcct tgtttaatgg tctgacacta   3420
ctgattttgg ctctcatttc actcttcagt gttcctgtta tttatgaacg gcatcaggcg   3480
cagatagatc attatctagg acttgcaaat aagaatgtta aagatgctat ggctaaaatc   3540
caagcaaaaa tccctggatt gaagcgcaaa gctgaatga                          3579
```

```
<210> SEQ ID NO 9
<211> LENGTH: 1192
<212> TYPE: PRT
<213> ORGANISM: Homo sapiens

<400> SEQUENCE: 9
```

| | | | | | | | | | | | | | | |
|---|---|---|---|---|---|---|---|---|---|---|---|---|---|---|
| Met | Glu | Asp | Leu | Asp | Gln | Ser | Pro | Leu | Val | Ser | Ser | Asp | Ser | Pro |
| 1 | | | | 5 | | | | | 10 | | | | | 15 |
| Pro | Arg | Pro | Gln | Pro | Ala | Phe | Lys | Tyr | Gln | Phe | Val | Arg | Glu | Pro |
| | | | 20 | | | | | 25 | | | | | 30 | |
| Asp | Glu | Glu | Glu | Glu | Glu | Glu | Glu | Glu | Glu | Asp | Glu | Asp | Glu | Asp |
| | | | 35 | | | | | 40 | | | | | 45 | |
| Leu | Glu | Glu | Leu | Glu | Val | Leu | Glu | Arg | Lys | Pro | Ala | Ala | Gly | Leu | Ser |
| | 50 | | | | | 55 | | | | | 60 | | | | |
| Ala | Ala | Pro | Val | Pro | Thr | Ala | Pro | Ala | Ala | Gly | Ala | Pro | Leu | Met | Asp |
| 65 | | | | | 70 | | | | | 75 | | | | | 80 |
| Phe | Gly | Asn | Asp | Phe | Val | Pro | Pro | Ala | Pro | Arg | Gly | Pro | Leu | Pro | Ala |
| | | | | 85 | | | | | 90 | | | | | 95 | |
| Ala | Pro | Pro | Val | Ala | Pro | Glu | Arg | Gln | Pro | Ser | Trp | Asp | Pro | Ser | Pro |
| | | | | 100 | | | | | 105 | | | | | 110 | |
| Val | Ser | Ser | Thr | Val | Pro | Ala | Pro | Ser | Pro | Leu | Ser | Ala | Ala | Ala | Val |
| | | | 115 | | | | | 120 | | | | | 125 | | |
| Ser | Pro | Ser | Lys | Leu | Pro | Glu | Asp | Asp | Glu | Pro | Pro | Ala | Arg | Pro | Pro |
| | 130 | | | | | 135 | | | | | 140 | | | | |
| Pro | Pro | Pro | Pro | Ala | Ser | Val | Ser | Pro | Gln | Ala | Glu | Pro | Val | Trp | Thr |
| 145 | | | | | 150 | | | | | 155 | | | | | 160 |
| Pro | Pro | Ala | Pro | Ala | Pro | Ala | Ala | Pro | Ser | Thr | Pro | Ala | Ala | Pro |
| | | | | | 165 | | | | | 170 | | | | | 175 |
| Lys | Arg | Arg | Gly | Ser | Ser | Gly | Ser | Val | Asp | Glu | Thr | Leu | Phe | Ala | Leu |
| | | | 180 | | | | | 185 | | | | | 190 | | |
| Pro | Ala | Ala | Ser | Glu | Pro | Val | Ile | Arg | Ser | Ser | Ala | Glu | Asn | Met | Asp |
| | | 195 | | | | | 200 | | | | | 205 | | | |
| Leu | Lys | Glu | Gln | Pro | Gly | Asn | Thr | Ile | Ser | Ala | Gly | Gln | Glu | Asp | Phe |
| | 210 | | | | | 215 | | | | | 220 | | | | |
| Pro | Ser | Val | Leu | Leu | Glu | Thr | Ala | Ala | Ser | Leu | Pro | Ser | Leu | Ser | Pro |
| 225 | | | | | 230 | | | | | 235 | | | | | 240 |
| Leu | Ser | Ala | Ala | Ser | Phe | Lys | Glu | His | Glu | Tyr | Leu | Gly | Asn | Leu | Ser |
| | | | | 245 | | | | | 250 | | | | | 255 | |
| Thr | Val | Leu | Pro | Thr | Glu | Gly | Thr | Leu | Gln | Glu | Asn | Val | Ser | Glu | Ala |
| | | | 260 | | | | | 265 | | | | | 270 | | |
| Ser | Lys | Glu | Val | Ser | Glu | Lys | Ala | Lys | Thr | Leu | Leu | Ile | Asp | Arg | Asp |
| | | 275 | | | | | 280 | | | | | 285 | | | |
| Leu | Thr | Glu | Phe | Ser | Glu | Leu | Glu | Tyr | Ser | Glu | Met | Gly | Ser | Ser | Phe |
| | 290 | | | | | 295 | | | | | 300 | | | | |
| Ser | Val | Ser | Pro | Lys | Ala | Glu | Ser | Ala | Val | Ile | Val | Ala | Asn | Pro | Arg |
| 305 | | | | | 310 | | | | | 315 | | | | | 320 |
| Glu | Glu | Ile | Ile | Val | Lys | Asn | Lys | Asp | Glu | Glu | Glu | Lys | Leu | Val | Ser |

-continued

```
                325                 330                 335
Asn Asn Ile Leu His Asn Gln Gln Glu Leu Pro Thr Ala Leu Thr Lys
            340                 345                 350

Leu Val Lys Glu Asp Glu Val Val Ser Ser Glu Lys Ala Lys Asp Ser
            355                 360                 365

Phe Asn Glu Lys Arg Val Ala Val Glu Ala Pro Met Arg Glu Glu Tyr
            370                 375                 380

Ala Asp Phe Lys Pro Phe Glu Arg Val Trp Glu Val Lys Asp Ser Lys
385                 390                 395                 400

Glu Asp Ser Asp Met Leu Ala Ala Gly Gly Lys Ile Glu Ser Asn Leu
                405                 410                 415

Glu Ser Lys Val Asp Lys Lys Cys Phe Ala Asp Ser Leu Glu Gln Thr
            420                 425                 430

Asn His Glu Lys Asp Ser Glu Ser Ser Asn Asp Asp Thr Ser Phe Pro
            435                 440                 445

Ser Thr Pro Glu Gly Ile Lys Asp Arg Pro Gly Ala Tyr Ile Thr Cys
            450                 455                 460

Ala Pro Phe Asn Pro Ala Ala Thr Glu Ser Ile Ala Thr Asn Ile Phe
465                 470                 475                 480

Pro Leu Leu Gly Asp Pro Thr Ser Glu Asn Lys Thr Asp Glu Lys Lys
                485                 490                 495

Ile Glu Glu Lys Lys Ala Gln Ile Val Thr Glu Lys Asn Thr Ser Thr
                500                 505                 510

Lys Thr Ser Asn Pro Phe Leu Val Ala Ala Gln Asp Ser Glu Thr Asp
            515                 520                 525

Tyr Val Thr Thr Asp Asn Leu Thr Lys Val Thr Glu Glu Val Val Ala
            530                 535                 540

Asn Met Pro Glu Gly Leu Thr Pro Asp Leu Val Gln Glu Ala Cys Glu
545                 550                 555                 560

Ser Glu Leu Asn Glu Val Thr Gly Thr Lys Ile Ala Tyr Glu Thr Lys
                565                 570                 575

Met Asp Leu Val Gln Thr Ser Glu Val Met Gln Glu Ser Leu Tyr Pro
            580                 585                 590

Ala Ala Gln Leu Cys Pro Ser Phe Glu Glu Ser Glu Ala Thr Pro Ser
            595                 600                 605

Pro Val Leu Pro Asp Ile Val Met Glu Ala Pro Leu Asn Ser Ala Val
            610                 615                 620

Pro Ser Ala Gly Ala Ser Val Ile Gln Pro Ser Ser Pro Leu Glu
625                 630                 635                 640

Ala Ser Ser Val Asn Tyr Glu Ser Ile Lys His Glu Pro Glu Asn Pro
                645                 650                 655

Pro Pro Tyr Glu Glu Ala Met Ser Val Ser Leu Lys Lys Val Ser Gly
            660                 665                 670

Ile Lys Glu Glu Ile Lys Glu Pro Glu Asn Ile Asn Ala Ala Leu Gln
            675                 680                 685

Glu Thr Glu Ala Pro Tyr Ile Ser Ile Ala Cys Asp Leu Ile Lys Glu
            690                 695                 700

Thr Lys Leu Ser Ala Glu Pro Ala Pro Asp Phe Ser Asp Tyr Ser Glu
705                 710                 715                 720

Met Ala Lys Val Glu Gln Pro Val Pro Asp His Ser Glu Leu Val Glu
                725                 730                 735

Asp Ser Ser Pro Asp Ser Glu Pro Val Asp Leu Phe Ser Asp Asp Ser
            740                 745                 750
```

```
Ile Pro Asp Val Pro Gln Lys Gln Asp Glu Thr Val Met Leu Val Lys
        755                 760                 765

Glu Ser Leu Thr Glu Thr Ser Phe Glu Ser Met Ile Glu Tyr Glu Asn
        770                 775                 780

Lys Glu Lys Leu Ser Ala Leu Pro Pro Glu Gly Gly Lys Pro Tyr Leu
785                 790                 795                 800

Glu Ser Phe Lys Leu Ser Leu Asp Asn Thr Lys Asp Thr Leu Leu Pro
                805                 810                 815

Asp Glu Val Ser Thr Leu Ser Lys Lys Glu Lys Ile Pro Leu Gln Met
            820                 825                 830

Glu Glu Leu Ser Thr Ala Val Tyr Ser Asn Asp Asp Leu Phe Ile Ser
        835                 840                 845

Lys Glu Ala Gln Ile Arg Glu Thr Glu Thr Phe Ser Asp Ser Ser Pro
        850                 855                 860

Ile Glu Ile Ile Asp Glu Phe Pro Thr Leu Ile Ser Ser Lys Thr Asp
865                 870                 875                 880

Ser Phe Ser Lys Leu Ala Arg Glu Tyr Thr Asp Leu Glu Val Ser His
                885                 890                 895

Lys Ser Glu Ile Ala Asn Ala Pro Asp Gly Ala Gly Ser Leu Pro Cys
            900                 905                 910

Thr Glu Leu Pro His Asp Leu Ser Leu Lys Asn Ile Gln Pro Lys Val
        915                 920                 925

Glu Glu Lys Ile Ser Phe Ser Asp Asp Phe Ser Lys Asn Gly Ser Ala
        930                 935                 940

Thr Ser Lys Val Leu Leu Leu Pro Pro Asp Val Ser Ala Leu Ala Thr
945                 950                 955                 960

Gln Ala Glu Ile Glu Ser Ile Val Lys Pro Lys Val Leu Val Lys Glu
                965                 970                 975

Ala Glu Lys Lys Leu Pro Ser Asp Thr Glu Lys Glu Asp Arg Ser Pro
            980                 985                 990

Ser Ala Ile Phe Ser Ala Glu Leu Ser Lys Thr Ser Val Val Asp Leu
        995                 1000                1005

Leu Tyr Trp Arg Asp Ile Lys Lys Thr Gly Val Val Phe Gly Ala Ser
     1010                1015                1020

Leu Phe Leu Leu Leu Ser Leu Thr Val Phe Ser Ile Val Ser Val Thr
     1025                1030                1035                1040

Ala Tyr Ile Ala Leu Ala Leu Leu Ser Val Thr Ile Ser Phe Arg Ile
                1045                1050                1055

Tyr Lys Gly Val Ile Gln Ala Ile Gln Lys Ser Asp Glu Gly His Pro
            1060                1065                1070

Phe Arg Ala Tyr Leu Glu Ser Glu Val Ala Ile Ser Glu Glu Leu Val
        1075                1080                1085

Gln Lys Tyr Ser Asn Ser Ala Leu Gly His Val Asn Cys Thr Ile Lys
     1090                1095                1100

Glu Leu Arg Arg Leu Phe Leu Val Asp Asp Leu Val Asp Ser Leu Lys
1105                1110                1115                1120

Phe Ala Val Leu Met Trp Val Phe Thr Tyr Val Gly Ala Leu Phe Asn
                1125                1130                1135

Gly Leu Thr Leu Leu Ile Leu Ala Leu Ile Ser Leu Phe Ser Val Pro
            1140                1145                1150

Val Ile Tyr Glu Arg His Gln Ala Gln Ile Asp His Tyr Leu Gly Leu
        1155                1160                1165
```

Ala Asn Lys Asn Val Lys Asp Ala Met Ala Lys Ile Gln Ala Lys Ile
    1170                1175                1180

Pro Gly Leu Lys Arg Lys Ala Glu
1185                1190

<210> SEQ ID NO 10
<211> LENGTH: 198
<212> TYPE: DNA
<213> ORGANISM: Homo sapiens

<400> SEQUENCE: 10
aggatataca agggtgtgat ccaagctatc cagaaatcag atgaaggcca cccattcagg    60
gcatatctgg aatctgaagt tgctatatct gaggagttgg ttcagaagta cagtaattct   120
gctcttggtc atgtgaactg cacgataaag gaactcaggc gcctcttctt agttgatgat   180
ttagttgatt ctctgaag                                                  198

<210> SEQ ID NO 11
<211> LENGTH: 66
<212> TYPE: PRT
<213> ORGANISM: Homo sapiens

<400> SEQUENCE: 11

Arg Ile Tyr Lys Gly Val Ile Gln Ala Ile Gln Lys Ser Asp Glu Gly
  1               5                  10                  15

His Pro Phe Arg Ala Tyr Leu Glu Ser Glu Val Ala Ile Ser Glu Glu
             20                  25                  30

Leu Val Gln Lys Tyr Ser Asn Ser Ala Leu Gly His Val Asn Cys Thr
         35                  40                  45

Ile Lys Glu Leu Arg Arg Leu Phe Leu Val Asp Asp Leu Val Asp Ser
     50                  55                  60

Leu Lys
 65

<210> SEQ ID NO 12
<211> LENGTH: 1794
<212> TYPE: DNA
<213> ORGANISM: Mus sp.

<400> SEQUENCE: 12
ctgagctggc aagcagagcc cacagccaga aaccctttccg actcccacaa caagacgacc    60
tttaagctgc aagtttcccg gagaaaatga gatactgata gtgaagacga cattatgggc   120
tttgatggaa tatcagatac tgaaaatgtc ttcctgcctg ttcatccttc tgtttctcac   180
gcctggcatc ttatgcattt gtcctctcca gtgtacatgc acagagaggc acaggcatgt   240
ggactgttca ggcagaaact tgactacatt accacctgga ctgcaggaga acattataca   300
tttaaacctg tcttataacc actttactga tctgcataac cagttaaccc catataccaa   360
tctgagaacc ctggatattt caaacaacag gcttgaaagt ctgcctgctc agttacctcg   420
gtctctctgg aacatgtctg ctgctaacaa caatattaaa cttcttgaca aatctgatac   480
tgcttatcag tggaacctta atacctggat gtttctaag aatatgctgg aaaaggttgt   540
tctcattaaa aataccctaa gaagtctcga ggttcttaac ctcagcagta caagctttg    600 gacagttcca accaacatgc cttccaaact gcatatcgtg gacctgtcta ataactcact   660
gacacaaatc cttccaggga cattaataaa cctgacaaat ctcacacatc tttacctgca   720
caacaataaa ttcacattca ttccagaaca gtcttttgac caacttttgc agttgcaaga   780

-continued

```
gataactctt cataataaca ggtggtcatg tgaccataaa caaaacatta cttacttatt      840
gaagtgggtg atggaaacga aagcccatgt gatagggact ccttgttcta agcaagtatc      900
ctctctaaag gaacagagca tgtaccccac acctcctggg tttacctcaa gcttatttac      960
tatgagtgag atgcagacag tggacaccat taactctttg agtatggtaa ctcaacccaa     1020
agtgaccaaa acacccaaac aatatcgagg aaaggaaacc acatttggtg tcactctaag     1080
caaagatacc acttttagta gcactgatag ggctgtggtg gcctacccag aagacacacc     1140
cacagaaatg accaattccc atgaagcagc agctgcaact ctaactattc acctccagga     1200
tggaatgagt tcaaatgcaa gcctcaccag tgcaacaaag tcaccccccaa gccccgtgac     1260 cctcagcata gctcgtggca tgccaaataa cttctctgaa atgcctcgac aaagcacaac     1320
cctcaactta cggagggaag aaaccactgc aaatggaaac actcggccac cttctgcggc     1380
tagtgcttgg aaagtaaatg cctcgctcct tttaatgctc aatgctgtgg tcatgctggc     1440
aggctgaggg tctgcagttt ctgaaacgaa ggagaacctt cctccatgat gtacagttgg     1500
gaaaacgtgc ccctatctaa ccagtgattc aagctatatt atgtattcaa gaaagccagt     1560
cttatatttc tgactttgat gtaaatgaag taatttgtct taattaaaag aagtgcacaa     1620
tgtcttggta cttgctgcta ttttcctgtc ttaagtaaaa ctaatgactt ttttttttaa     1680
tgaaatgttt tcttttaag gcttcaactt attgcacaaa ctataaagag catctaaact     1740
ttaatatgta ttttatgtat gtttacactg tcaaatgtct gggacaaaat aaaa           1794
```

<210> SEQ ID NO 13
<211> LENGTH: 440
<212> TYPE: PRT
<213> ORGANISM: Mus sp.

<400> SEQUENCE: 13

```
Met Glu Tyr Gln Ile Leu Lys Met Ser Ser Cys Leu Phe Ile Leu Leu
  1               5                  10                  15

Phe Leu Thr Pro Gly Ile Leu Cys Ile Cys Pro Leu Gln Cys Thr Cys
                 20                  25                  30

Thr Glu Arg His Arg His Val Asp Cys Ser Gly Arg Asn Leu Thr Thr
             35                  40                  45

Leu Pro Pro Gly Leu Gln Glu Asn Ile Ile His Leu Asn Leu Ser Tyr
         50                  55                  60

Asn His Phe Thr Asp Leu His Asn Gln Leu Thr Pro Tyr Thr Asn Leu
     65                  70                  75                  80

Arg Thr Leu Asp Ile Ser Asn Asn Arg Leu Glu Ser Leu Pro Ala Gln
                 85                  90                  95

Leu Pro Arg Ser Leu Trp Asn Met Ser Ala Ala Asn Asn Asn Ile Lys
                100                 105                 110

Leu Leu Asp Lys Ser Asp Thr Ala Tyr Gln Trp Asn Leu Lys Tyr Leu
            115                 120                 125

Asp Val Ser Lys Asn Met Leu Glu Lys Val Val Leu Ile Lys Asn Thr
        130                 135                 140

Leu Arg Ser Leu Glu Val Leu Asn Leu Ser Ser Asn Lys Leu Trp Thr
145                 150                 155                 160

Val Pro Thr Asn Met Pro Ser Lys Leu His Ile Val Asp Leu Ser Asn
                165                 170                 175

Asn Ser Leu Thr Gln Ile Leu Pro Gly Thr Leu Ile Asn Leu Thr Asn
            180                 185                 190

Leu Thr His Leu Tyr Leu His Asn Asn Lys Phe Thr Phe Ile Pro Glu
```

```
                       195                 200                 205

Gln Ser Phe Asp Gln Leu Leu Gln Leu Gln Glu Ile Thr Leu His Asn
    210                 215                 220

Asn Arg Trp Ser Cys Asp His Lys Gln Asn Ile Thr Tyr Leu Leu Lys
225                 230                 235                 240

Trp Val Met Glu Thr Lys Ala His Val Ile Gly Thr Pro Cys Ser Lys
                245                 250                 255

Gln Val Ser Ser Leu Lys Glu Gln Ser Met Tyr Pro Thr Pro Pro Gly
            260                 265                 270

Phe Thr Ser Ser Leu Phe Thr Met Ser Glu Met Gln Thr Val Asp Thr
        275                 280                 285

Ile Asn Ser Leu Ser Met Val Thr Gln Pro Lys Val Thr Lys Thr Pro
    290                 295                 300

Lys Gln Tyr Arg Gly Lys Glu Thr Thr Phe Gly Val Thr Leu Ser Lys
305                 310                 315                 320

Asp Thr Thr Phe Ser Ser Thr Asp Arg Ala Val Val Ala Tyr Pro Glu
                325                 330                 335

Asp Thr Pro Thr Glu Met Thr Asn Ser His Glu Ala Ala Ala Ala Thr
            340                 345                 350

Leu Thr Ile His Leu Gln Asp Gly Met Ser Ser Asn Ala Ser Leu Thr
        355                 360                 365

Ser Ala Thr Lys Ser Pro Pro Ser Pro Val Thr Leu Ser Ile Ala Arg
    370                 375                 380

Gly Met Pro Asn Asn Phe Ser Glu Met Pro Arg Gln Ser Thr Thr Leu
385                 390                 395                 400

Asn Leu Arg Arg Glu Glu Thr Thr Ala Asn Gly Asn Thr Arg Pro Pro
                405                 410                 415

Ser Ala Ala Ser Ala Trp Lys Val Asn Ala Ser Leu Leu Leu Met Leu
            420                 425                 430

Asn Ala Val Val Met Leu Ala Gly
        435                 440

<210> SEQ ID NO 14
<211> LENGTH: 59
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (1)
<223> OTHER INFORMATION: Asn, Gln or Cys
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (3)
<223> OTHER INFORMATION: Ile, Val or Phe
<220> FEATURE:
<221> NAME/KEY: MOD_RES
<222> LOCATION: (4)..(6)
<223> OTHER INFORMATION: Variable amino acid
<220> FEATURE:
<221> NAME/KEY: MOD_RES
<222> LOCATION: (7)
<223> OTHER INFORMATION: Pro or Asp
<220> FEATURE:
<221> NAME/KEY: MOD_RES
<222> LOCATION: (9)
<223> OTHER INFORMATION: Variable amino acid
```

-continued

```
<220> FEATURE:
<221> NAME/KEY: MOD_RES
<222> LOCATION: (10)
<223> OTHER INFORMATION: Ser or His
<220> FEATURE:
<221> NAME/KEY: MOD_RES
<222> LOCATION: (11)..(14)
<223> OTHER INFORMATION: Variable amino acid
<220> FEATURE:
<221> NAME/KEY: MOD_RES
<222> LOCATION: (15)
<223> OTHER INFORMATION: Leu or Tyr
<220> FEATURE:
<221> NAME/KEY: MOD_RES
<222> LOCATION: (16)..(18)
<223> OTHER INFORMATION: Variable amino acid
<220> FEATURE:
<221> NAME/KEY: MOD_RES
<222> LOCATION: (19)
<223> OTHER INFORMATION: Glu or Asn
<220> FEATURE:
<221> NAME/KEY: MOD_RES
<222> LOCATION: (20)
<223> OTHER INFORMATION: Val or Ile
<220> FEATURE:
<221> NAME/KEY: MOD_RES
<222> LOCATION: (21)
<223> OTHER INFORMATION: Thr or Ala
<220> FEATURE:
<221> NAME/KEY: MOD_RES
<222> LOCATION: (22)
<223> OTHER INFORMATION: Ile, Leu or Val
<220> FEATURE:
<221> NAME/KEY: MOD_RES
<222> LOCATION: (23)
<223> OTHER INFORMATION: Variable amino acid
<220> FEATURE:
<221> NAME/KEY: MOD_RES
<222> LOCATION: (24)
<223> OTHER INFORMATION: Glu or Asn
<220> FEATURE:
<221> NAME/KEY: MOD_RES
<222> LOCATION: (25)..(30)
<223> OTHER INFORMATION: Variable amino acid
<220> FEATURE:
<221> NAME/KEY: MOD_RES
<222> LOCATION: (31)
<223> OTHER INFORMATION: His, Ser or Tyr
<220> FEATURE:
<221> NAME/KEY: MOD_RES
<222> LOCATION: (32)..(34)
<223> OTHER INFORMATION: Variable amino acid
<220> FEATURE:
<221> NAME/KEY: MOD_RES
<222> LOCATION: (35)
<223> OTHER INFORMATION: Ile, Ser or Leu
<220> FEATURE:
<221> NAME/KEY: MOD_RES
<222> LOCATION: (36)
<223> OTHER INFORMATION: Gly or Thr
<220> FEATURE:
<221> NAME/KEY: MOD_RES
<222> LOCATION: (37)
<223> OTHER INFORMATION: His, Leu or Tyr
<220> FEATURE:
<221> NAME/KEY: MOD_RES
<222> LOCATION: (38)
<223> OTHER INFORMATION: Leu or Val
<220> FEATURE:
<221> NAME/KEY: MOD_RES
<222> LOCATION: (39)
<223> OTHER INFORMATION: Leu or Asn
<220> FEATURE:
<221> NAME/KEY: MOD_RES
<222> LOCATION: (40)
<223> OTHER INFORMATION: Ser, Thr or Lys
<220> FEATURE:
<221> NAME/KEY: MOD_RES
<222> LOCATION: (41)
```

```
<223> OTHER INFORMATION: Ser, Thr or Trp
<220> FEATURE:
<221> NAME/KEY: MOD_RES
<222> LOCATION: (42)
<223> OTHER INFORMATION: Ile or Val
<220> FEATURE:
<221> NAME/KEY: MOD_RES
<222> LOCATION: (43)
<223> OTHER INFORMATION: Leu, Lys or Met
<220> FEATURE:
<221> NAME/KEY: MOD_RES
<222> LOCATION: (44)
<223> OTHER INFORMATION: Glu or Thr
<220> FEATURE:
<221> NAME/KEY: MOD_RES
<222> LOCATION: (45)
<223> OTHER INFORMATION: Leu or Thr
<220> FEATURE:
<221> NAME/KEY: MOD_RES
<222> LOCATION: (46)
<223> OTHER INFORMATION: Arg or Lys
<220> FEATURE:
<221> NAME/KEY: MOD_RES
<222> LOCATION: (47)
<223> OTHER INFORMATION: Ala, Arg or Gly
<220> FEATURE:
<221> NAME/KEY: MOD_RES
<222> LOCATION: (48)..(49)
<223> OTHER INFORMATION: Variable amino acid
<220> FEATURE:
<221> NAME/KEY: MOD_RES
<222> LOCATION: (50)
<223> OTHER INFORMATION: Ile, Leu or Gln
<220> FEATURE:
<221> NAME/KEY: MOD_RES
<222> LOCATION: (51)
<223> OTHER INFORMATION: Ala, Val or Gly
<220> FEATURE:
<221> NAME/KEY: MOD_RES
<222> LOCATION: (52)
<223> OTHER INFORMATION: Variable amino acid
<220> FEATURE:
<221> NAME/KEY: MOD_RES
<222> LOCATION: (53)
<223> OTHER INFORMATION: Pro or Asp
<220> FEATURE:
<221> NAME/KEY: MOD_RES
<222> LOCATION: (54)
<223> OTHER INFORMATION: Variable amino acid
<220> FEATURE:
<221> NAME/KEY: MOD_RES
<222> LOCATION: (55)
<223> OTHER INFORMATION: Val or Ser
<220> FEATURE:
<221> NAME/KEY: MOD_RES
<222> LOCATION: (56)..(57)
<223> OTHER INFORMATION: Variable amino acid
<220> FEATURE:
<221> NAME/KEY: MOD_RES
<222> LOCATION: (58)
<223> OTHER INFORMATION: Leu, Thr or Val
<220> FEATURE:
<221> NAME/KEY: MOD_RES
<222> LOCATION: (59)
<223> OTHER INFORMATION: Ser or Lys

<400> SEQUENCE: 14

Xaa Xaa Xaa Xaa Xaa Xaa Xaa Glu Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
    50                  55
```

```
<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ala Arg Asp Thr Val Gln Cys Leu Cys Val Val Lys Ser Asn
 1               5                  10                  15

Pro Glu Pro Ser Val Ala Phe Glu Leu Pro Ser Arg Asn Val
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Ala Phe Glu Leu Pro Ser Arg Asn Val Thr Val Asn Glu Thr Glu
 1               5                  10                  15

Arg Glu Phe Val Tyr Ser Glu Arg Ser Gly Leu Leu Leu Thr
            20                  25                  30

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Pro Glu Pro Ser
 1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Pro Ser Arg Asn Val Thr Val Asn Glu
 1               5                  10

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Val Thr Val Asn Glu
 1               5

<210> SEQ ID NO 20
```

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Val Lys Ser Asn Pro Glu Pro Ser Val Ala Phe Glu Leu Pro Ser
 1               5                  10                  15

Arg Asn Val Thr Val Asn Glu Thr Glu
            20                  25

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Gly Leu Leu Leu Thr
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ile Leu Thr Leu Arg
 1               5

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Tyr Ser Glu Arg Ser Gly Leu Leu Leu Thr Ser Ile Leu Thr Leu
 1               5                  10                  15

Arg Gly Gln Ala Gln Ala Pro Pro Arg Val Ile Cys Thr Ser Arg Asn
            20                  25                  30

Leu Tyr Gly Thr Gln Ser
        35

<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Ser Glu Arg Ser Gly Leu Leu Leu Thr Ser Ile Leu Thr Leu Arg
 1               5                  10                  15

Gly Gln Ala Gln Ala Pro Pro Arg Val
            20                  25
```

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Asp Glu Gly His
 1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Leu Glu Ser Glu Val Ala Ile Ser Glu
 1               5                  10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Leu Glu Ser Glu Val Ala Ile Ser Glu Glu Leu Val
 1               5                  10

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Val Ala Ile Ser Glu
 1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Val Ala Ile Ser Glu Glu Leu Val
 1               5

<210> SEQ ID NO 30
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 30

Ala Ile Gln Lys Ser Asp Glu Gly His Pro Phe Arg Ala Tyr Leu Glu
 1               5                  10                  15

Ser Glu Val Ala Ile Ser Glu Glu Leu
            20                  25

<210> SEQ ID NO 31
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ile Gln Lys Ser Asp Glu Gly His Pro Phe Arg Ala Tyr Leu Glu
 1               5                  10                  15

Ser Glu Val Ala Ile Ser Glu Glu Leu Val
            20                  25

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Asn Ser Ala Leu Gly His Val Asn Ser Thr Ile Lys Glu Leu Arg
 1               5                  10                  15

Arg Leu Phe Leu Val Asp Asp Leu Val
            20                  25

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Gly His Val Asn Cys
 1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Ile Lys Glu Leu Arg
 1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 35

Ile Pro Glu Gln Ser
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Gln Leu Gln Glu Ile Thr Leu His Asn
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Ile Thr Leu His Asn
1               5

<210> SEQ ID NO 38
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Phe Thr Phe Ile Pro Glu Gln Ser Phe Asp Gln Leu Leu Gln Leu
1               5                   10                  15

Gln Glu Ile Thr Leu His Asn Asn Arg
            20                  25

<210> SEQ ID NO 39
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

His Lys Gln Asn Ile Thr Tyr Leu Leu Lys Trp Val Met Glu Thr Lys
1               5                   10                  15

Ala His Val Ile Gly Thr Pro Cys Ser
            20                  25

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40
```

```
Ile Thr Tyr Leu Leu Lys
  1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Trp Val Met Glu Thr Lys
  1               5

<210> SEQ ID NO 42
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser His Gly Gly Leu Thr Leu Ala Ser Asn Ser Gly Glu Asn Asp Phe
  1               5                  10                  15

Asn Pro Arg Phe Arg Ile Ser Ser Ala Pro Asn Ser Leu Arg
             20                  25                  30

<210> SEQ ID NO 43
<211> LENGTH: 59
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)..(6)
<223> OTHER INFORMATION: Variable amino acid
<220> FEATURE:
<221> NAME/KEY: MOD_RES
<222> LOCATION: (9)
<223> OTHER INFORMATION: Variable amino acid
<220> FEATURE:
<221> NAME/KEY: MOD_RES
<222> LOCATION: (11)..(14)
<223> OTHER INFORMATION: Variable amino acid
<220> FEATURE:
<221> NAME/KEY: MOD_RES
<222> LOCATION: (16)..(18)
<223> OTHER INFORMATION: Variable amino acid
<220> FEATURE:
<221> NAME/KEY: MOD_RES
<222> LOCATION: (23)
<223> OTHER INFORMATION: Variable amino acid
<220> FEATURE:
<221> NAME/KEY: MOD_RES
<222> LOCATION: (25)..(30)
<223> OTHER INFORMATION: Variable amino acid
<220> FEATURE:
<221> NAME/KEY: MOD_RES
<222> LOCATION: (32)..(34)
<223> OTHER INFORMATION: Variable amino acid
<220> FEATURE:
<221> NAME/KEY: MOD_RES
<222> LOCATION: (48)..(49)
<223> OTHER INFORMATION: Variable amino acid
<220> FEATURE:
```

```
<221> NAME/KEY: MOD_RES
<222> LOCATION: (52)
<223> OTHER INFORMATION: Variable amino acid
<220> FEATURE:
<221> NAME/KEY: MOD_RES
<222> LOCATION: (54)
<223> OTHER INFORMATION: Variable amino acid
<220> FEATURE:
<221> NAME/KEY: MOD_RES
<222> LOCATION: (56)..(57)
<223> OTHER INFORMATION: Variable amino acid

<400> SEQUENCE: 43

Asn Xaa Ile Xaa Xaa Xaa Pro Glu Xaa Ser Xaa Xaa Xaa Xaa Leu Xaa
 1               5                  10                  15

Xaa Xaa Glu Val Thr Ile Xaa Glu Xaa Xaa Xaa Xaa Xaa His Xaa
            20                  25                  30

Xaa Xaa Ile Gly His Leu Leu Ser Ser Ile Leu Glu Leu Arg Ala Xaa
        35                  40                  45

Xaa Ile Ala Xaa Pro Xaa Val Xaa Xaa Leu Ser
    50                  55
```